(12) United States Patent
Brown et al.

(10) Patent No.: US 7,875,615 B2
(45) Date of Patent: Jan. 25, 2011

(54) SUBSTITUTED TRIAZOLE DERIVATIVES AS OXYTOCIN ANTAGONISTS

(75) Inventors: Alan Daniel Brown, Sandwich (GB); David Ellis, Sandwich (GB); Christopher Ronald Smith, San Diego, CA (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 12/621,927

(22) Filed: Nov. 19, 2009

(65) Prior Publication Data
US 2010/0063064 A1    Mar. 11, 2010

Related U.S. Application Data

(62) Division of application No. 11/928,513, filed on Oct. 30, 2007, now Pat. No. 7,649,003, which is a division of application No. 10/944,959, filed on Sep. 20, 2004, now Pat. No. 7,291,640.

(60) Provisional application No. 60/535,846, filed on Jan. 12, 2004, provisional application No. 60/556,555, filed on Mar. 26, 2004, provisional application No. 60/588,852, filed on Jul. 16, 2004.

(30) Foreign Application Priority Data

Sep. 22, 2003  (GB) .............................. 0322159.5
Feb. 12, 2004  (GB) .............................. 0403150.6
Jul. 5, 2004   (GB) .............................. 0415110.6

(51) Int. Cl.
*A61K 31/501* (2006.01)
*C07D 403/14* (2006.01)

(52) U.S. Cl. .................... 514/252.05; 514/252.03; 544/238

(58) Field of Classification Search ............ 514/252.05, 514/252.03; 544/238
See application file for complete search history.

(56) References Cited

U.S. PATENT DOCUMENTS

| | | | |
|---|---|---|---|
| 2,503,059 A | 4/1950 | Miescher et al. | 260/309.6 |
| 2,599,000 A | 1/1952 | Kerwin et al. | 260/570.7 |
| 3,381,009 A | 4/1968 | Palazzo et al. | 260/268 |
| 3,511,836 A | 5/1970 | Hess et al. | 260/256.4 |
| 3,527,761 A | 9/1970 | Archibald et al. | 260/293 |
| 3,997,666 A | 12/1976 | Witte et al. | 424/250 |
| 4,026,894 A | 5/1977 | Winn et al. | 260/256.4 |
| 4,188,390 A | 2/1980 | Campbell et al. | 424/251 |
| 4,252,721 A | 2/1981 | Silvestrini et al. | 260/243.3 |
| 4,315,007 A | 2/1982 | Manoury et al. | 424/251 |
| 4,703,063 A | 10/1987 | Imai et al. | 514/603 |
| 5,426,107 A | 6/1995 | Bell et al. | 514/234.2 |
| 5,693,652 A | 12/1997 | Takase et al. | 514/322 |
| 5,719,283 A | 2/1998 | Bell et al. | 544/262 |
| 5,861,396 A | 1/1999 | Niewohner et al. | 514/234.2 |
| 5,945,117 A | 8/1999 | El-Rashidy et al. | 424/430 |
| 2004/0067945 A1 | 4/2004 | Niewohner et al. | 514/243 |

FOREIGN PATENT DOCUMENTS

| | | |
|---|---|---|
| EP | 0995750 | 10/1999 |
| EP | 0995751 | 10/1999 |
| EP | 1092718 | 10/2000 |
| EP | 1092719 | 10/2000 |
| EP | 1097719 | 11/2000 |
| EP | 1293503 | 5/2001 |
| WO | WO 9307149 | 4/1993 |
| WO | WO 9312095 | 6/1993 |
| WO | WO 9400453 | 1/1994 |
| WO | WO 9519978 | 7/1995 |
| WO | WO 9830560 | 7/1998 |
| WO | WO 9849166 | 11/1998 |
| WO | WO 9902159 | 1/1999 |
| WO | WO 9930697 | 6/1999 |
| WO | WO 9954333 | 10/1999 |
| WO | WO 0002550 | 1/2000 |
| WO | WO 0024745 | 5/2000 |
| WO | WO 0028993 | 5/2000 |
| WO | WO 0127112 | 4/2001 |
| WO | WO 0127113 | 4/2001 |
| WO | WO 0158880 | 8/2001 |
| WO | WO 0187855 | 11/2001 |
| WO | WO 03053437 | 7/2003 |

OTHER PUBLICATIONS

"Tautomer." Retrieved online via the Internet, Feb. 11, 2008, URL: http://en.wikipedia.org.giki/Tautomer.
Kakefuda et al., [5-(4-biphenyl)-3-methyl-4-phenyl-1,2,4-triazole Derivatives as a Novel Class of Selective Antagonists for the Human Vasopressin V1A Receptor, J. Med. Chem, 45 (2002) 2589-2598].

(Continued)

*Primary Examiner*—Rebecca L Anderson
*Assistant Examiner*—Samantha L Shterengarts
(74) *Attorney, Agent, or Firm*—Jennifer A. Kispert; John A. Wichtowski

(57) ABSTRACT

The present invention relates to a class of substituted 1,2,4-triazoles of formula (I) with activity as oxytocin antagonists, uses thereof, processes for the preparation thereof and compositions containing said inhibitors. These inhibitors have utility in a variety of therapeutic areas including sexual dysfunction, particularly premature ejaculation (P.E.).

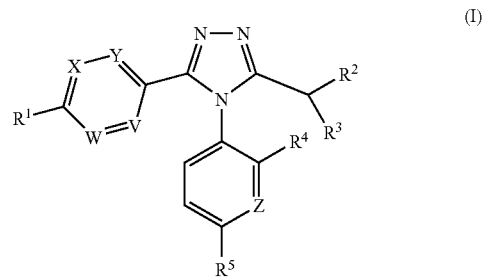

(I)

19 Claims, No Drawings

OTHER PUBLICATIONS

Akerlund, Mats, *Annals New York Academy Of Sciences*, "Vascularization of Human Endometrium", pp. 47-55.

Arletti, et al., *Peptides*, "Influence of Oxytocin on Feeding Behavior in the Rat", vol. 10, pp. 89-93, (1989).

Berman, et al., *Urology*, "Female Sexual Dysfunction: Incidence, Pathophysiology, Evauation, and Treatment Options", vol. 54, pp. 385-391, (1999).

Berman, et al, *International Journal of Impotence Research*, "Definition and classification of female sexual disorders", vol. 10 (S-2), pp. S-104-S106, (1998).

Clemence, et al., *European Journal of Med. Chem.* "Synthesis and Analgesic Activity in the 1,2,4-Triazole Series", vol. 20(3); pp. 257-266, (1985).

Gimpl, et al, *Physiological Reviews*, "The Oxytocin Recptor System: Structure, Function, and Regulation", vol. 81(2), pp. 629-683, (2001).

Melman, et al, *The Journal of Urology*, "The Epidemiology and Pathophysiology of Erectile Dysfunction", vol. 161 (1), pp. 5-11, (1999).

Nicholson, et al., *Advanced Exp. Med. & Biology*, "Oxytocin and Prostatic Function", pp. 529-538 (1995).

Rotella, et al., *Journal of Med. Chemistry*, "N-3-Substituted Imidazoquinazolinones: Potent and Selective PDE5 Inhibitors as Potential Agents for Treatment of Erectile Dysfunction", vol. 43, pp. 1257-1263, (2000).

Truitt, et al., *Science*, "Identification of a Potential Ejaculation generator in the Spinal Cord", vol. 297, pp. 1566-1569, (2002).

SUBSTITUTED TRIAZOLE DERIVATIVES AS OXYTOCIN ANTAGONISTS

This application is a division of U.S. patent application Ser. No. 11/928,513 filed Oct. 30, 2007 which claims the benefit of U.S. patent application Ser. No. 10/944,959, filed on Sep. 20, 2004, which claims the benefit of United Kingdom Application Nos. 0322159.5, 0403150.6 and 0415110.6, filed on Sep. 22, 2003, Feb. 12, 2004 and Jul. 5, 2004, respectively, and the benefit of U.S. Provisional Application Nos. 60/535,846, 60/556,555 and 60/588,852, filed on Jan. 12, 2004, Mar. 26, 2004 and Jul. 16, 2004, respectively.

The present invention relates to a class of substituted 1,2,4-triazoles with activity as oxytocin antagonists, uses thereof, processes for the preparation thereof and compositions containing said inhibitors. These inhibitors have utility in a variety of therapeutic areas including sexual dysfunction, particularly premature ejaculation (P.E.).

Eur. J. Med. Chem. 1985, 20(3), pp 257-266, refers to derivatives of 1,2,4-triazoles having analgesic and antiinflammatory properties. WO 03/053437 refers to 1,2,4-triazoles having activity as oxytocin antagonists. EP 1,293,503 refers to derivatives of 1,2,4-triazoles having glycine transporter inhibiting properties.

SUMMARY OF INVENTION

The first aspect of the present invention provides for compounds of formula (I)

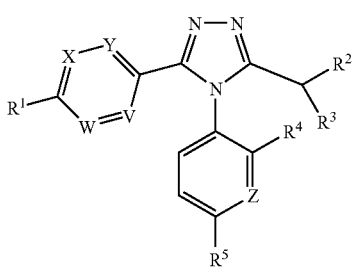

(I)

wherein

V, W, X and Y, which may be the same or different, represent C—$R^6$ or N;

Z is C—H or N;

$R^1$ is selected from:
(i) a phenyl ring substituted with two or more substituents, which may be the same or different, each independently selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$; and
(ii) a five to seven membered aromatic heterocyclic ring containing 1-3 hetero atoms selected from N, O and S and N-oxides thereof; said ring being optionally substituted with two or more substituents, which may be the same or different, selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$;

$R^2$ is selected from:
(i) H, OH, $OR^9$, $NR^7R^8$, $NR^7C(O)R^{10}$ and $N[C(O)R^{10}]_2$;
(ii) a 5-7 membered N-linked heterocycle containing 1-3 heteroatoms selected from N, O and S; said ring being optionally substituted with one or more groups selected from $(C_1$-$C_6)$alkyl, $(C_1$-$C_6)$alkoxy and $C(O)NR^7R^8$; and
(iii) $(C_1$-$C_6)$alkyl optionally substituted with an N-linked 5-7 membered heterocycle containing 1-3 heteroatoms selected from N, O and S;

$R^3$ is selected from H and $(C_1$-$C_6)$alkyl;

$R^4$ is selected from H, $(C_1$-$C_6)$alkyl and $OR^9$;

$R^5$ is selected from halo, $(C_1$-$C_6)$alkyl, $(C_1$-$C_6)$alkoxy, $NR^7R^8$, $NR^7C(O)R^{10}$ and $N[C(O)R^{10}]_2$;

$R^6$ is selected from H, halo, $(C_1$-$C_6)$alkyl, $(C_1$-$C_6)$alkoxy, cyano, $NR^7R^8$, $NR^7C(O)R^{10}$, $N[C(O)R^{10}]_2$ and $C(O)NR^7R^8$;

$R^7$ and $R^8$, which may be the same or different, are selected from H and $(C_1$-$C_6)$alkyl;

$R^9$ is $(C_1$-$C_6)$alkyl, which is optionally substituted with one or more groups each independently selected from $(C_1$-$C_6)$alkoxy and an N-linked 5-7 membered heterocycle containing 1-3 heteroatoms selected from N, O and S; and $R^{10}$ is selected from $(C_1$-$C_6)$alkyl and $(C_1$-$C_6)$alkoxy;

a tautomer thereof or a pharmaceutically acceptable salt, solvate or polymorph of said compound or tautomer;

with the proviso that the compound of formula (I) is not 3-ethyl-5-(4-imidazol-1-ylphenyl)-4-(4-methoxyphenyl)-4H-[1,2,4]triazole,
3-(3',5'-dichlorobiphenyl-4-yl)-4-(2-methoxyphenyl)-5-methyl-4H-[1,2,4]triazole,
3-(3',5'-bis-trifluoromethylbiphenyl-4-yl)-4-(2-fluorophenyl)-5-methyl-4H-[1,2,4]triazole, or
3-(3',5'-bis-trifluoromethylbiphenyl-4-yl)-5-methyl-4-(3-trifluoromethylphenyl)-4H-[1,2,4]triazole.

Unless otherwise indicated, alkyl and alkoxy groups may be straight or branched and contain 1 to 6 carbon atoms and preferably 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Halo means fluoro, chloro, bromo or iodo and is preferably fluoro.

A heterocycle may be saturated, partially saturated or aromatic. Examples of heterocyclic groups are thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl. Examples of aromatic heterocyclic groups are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, triazinyl.

Unless otherwise indicated, the term substituted means substituted by one or more defined groups. In the case where groups may be selected from a number of alternative groups, the selected groups may be the same or different.

Preferred aspects of the invention are defined below.

In a preferred aspect, the present invention comprises compounds of formula (I) wherein 1 or 2 of the groups V, W, X and Y represent N when the remainder represent C—$R^6$;

Z is C—H or N;

$R^1$ is selected from:
(i) a phenyl ring substituted with two or more substituents, which may be the same or different, each independently selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$; and (ii) a five to seven membered aromatic heterocyclic ring containing 1-3 hetero atoms selected from N, O and S and N-oxides thereof; said ring being optionally substituted with two or more substituents, which may be the same or different, selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$;

Preferably, $R^2$ is selected from:
(i) H, $(C_1$-$C_6)$alkyl, $(C_1$-$C_6)$alkoxy-$(C_1$-$C_6)$alkoxy, $NR^7R^8$, $NR^7C(O)R^{10}$ and $N[C(O)R^{10}]_2$; and
(ii) a 5-7 membered N-linked heterocycle containing 1-3 heteroatoms selected from N, O and S; said ring optionally substituted with one or more groups selected from $(C_1$-$C_6)$alkyl, $(C_1$-$C_6)$alkoxy and $C(O)NR^7R^8$;

$R^3$ is selected from H and $(C_1$-$C_6)$alkyl;

$R^4$ is selected from H, $(C_1$-$C_6)$alkyl and $OR^9$;

$R^5$ is $(C_1$-$C_3)$alkyl, $(C_1$-$C_3)$alkoxy or $NR^7R^8$;

$R^6$ is H, halo, $(C_1$-$C_6)$alkyl, $(C_1$-$C_6)$alkoxy, cyano or $NR^7R^8$;

$R^7$ and $R^8$, which may be the same or different, are selected from H and $(C_1$-$C_6)$alkyl;

$R^9$ is $(C_1$-$C_6)$alkyl optionally substituted with $(C_1$-$C_6)$alkoxy; and $R^{10}$ is selected from $(C_1$-$C_6)$alkyl and $(C_1$-$C_6)$alkoxy;

a tautomer thereof or a pharmaceutically acceptable salt, solvate or polymorph of said compound or tautomer.

In another preferred aspect, the present invention comprises compounds of formula (I) wherein 1 or 2 of the groups V, W and Y represent N when the remainder represent C—$R^6$ and X is CH;

Z is C—H or N;

$R^1$ is selected from:
(i) a phenyl ring substituted with two substituents, which may be the same or different, each independently selected from halo, $(C_1$-$C_3)$alkyl, $(C_1$-$C_3)$alkoxy, and cyano; and
(ii) a pyridyl ring or N-oxide thereof each substituted with two substituents, which may be the same or different, each independently selected from halo, $(C_1$-$C_3)$alkyl, $(C_1$-$C_3)$alkoxy, and cyano;

$R^2$ is selected from:
(i) H, $(C_1$-$C_3)$alkoxy, $(C_1$-$C_3)$alkoxy-$(C_1$-$C_3)$alkoxy and $N((C_1$-$C_3)$alkyl$)_2$; and
(ii) a 5 membered N-linked heterocycle containing 1-3 nitrogen atoms, said ring optionally substituted with $C(O)NR^7R^8$;

$R^3$ is selected from H and $(C_1$-$C_6)$alkyl;

$R^4$ is selected from H, $(C_1$-$C_6)$alkyl and $OR^9$;

$R^5$ is $(C_1$-$C_3)$alkyl, $(C_1$-$C_3)$alkoxy or $NR^7R^8$;

$R^6$ is H, $(C_1$-$C_6)$alkyl, $(C_1$-$C_6)$alkoxy or $NR^7R^8$;

$R^7$ and $R^8$, which may be the same or different, are selected from H and $(C_1$-$C_6)$alkyl; and $R^9$ is $(C_1$-$C_6)$alkyl optionally substituted with methoxy;

a tautomer thereof or a pharmaceutically acceptable salt, solvate or polymorph of said compound or tautomer.

In another preferred aspect, the present invention comprises compounds of formula (I) wherein W and Y are each independently CH or N and X and V are each CH;

Z is N;

$R^1$ is a phenyl ring substituted with two substituents, which may be the same or different, each independently selected from fluoro, chloro, methyl, methoxy, and cyano;

$R^2$ is selected from H, methoxy, ethoxy, 2-methoxyethoxy, dimethylamino, 1,2,3-triazol-2-yl and pyrolidinyl, the latter being optionally substituted by $CONH_2$;

$R^3$ is selected from H and $(C_1$-$C_6)$alkyl;

$R^4$ is H; and $R^5$ is methoxy;

a tautomer thereof or a pharmaceutically acceptable salt, solvate or polymorph of said compound or tautomer.

Preferred embodiments of the compounds of formula (I) according to the above aspects are those that incorporate two or more of the following preferences.

Preferably, 1 or 2 of the groups V, W, X and Y represent N when the remainder represent C—$R^6$.

In a preferred embodiment, X is CH.

In a preferred embodiment, 1 or 2 of the groups V, W and Y represent N when the remainder represent C—$R^6$ and X is CH;

Preferably, Y is N or $CR^6$.

More preferably, V, W and Y are each independently CH, C—$OCH_3$ or N.

Most preferably, W and Y are each independently CH or N.

In the most preferred embodiment, W and Y are each independently CH or N and X and V are each CH.

In a preferred embodiment, Z is N.

In another preferred embodiment, Z is CH.

Preferably, $R^1$ is selected from:
(i) a phenyl ring substituted with two or more substituents, which may be the same or different, each independently selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$; and
(ii) a five to seven membered aromatic heterocyclic ring containing 1-3 hetero atoms selected from N, O and S and N-oxides thereof; said ring being optionally substituted with two or more substituents, which may be the same or different, selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$;

More preferably, $R^1$ is selected from:
(i) a phenyl ring substituted with two substituents, which may be the same or different, each independently selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$; and
(ii) a pyridyl ring or N-oxide thereof each substituted with two substituents, which may be the same or different, each independently selected from halo, $(C_1$-$C_6)$alkyl, $(C_1$-$C_6)$alkoxy, cyano, $C(O)NR^7R^8$, $NR^7R^8$, $NR^7C(O)R^{10}$ and $N[C(O)R^{10}]_2$.

Yet more preferably, $R^1$ is selected from:
(i) a phenyl ring substituted with two substituents, which may be the same or different, each independently selected from halo, $(C_1$-$C_3)$alkyl, $(C_1$-$C_3)$alkoxy and cyano; and (ii) a pyridyl ring or N-oxide thereof each substituted with two substituents, which may be the same or different, each independently selected from halo, $(C_1-C_3)$alkyl, $(C_1-C_3)$alkoxy and cyano.

In a preferred embodiment, $R^1$ is a phenyl ring substituted with two substituents, which may be the same or different, each independently selected from fluoro, chloro, methyl, methoxy and cyano.

In another preferred embodiment, $R^1$ is pyridine-N-oxide substituted with two methyl groups.

Preferably, $R^2$ is selected from:
(i) H, $(C_1-C_6)$alkoxy, $(C_1-C_6)$alkoxy-$(C_1-C_6)$alkoxy, $NR^7R^8$, $NR^7C(O)R^{10}$ and $N[C(O)R^{10}]_2$; and
(ii) a 5-7 membered N-linked heterocycle containing 1-3 heteroatoms selected from N, O and S; said ring optionally substituted with one or more groups selected from $(C_1-C_6)$alkyl, $(C_1-C_6)$alkoxy and $C(O)NR^7R^8$.

More preferably, $R^2$ is selected from:
(i) H, $(C_1-C_3)$alkoxy, $(C_1-C_3)$alkoxy-$(C_1-C_3)$alkoxy and $N((C_1-C_3)alkyl)_2$; and
(ii) a 5 membered N-linked heterocycle containing 1-3 nitrogen atoms, said ring optionally substituted with $C(O)NR^7R^8$.

Yet more preferably, $R^2$ is selected from H, methoxy, ethoxy, 2-methoxyethoxy, dimethylamino, 1,2,3-triazol-2-yl and pyrolidinyl, the latter being optionally substituted by $CONH_2$.

Most preferably, $R^2$ is selected from H and methoxy.
Preferably, $R^3$ is H or $(C_1-C_3)$alkyl.
Most preferably, $R^3$ is H.
Preferably, $R^4$ is H, $(C_1-C_3)$alkyl or $OR^9$.
More preferably, $R^4$ is H, $(C_1-C_3)$alkyl or $(C_1-C_3)$alkoxy.
Most preferably, $R^4$ is H, methyl or methoxy.
In a preferred embodiment, $R^4$ is H.
Preferably, $R^5$ is $(C_1-C_3)$alkyl, $(C_1-C_3)$alkoxy or $NR^7R^8$.
More preferably, $R^5$ is $(C_1-C_3)$alkoxy or $NR^7R^8$.
Most preferably, $R^5$ is methoxy or $NHCH_3$.
In a preferred embodiment, $R^5$ is methoxy.
Preferably, $R^6$ is H, halo, $(C_1-C_6)$alkyl, $(C_1-C_6)$alkoxy, cyano or $NR^7R^8$.
More preferably, $R^6$ is H, $(C_1-C_6)$alkyl, $(C_1-C_6)$alkoxy or $NR^7R^8$.
Yet more preferably, $R^6$ is H, $(C_1-C_3)$alkyl or $(C_1-C_3)$alkoxy.
Most preferably, $R^6$ is H, methyl or methoxy.
In a preferred embodiment, $R^6$ is H or methyl.
In a most preferred embodiment, $R^6$ is H.
Preferably, $R^7$ is H or $(C_1-C_3)$alkyl.
Most preferably, $R^7$ is H or methyl.
Preferably, $R^8$ is H or $(C_1-C_3)$alkyl.
Most preferably, $R^8$ is H or methyl.
Preferably, $R^9$ is $(C_1-C_6)$alkyl optionally substituted with $(C_1-C_6)$alkoxy.
More preferably, $R^9$ is $(C_1-C_6)$alkyl optionally substituted with methoxy.
Most preferably, $R^9$ is methyl.

Preferred compounds of formula (I) are:
2-(4-fluoro-2-methylphenyl)-5-(5-methoxymethyl-4-(6-methoxypyridin-3-yl)-4H-[1,2,4]triazol-3-yl)-pyridine;
2-(2,3-dimethylphenyl)-5-(5-methoxymethyl-4-(6-methoxypyridin-3-yl)-4H-[1,2,4]triazol-3-yl)-pyridine;
5-(4-fluoro-2-methylphenyl)-2-(5-methoxymethyl-4-(6-methoxypyridin-3-yl)-4H-[1,2,4]triazol-3-yl)-pyridine;
5-(2,3-dimethylphenyl)-2-(5-methoxymethyl-4-(6-methoxypyridin-3-yl)-4H-[1,2,4]triazol-3-yl)-pyridine;
1-[5-[5-(2,3-dimethylphenyl)-pyridin-2-yl]-4-(6-methoxypyridin-3-yl)-4H-[1,2,4]triazol-3-ylmethyl]-pyrrolidine-(2S)-2-carboxylic acid amide;
5-(2,3-dimethylphenyl)-2-(5-pyrrolidin-1-ylmethyl-4-(6-methoxypyridin-3-yl)-4H-[1,2,4]triazol-3-yl)-pyridine;
2-(4-fluoro-2-methylphenyl)-5-[5-methoxymethyl-4-(6-methoxypyridin-3-yl)-4H-[1,2,4]triazol-3-yl]-pyrazine;
2-(2,3-dimethylphenyl)-5-[5-methoxymethyl-4-(6-methoxypyridin-3-yl)-4H-[1,2,4]triazol-3-yl]-pyrazine;
2-(4-fluoro-2-methylphenyl)-5-[4-(6-methoxypyridin-3-yl)-5-methyl-4H-[1,2,4]triazol-3-yl]-pyrazine;
2-(2,3-dimethylphenyl)-5-[4-(6-methoxypyridin-3-yl)-5-methyl-4H-[1,2,4]triazol-3-yl]-pyrazine;
2-(4-cyano-2-methylphenyl)-5-[4-(6-methoxypyridin-3-yl)-5-methyl-4H-[1,2,4]triazol-3-yl]-pyrazine;
2-(5-fluoro-2-methoxyphenyl)-5-[4-(6-methoxypyridin-3-yl)-5-methyl-4H-[1,2,4]triazol-3-yl]-pyrazine;
2-(4-cyano-2-methylphenyl)-5-[5-methoxymethyl-4-(6-methoxypyridin-3-yl)-4H-[1,2,4]triazol-3-yl]-pyrazine;
5-(4-cyano-2-methylphenyl)-2-[5-methoxymethyl-4-(6-methoxypyridin-3-yl)-4H-[1,2,4]triazol-3-yl]-pyridine;
2-(5-fluoro-2-methoxyphenyl)-5-[5-methoxymethyl-4-(6-methoxypyridin-3-yl)-4H-[1,2,4]triazol-3-yl]-pyridine;
2-(2-fluoro-5-methoxyphenyl)-5-[4-(6-methoxypyridin-3-yl)-5-methyl-4H-[1,2,4]triazol-3-yl]-pyrazine;
2-(2-fluoro-5-methyl phenyl)-5-[4-(6-methoxypyridin-3-yl)-5-methyl-4H-[1,2,4]triazol-3-yl]-pyrazine;
2-(2,5-difluorophenyl)-5-[4-(6-methoxypyridin-3-yl)-5-methyl-4H-[1,2,4]triazol-3-yl]-pyrazine;
2-(3,5-dimethylphenyl)-5-[4-(6-methoxypyridin-3-yl)-5-methyl-4H-[1,2,4]triazol-3-yl]-pyrazine;
2-(2,5-dimethylphenyl)-5-[4-(6-methoxypyridin-3-yl)-5-methyl-4H-[1,2,4]triazol-3-yl]-pyrazine;
2-(2,5-dichlorophenyl)-5-[4-(6-methoxypyridin-3-yl)-5-methyl-4H-[1,2,4]triazol-3-yl]-pyrazine;
2-(2-fluoro-5-methoxyphenyl)-5-[4-(6-methoxypyridin-3-yl)-5-methyl-4H-[1,2,4]triazol-3-yl]-pyrazine;
2-(3,5-difluoro-phenyl)-5-[4-(6-methoxypyridin-3-yl)-5-methyl-4H-[1,2,4]triazol-3-yl]-pyrazine;
2-(2,3-dimethylphenyl)-5-[5-[(2-methoxyethoxy)methyl]-4-(6-methoxypyridin-3-yl)-4H-1,2,4-triazol-3-yl]pyridine;
2-(5-chloro-2-methoxyphenyl)-5-[5-[(2-methoxyethoxy) methyl]-4-(6-methoxypyridin-3-yl)-4H-1,2,4-triazol-3-yl]pyridine;
2-(4-fluoro-2-methoxyphenyl)-5-[5-[(2-methoxyethoxy) methyl]-4-(6-methoxypyridin-3-yl)-4H-1,2,4-triazol-3-yl]pyridine;
2-(5-fluoro-2-methoxyphenyl)-5-[5-[(2-methoxyethoxy) methyl]-4-(6-methoxypyridin-3-yl)-4H-1,2,4-triazol-3-yl]pyridine;
2-(5-fluoro-2-methylphenyl)-5-[5-[(2-methoxyethoxy)methyl]-4-(6-methoxypyridin-3-yl)-4H-1,2,4-triazol-3-yl]pyridine;
2-methoxy-5-{3-[(2-methoxyethoxy)methyl]-5-[6-(2-methoxy-5-methylphenyl)pyridin-3-yl]-4H-1,2,4-triazol-4-yl}pyridine;
2-(2-fluoro-3-methoxyphenyl)-5-[5-[(2-methoxyethoxy) methyl]-4-(6-methoxypyridin-3-yl)-4H-1,2,4-triazol-3-yl]pyridine;
2-(3,5-difluorophenyl)-5-[5-[(2-methoxyethoxy)methyl]-4-(6-methoxypyridin-3-yl)-4H-1,2,4-triazol-3-yl]pyridine;
2-(2,5-dimethoxyphenyl)-5-[5-[(2-methoxyethoxy)methyl]-4-(6-methoxypyridin-3-yl)-4H-1,2,4-triazol-3-yl]pyridine;
2-(3-chloro-4-fluorophenyl)-5-[5-[(2-methoxyethoxy)methyl]-4-(6-methoxypyridin-3-yl)-4H-1,2,4-triazol-3-yl] pyridine;

2-(3-fluoro-2-methoxyphenyl)-5-[5-methoxymethyl-4-(6-methoxypyridin-3-yl)-4H-[1,2,4]triazol-3-yl]-pyrazine; and
2-(3-fluoro-2-methoxy-phenyl)-5-[4-(6-methoxy-pyridin-3-yl)-5-methyl-4-H-[1,2,4]triazol-3-yl]-pyrazine;
and tautomers thereof and pharmaceutically acceptable salts, solvates and polymorphs of said compound or tautomer.

Most preferred compounds of formula (I) are:
2-(4-fluoro-2-methylphenyl)-5-(5-methoxymethyl-4-(6-methoxypyridin-3-yl)-4H-[1,2,4]triazol-3-yl)-pyridine;
2-(2,3-dimethylphenyl)-5-(5-methoxymethyl-4-(6-methoxypyridin-3-yl)-4H-[1,2,4]triazol-3-yl)-pyridine;
5-(4-fluoro-2-methylphenyl)-2-(5-methoxymethyl-4-(6-methoxypyridin-3-yl)-4H-[1,2,4]triazol-3-yl)-pyridine;
5-(2,3-dimethylphenyl)-2-(5-methoxymethyl-4-(6-methoxypyridin-3-yl)-4H-[1,2,4]triazol-3-yl)-pyridine;
1-[5-[5-(2,3-dimethylphenyl)-pyridin-2-yl]-4-(6-methoxypyridin-3-yl)-4H-[1,2,4]triazol-3-ylmethyl]-pyrrolidine-(2S)-2-carboxylic acid amide;
5-(2,3-dimethylphenyl)-2-(5-pyrrolidin-1-ylmethyl-4-(6-methoxypyridin-3-yl)-4H-[1,2,4]triazol-3-yl)-pyridine;
2-(4-fluoro-2-methylphenyl)-5-[5-methoxymethyl-4-(6-methoxypyridin-3-yl)-4H-[1,2,4]triazol-3-yl]-pyrazine;
2-(2,3-dimethylphenyl)-5-[5-methoxymethyl-4-(6-methoxypyridin-3-yl)-4H-[1,2,4]triazol-3-yl]-pyrazine;
2-(4-fluoro-2-methylphenyl)-5-[4-(6-methoxypyridin-3-yl)-5-methyl-4H-[1,2,4]triazol-3-yl]-pyrazine;
2-(2,3-dimethylphenyl)-5-[4-(6-methoxypyridin-3-yl)-5-methyl-4H-[1,2,4]triazol-3-yl]-pyrazine;
2-(4-cyano-2-methylphenyl)-5-[4-(6-methoxypyridin-3-yl)-5-methyl-4H-[1,2,4]triazol-3-yl]-pyrazine;
2-(5-fluoro-2-methoxyphenyl)-5-[4-(6-methoxypyridin-3-yl)-5-methyl-4H-[1,2,4]triazol-3-yl]-pyrazine;
2-(4-cyano-2-methylphenyl)-5-[5-methoxymethyl-4-(6-methoxypyridin-3-yl)-4H-[1,2,4]triazol-3-yl]-pyrazine;
5-(4-cyano-2-methylphenyl)-2-[5-methoxymethyl-4-(6-methoxypyridin-3-yl)-4H-[1,2,4]triazol-3-yl]-pyridine;
2-(5-fluoro-2-methoxyphenyl)-5-[5-methoxymethyl-4-(6-methoxypyridin-3-yl)-4H-[1,2,4]triazol-3-yl]-pyridine;
2-(3-fluoro-2-methoxyphenyl)-5-[5-methoxymethyl-4-(6-methoxypyridin-3-yl)-4H-[1,2,4]triazol-3-yl]-pyrazine; and
2-(3-fluoro-2-methoxy-phenyl)-5-[4-(6-methoxy-pyridin-3-yl)-5-methyl-4-H-[1,2,4]triazol-3-yl]-pyrazine;
and tautomers thereof and pharmaceutically acceptable salts, solvates and polymorphs of said compound or tautomer.

Pharmaceutically acceptable salts of the compounds of formula (I) comprise the acid addition salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Hemisalts of acids may also be formed, for example, hemisulphate salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid;
(ii) by removing an acid-labile protecting group from a suitable precursor of the compound of formula (I) using the desired acid; or
(iii) by converting one salt of the compound of formula (I) to another by reaction with an appropriate acid or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric or non-stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include
(i) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and (ii) where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by ($C_1$-$C_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);
(iii) where the compound of formula (I) contains a tertiary amino group, a secondary amino derivative thereof (—$NR^1R^2$→—$NHR^1$ or —$NHR^2$);
(iv) where the compound of formula (I) contains a secondary amino group, a primary derivative thereof (—$NHR^1$→—$NH_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—$CONH_2$→COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, d-lactate, or racemic, for example, dl-tartrate.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of intermediate which provides the best combination of features for this purpose. Such features include the melting point, solubility, processability and yield of the intermediate form and the resulting ease with which the product may be purified on isolation.

Drug Product

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 2 to 30 mg of the compound of formula (I). The overall daily dose will typically be in the range 50 to 100 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 50 mg to 100 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

DESCRIPTION OF INVENTION

Processes

Compounds of general formula (I) where $R^2$ is H, $R^3$ is H and where $R^1$, $R^4$, $R^5$, $R^6$, X, V, W, Y and Z are as described herein may be prepared according to reaction scheme 1.

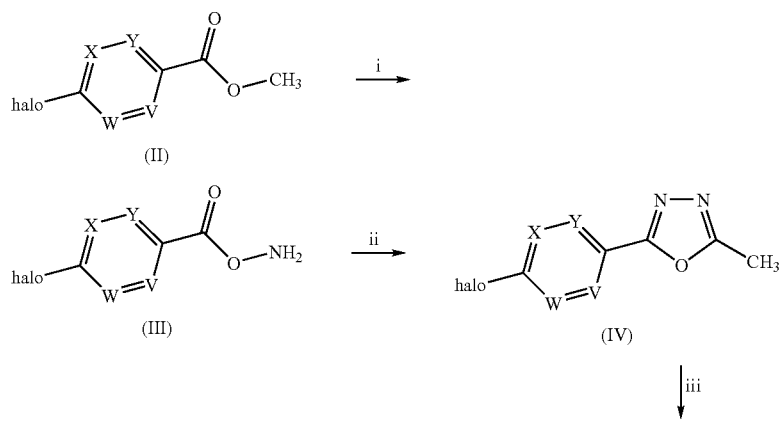

-continued

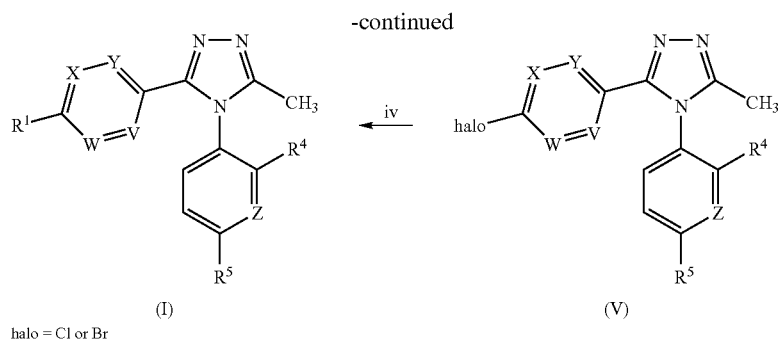

(I)     (V)

halo = Cl or Br

Compounds of formula (II) are either commercially available or can be prepared by analogy with the methods described in *J. Org. Chem.*, 66(2), 605-608; 2001 and UK Pat. Appl., 2219793, 20 Dec. 1989.

Alternatively, when V, W, X or Y=CR$^6$, compounds of formula (II) can be prepared from commercial compounds using standard chemical reactions and transformations of R$^6$.

When R$^6$ is alkoxy and preferably methoxy, R$^6$ is incorporated by substitution of a functional group, preferably chloro, as exemplified in preparations 84-86.

Compounds of formula (III) may be prepared from compounds of formula (II) by process step (i), which comprises reaction with hydrazine monohydrate in a suitable solvent such as methanol or ethanol between −10° C. and reflux. Typical conditions comprise heating 1 equivalent of aryl ester (II) and 1.2-3 equivalents of hydrazine monohydrate in methanol at reflux for 18-48 hours.

Compounds of formula (IV) may be prepared from compounds of formula (III) by process step (ii), which comprises reaction with N,N-dimethylacetamide dimethyl acetal (available from Aldrich) in a suitable solvent such as N,N-dimethylformamide, N-methylpyrrolidine or toluene followed by the addition of a suitable acid catalyst such as trifluoroacetic acid, para-toluenesulfonic acid, camphor sulfonic acid, or hydrochloric acid. Typical conditions comprise heating 1 equivalent of aryl hydrazide (III) and 1.3 equivalents of N,N-dimethylacetamide dimethyl acetal in N,N-dimethylformamide to 60° C. for 2 hours, followed by concentration in vacuo, addition of toluene and 0.025 equivalents of para-toluenesulfonic acid, which is then heated to reflux for 2 hours.

Compounds of formula (V) may be prepared from compounds of formula (IV) by process step (iii), which comprises reaction with a suitable aniline or 3-aminopyridine in the presence of a suitable acid, such as trifluoroacetic acid, para-toluenesulfonic acid, camphor sulfonic acid, or hydrochloric acid in a suitable solvent, such as xylene, heated at 150° C. Typical conditions comprise heating 1 equivalent of 1,2,4-oxadiazole (IV), 2-3 equivalents of aniline or aminopyridine and 0.04-0.1 equivalents of para-toluenesulfonic acid in xylene at 150° C. for 18-23 hours.

Compounds of formula (I) may be prepared from compounds of formula (V) by process step (iv), which comprises a Suzuki coupling reaction with a suitable boronic acid such as 2,3-dimethylphenyl boronic acid (commercially available), in a suitable solvent, in the presence of a base and a palladium catalyst such as [2-[(Dimethylamino-κN)methyl]phenyl-κC](tricyclohexylphosphine) (trifluoroacetato-κO-(SP-4-3)-palladium, prepared as described in *Organometallics*, 2003, 22 (5), 987-999.

The Suzuki coupling reaction can be carried out as described in the literature: Suzuki, A. *Pure & Appl. Chem.* 1985, 57, 1749 and reference contained within; *Angew. Chem. Int. Ed.* 2002, 41, 4176-4211 and references contained within. Typical conditions comprise heating 1 equivalent of aryl bromide (V), 2.5 equivalents of boronic acid, 3 equivalents cesium carbonate. 0.06 equivalents of palladium catalyst from preparation 3 in 1,4-dioxane at 120° C. for 4 hours.

Compounds of general formula (I) where R$^3$ is H and where R$^1$, R$^2$, R$^4$, R$^5$, R$^6$, X, V, W, Y and Z are as described herein, except R$^2$ ≠H, may be prepared according to reaction scheme 2.

Scheme 2

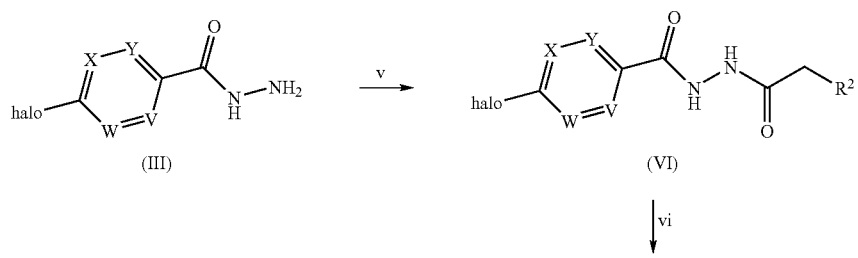

(III)     (VI)

-continued

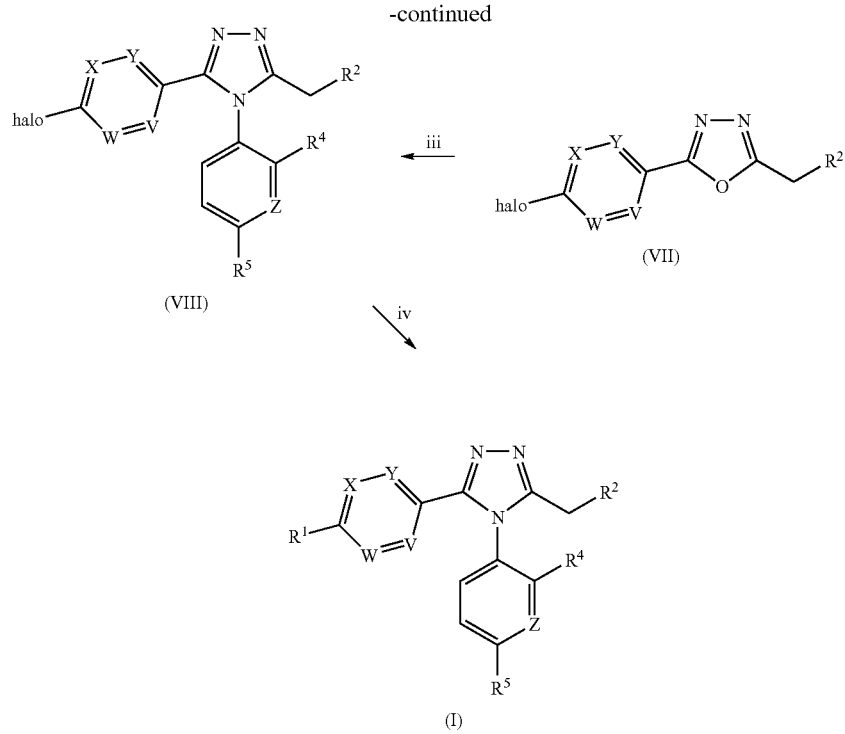

halo = Cl or Br

Compounds of formula (VI) can be prepared from aryl hydrazides of formula (III) by process step (v), which comprises reaction with an acid chloride, such as methoxyacetyl chloride (for $R^2$=$OCH_3$), in the presence of base such as triethylamine, N-methyl morpholine, sodium carbonate or potassium hydroxide. Typical conditions comprise heating 1.0 equivalents of aryl hydrazide (III), 1.0-1.3 equivalents of acid chloride, 1.2-2.0 equivalents of N-methyl morpholine in dichloromethane at 0-25° C. for 3-18 hours.

Compounds of formula (VII) can be prepared from compound (VI) by process step (vi), which comprises reaction with a suitable dehydrating agent such as phosphorous oxychloride, trifluoromethanesulfonic anhydride, or phosphorous pentachloride between a temperature of 25° C. and 110° C. Typical conditions comprise heating 1.0 equivalents of (VI) in phosphorous oxychloride at 110° C. for 4 hours.

Compounds of formula (VIII) may be prepared from compounds of formula (VII) by process step (iii), which comprises reaction with a suitable aniline or 3-aminopyridine in the presence of a suitable acid, such as trifluoroacetic acid, para-toluenesulfonic acid, camphor sulfonic acid, or hydrochloric acid, in a suitable solvent such as xylene, which is heated at 150° C. Typical conditions comprise heating 1 equivalent of 1,2,4-oxadiazole (VII), 3 equivalents of aniline/ aminopyridine and 0.04-0.1 equivalents of para-toluenesulfonic acid in xylene at 150° C. for 18-22 hours.

Compounds of formula (I) may be prepared from compounds of formula (VIII) by process step (iv), which comprises a Suzuki coupling reaction as described in scheme 1.

Compounds of general formula (I) where $R^2$ is $NR^7R^8$ or a 5-7 membered N-linked heterocycle as described herein, $R^3$ is H and where $R^1$, $R^4$, $R^5$, $R^6$, $R^7$, $R^8$, X, V, W, Y and Z are as described herein may be prepared according to reaction scheme 3.

Scheme 3

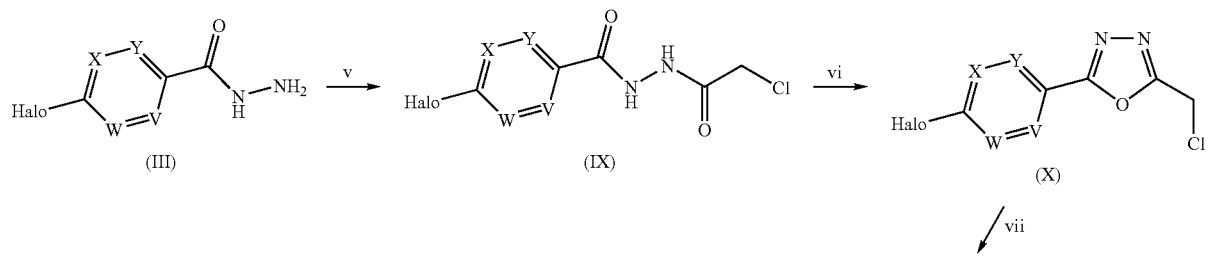

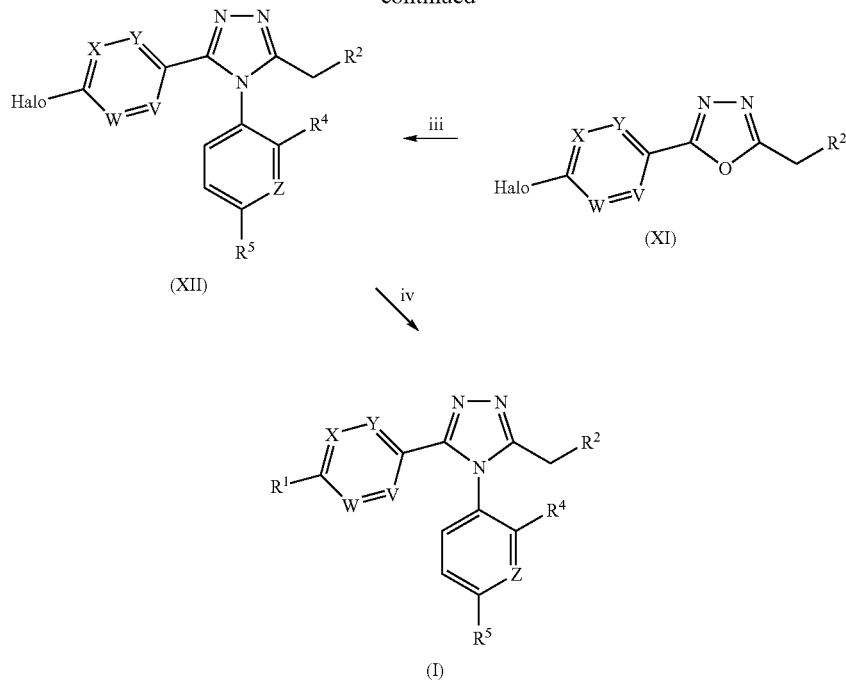

halo = Cl or Br

Compounds of formula (IX) can be prepared from aryl hydrazides of formula (III) by process step (v), which comprises reaction with a suitable acid chloride, such as chloroacetyl chloride, in the presence of a base, such as triethylamine, N-methyl morpholine, sodium carbonate or potassium hydroxide. Typical conditions comprise reacting 1.0 equivalents of aryl hydrazide (III), 1.0-1.3 equivalents of chloroacetyl chloride, 1.2-2.0 equivalents of N-methyl morpholine in dichloromethane at 25° C.

Compounds of formula (X) can be prepared from compounds of formula (IX) by process step (vi), which comprises reaction with a suitable dehydrating agent such as phosphorous oxychloride, trifluoromethanesulfonic anhydride, or phosphorous pentachloride between a temperature of 25° C. and 110° C. Typical conditions comprise heating 1.0 equivalent of compound (IX) in phosphorous oxychloride at 110° C. for 4 hours.

Compounds of formula (XI) can be prepared from alkyl chlorides of formula (X) by process step (vii), which comprises reaction with a suitable primary or secondary amine (HNR$^7$R$^8$) or a 5-7 membered N-linked heterocycle, optionally in the presence of a base such as potassium carbonate, sodium carbonate or cesium carbonate, in a suitable solvent such as acetonitrile or N,N-dimethylformamide, by heating at 25-50° C. for 2-18 hours. Typical conditions comprise reacting 1 equivalent of alkyl chloride (X), 1.5 equivalent of amine (HNR$^7$R$^8$) or 5-7 membered N-linked heterocycle and 2 equivalents of potassium carbonate in acetonitrile for 18 hours at 25° C.

Compounds of formula (XII) may be prepared from compounds of formula (XI) by process step (iii), which comprises reaction with a suitable aniline or 3-aminopyridine, in the presence of a suitable acid, such as trifluoroacetic acid, para-toluenesulfonic acid, camphor sulfonic acid, or hydrochloric acid, in a suitable solvent such as xylene, heated at 150° C. Typical conditions comprise heating 1 equivalent of 1,2,4-oxadiazole (XI), 3 equivalents of aniline/aminopyridine and 0.04-0.1 equivalents of para-toluenesulfonic acid in xylene at 150° C. for 18-24 hours.

Compounds of formula (I) may be prepared from compounds of formula (XII) by process step (iv), which comprises reaction with a suitable boronic acid such as 2,3-dimethylphenyl boronic acid (commercially available), in a suitable solvent, in the presence of a suitable base and palladium catalyst as described in scheme 1.

Compounds of general formula (I) where R$^1$, R$^2$, R$^3$, R$^4$, R$^5$, R$^6$, X, V, W, Y and Z are as described herein may alternatively be prepared according to reaction scheme 4.

Scheme 4

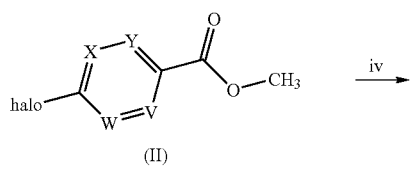

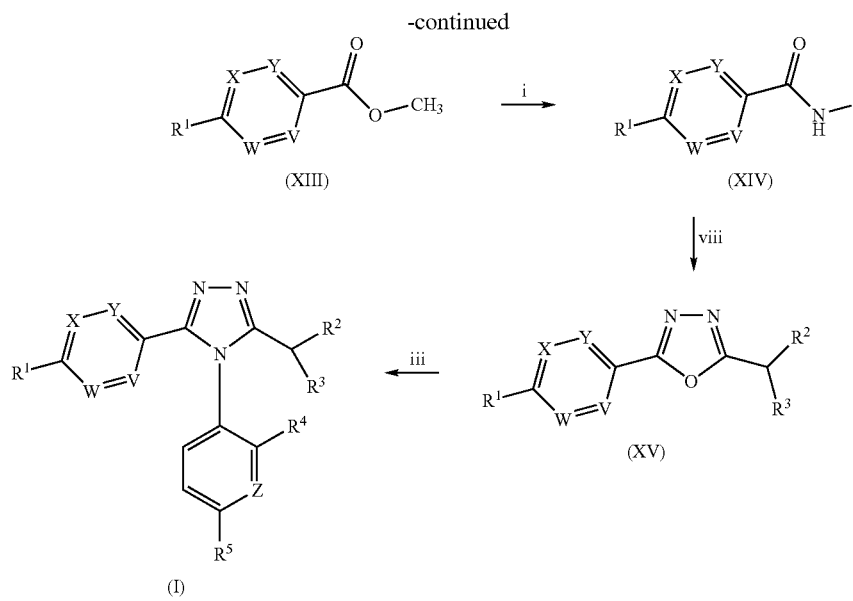

Compounds of formula (II) are prepared as described in scheme 1.

Compounds of general formula (XIII) can be prepared from compounds of general formula (II) by process step (iv) as described in scheme 1.

Compounds of general formula (XIV) can be prepared from compounds of general formula (XIII) by process step (i) as described in scheme 1.

When $R^2$=H, compounds of general formula (XV) can be prepared from compounds of general formula (XIV) by process step (viii), using a method analogous to process step (ii), as described in scheme 1.

When $R^2 \neq H$, compounds of general formula (XV) can be prepared from compounds of general formula (XIV) by process step (viii), using methods analogous to steps (v) and (vi), as described in scheme 2 or steps (v), (vi) and (vii) as described in scheme 3.

Compounds of general formula (I) can be prepared from compounds of general formula (XV) by process step (iii), as described in scheme 1.

Compounds of general formula (I) where X is C—$R^6$, $R^3$ is H and where $R^1$, $R^2$, $R^4$, $R^5$, $R^6$, V, W, Y and Z are as described herein may alternatively be prepared according to reaction scheme 5.

Scheme 5

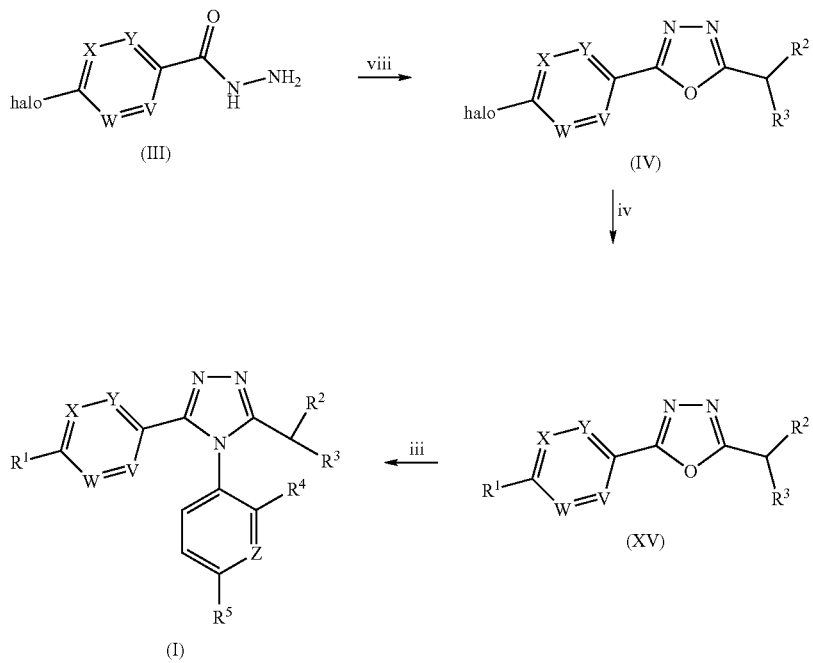

Compounds of formula (III) are prepared as described in scheme 1.

When R²=H, compounds of general formula (IV) can be prepared from compounds of general formula (III) by process step (viii), using a method analogous to process step (ii), as described in scheme 1.

When R²≠H, compounds of general formula (IV) can be prepared from compounds of general formula (III) by process step (viii), using methods analogous to steps (v) and (vi), as described in scheme 2 and steps (v), (vi) and (vii) as described in Scheme 3.

Compounds of general formula (XV) may be prepared from compounds of general formula (IV) by process step (iv) as described in scheme 1.

Compounds of general formula (I) may be prepared from compounds of general formula (XV) by process step (iii) as described in scheme 1.

Compounds of general formula (I) and (VIII) where R¹, R², R⁴, R⁵, V, W, X, and Y are described herein and R³=H may be prepared according to reaction

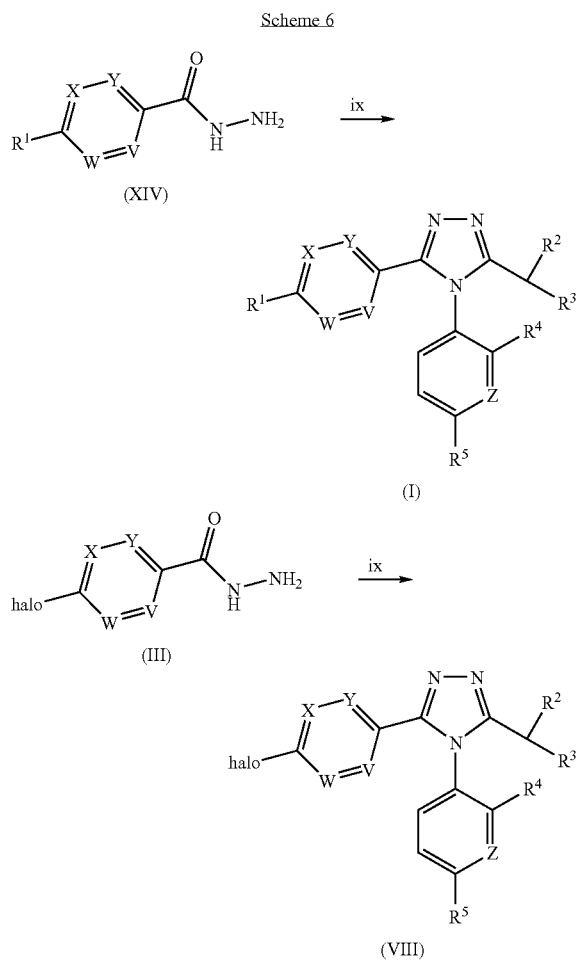

Compounds of formula (I) and (VIII) may be prepared from compounds of formula (XIV) and (III) respectively by process step (ix), which comprises sequential reaction with a dimethylacetamide dimethylacetal in a suitable solvent such as tetrahydrofuran or acetic acid heated at 55-60° C. followed by reaction with a suitable aniline or aminopyridine in the presence of a suitable acid such as acetic acid heated at 90-100° C. Typical conditions comprise heating 1.0 equivalent of acyl hydrazide, 1.5 equivalents of dimethylacetamide dimethylacetal (Aldrich) in THF at 55° C. for 2 hours followed by the addition of 1.5 equivalents of 2-methoxy-5-aminopyridine (Aldrich) and heating in acetic acid at 90° C. for 5 hours.

All of the above reactions and the preparations of novel starting materials disclosed in the preceding methods are conventional and appropriate reagents and reaction conditions for their performance or preparation as well as procedures for isolating the desired products will be well-known to those skilled in the art with reference to literature precedents and the Examples and Preparations hereto.

Utility

The compounds of the invention are useful because they have pharmacological activity in mammals, including humans. More particularly, they are useful in the treatment or prevention of a disorder in which modulation of the levels of oxytocin could provide a beneficial effect. Disease states that may be mentioned include sexual dysfunction, particularly premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, ocular hypertension, obsessive compulsive disorder and neuropsychiatric disorders.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al, *J. Urology,* 1999, 161, 5-11).

FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.,* 10, S104-S106; Berman, J. R., Berman, L. & Goldstein, I. (1999). Female sexual dysfunction: Incidence, pathophysiology, evaluations and treatment options. *Urology,* 54, 385-391). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders, Int. J. Impotence Res., 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Thus, in accordance with a further aspect of the invention, there is provided the use of a compound of the invention in the preparation of a medicament for the treatment or prophylaxis of hypoactive sexual desire disorder, sexual arousal disorder, orgasmic disorder and sexual pain disorder, more preferably for the treatment or prophylaxis of sexual arousal disorder, orgasmic disorder, and sexual pain disorder, and most preferably in the treatment or prophylaxis of sexual arousal disorder.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants eg SSRIs or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

The Diagnostic and Statistical Manual (DSM) IV of the American Psychiatric Association defines Female Sexual Arousal Disorder (FSAD) as being:

"a persistent or recurrent inability to attain or to maintain until completion of the sexual activity adequate lubrication-swelling response of sexual excitement. The disturbance must cause marked distress or interpersonal difficulty."

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post menopausal (±HRT) women. It is associated with concomitant disorders such as depression, cardiovascular diseases, diabetes and UG disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

Male sexual dysfunction (MSD) is generally associated with either erectile dysfunction, also known as male erectile dysfunction (MED) and/or ejaculatory disorders such as premature ejaculation, anorgasmia (unable to achieve orgasm) or desire disorders such as hypoactive sexual desire disorder (lack of interest in sex).

PE is a relatively common sexual dysfunction in men. It has been defined in several different ways but the most widely accepted is the Diagnostic and Statistical Manual of Mental Disorders IV one which states:

"PE is a lifelong persistent or recurrent ejaculation with minimal sexual stimulation before, upon or shortly after penetration and before the patient wishes it. The clinician must take into account factors that affect duration of the excitement phase, such as age, novelty of the sexual partner or stimulation, and frequency of sexual activity. The disturbance causes marked distress of interpersonal difficulty."

The International Classification of Diseases 10 definition states:

"There is an inability to delay ejaculation sufficiently to enjoy lovemaking, manifest as either of the following: (1) occurrence of ejaculation before or very soon after the beginning of intercourse (if a time limit is required: before or within 15 seconds of the beginning of intercourse); (2) ejaculation occurs in the absence of sufficient erection to make intercourse possible. The problem is not the result of prolonged abstinence from sexual activity"

Other definitions which have been used include classification on the following criteria:

Related to partner's orgasm

Duration between penetration and ejaculation

Number of thrust and capacity for voluntary control

Psychological factors may be involved in PE, with relationship problems, anxiety, depression, prior sexual failure all playing a role.

Ejaculation is dependent on the sympathetic and parasympathetic nervous systems. Efferent impulses via the sympathetic nervous system to the vas deferens and the epididymis produce smooth muscle contraction, moving sperm into the posterior urethra. Similar contractions of the seminal vesicles, prostatic glands and the bulbouretheral glands increase the volume and fluid content of semen. Expulsion of semen is mediated by efferent impulses originating from a population of lumber spinothalamic cells in the lumbosacral spinal cord (Coolen & Truitt, *Science,* 2002, 297, 1566) which pass via the parasympathetic nervous system and cause rhythmic contractions of the bulbocavernous, ischiocavernous and pelvic floor muscles. Cortical control of ejaculation is still under debate in humans. In the rat the medial pre-optic area and the paraventricular nucleus of the hypothalamus seem to be involved in ejaculation.

Ejaculation comprises two separate components—emission and ejaculation. Emission is the deposition of seminal fluid and sperm from the distal epididymis, vas deferens, seminal vesicles and prostrate into the prostatic urethra. Subsequent to this deposition is the forcible expulsion of the seminal contents from the urethral meatus. Ejaculation is distinct from orgasm, which is purely a cerebral event. Often the two processes are coincidental.

A pulse of oxytocin in peripheral serum accompanies ejaculation in mammals. In man oxytocin but not vasopressin plasma concentrations are significantly raised at or around ejaculation. Oxytocin does not induce ejaculation itself; this process is 100% under nervous control via $\alpha 1$-adrenoceptor/sympathetic nerves originating from the lumbar region of the spinal cord. The systemic pulse of oxytocin may have a role in the peripheral ejaculatory response. It could serve to modulate the contraction of ducts and glandular lobules throughout the male genital tract, thus influencing the fluid volume of different ejaculate components for example. Oxytocin released centrally into the brain could influence sexual behaviour, subjective appreciation of arousal (orgasm) and latency to subsequent ejaculation.

Accordingly, one aspect of the invention provides for the use of a compound of formula (I), without the proviso, in the preparation of a medicament for the prevention or treatment of sexual dysfunction, preferably male sexual dysfunction, most preferably premature ejaculation.

It has been demonstrated in the scientific literature that the number of oxytocin receptors in the uterus increases during pregnancy, most markedly before the onset of labour (Gimpl & Fahrenholz, 2001, *Physiological Reviews,* 81 (2), 629-683). Without being bound by any theory it is known that the inhibition of oxytocin can assist in preventing preterm labour and in resolving complications in labour.

Accordingly, another aspect of the invention provides for the use of a compound of formula (I), without the proviso, in the preparation of a medicament for the prevention or treatment of preterm labour and complications in labour.

Oxytocin has a role in feeding; it reduces the desire to eat (Arletti et al., *Peptides,* 1989, 10, 89). By inhibiting oxytocin it is possible to increase the desire to eat. Accordingly oxytocin inhibitors are useful in treating appetite and feeding disorders.

Accordingly, a further aspect of the invention provides for the use of a compound of formula (I), without the proviso, in the preparation of a medicament for the prevention or treatment of appetite and feeding disorders.

Oxytocin is implicated as one of the causes of benign prostatic hyperplasia (BPH). Analysis of prostate tissue have shown that patients with BPH have increased levels of oxytocin (Nicholson & Jenkin, *Adv. Exp. Med. & Biol.,* 1995, 395, 529). Oxytocin antagonists can help treat this condition.

Accordingly, another aspect of the invention provides for the use of a compound of formula (I), without the proviso, in the preparation of a medicament for the prevention or treatment of benign prostatic hyperplasia.

Oxytocin has a role in the causes of dysmenorrhoea due to its activity as a uterine vasoconstrictor (Akerlund, *Ann. NY Acad. Sci.,* 1994, 734, 47). Oxytocin antagonists can have a therapeutic effect on this condition.

Accordingly, a further aspect of the invention provides for the use of a compound of formula (I), without the proviso, in the preparation of a medicament for the prevention of treatment of dysmenorrhoea.

It is to be appreciated that all references herein to treatment include curative, palliative and prophylactic treatment.

The compounds of the present invention may be coadministered with one or more agents selected from:

1) One or more selective serotonin reuptake inhibitors (SSRIs) such as dapoxetine, paroxetine, 3-[(dimethylamino)methyl]-4-[4-(methylsulfanyl)phenoxy]benzenesulfonamide (Example 28, WO 0172687), 3-[(dimethylamino)methyl]-4-[3-methyl-4-(methylsulfanyl)phenoxy]benzenesulfonamide (Example 12, WO 0218333), N-methyl-N-({3-[3-methyl-4-(methylsulfanyl)phenoxy]-4-pyridinyl}methyl)amine (Example 38, PCT Application no PCT/IB02/01032).

2) One or more local anaesthetics;

3) one or more $\alpha$-adrenergic receptor antagonists (also known as $\alpha$-adrenoceptor blockers, $\alpha$-receptor blockers or $\alpha$-blockers); suitable $\alpha_1$-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, Example 19 of WO9830560, terazosin and abanoquil; suitable $\alpha_2$-adrenergic receptor antagonists include dibenamine, tolazoline, trimazosin, efaroxan, yohimbine, idazoxan clonidine and dibenamine; suitable non-selective $\alpha$-adrenergic receptor antagonists include dapiprazole; further $\alpha$-adrenergic receptor antagonists are described in PCT application WO99/30697 published on 14 Jun. 1998 and U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference;

4) one or more cholesterol lowering agents such as statins (e.g. atorvastatin/Lipitor—trade mark) and fibrates;

5) one or more of a serotonin receptor agonist, antagonist or modulator, more particularly agonists, antagonists or modulators for example 5HT1A, 5HT2A, 5HT2C, 5HT3, 5HT6 and/or 5HT7 receptors, including those described in WO-09902159, WO-00002550 and/or WO-00028993;

6) one or more NEP inhibitors, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; IC50 values against NEP and ACE may be determined using methods described in published patent application EP1097719-A1, paragraphs [0368] to [0376];

7) one or more of an antagonist or modulator for vasopressin receptors, such as relcovaptan (SR 49059), conivaptan, atosiban, VPA-985, CL-385004, Vasotocin.

8) Apomorphine—teachings on the use of apomorphine as a pharmaceutical may be found in U.S. Pat. No. 5,945,117;

9) Dopamine agonists (in particular selective D2, selective D3, selective D4 and selective D2-like agents) such as Pramipexole (Pharmacia Upjohn compound number PNU95666), ropinirole, apomorphine, surmanirole, quinelorane, PNU-142774, bromocriptine, carbergoline, Lisuride;

10) Melanocortin receptor agonists (e.g. Melanotan II and PT141) and selective MC3 and MC4 agonists (e.g.THIQ);
11) Mono amine transport inhibitors, particularly Noradrenaline Re-uptake Inhibitors (NRIs) (e.g. Reboxetine), other Serotonin Re-uptake Inhibitors (SRIs) (e.g. paroxetine, dapoxetine) or Dopamine Re-uptake Inhibitors (DRIs);
12) 5-HT$_{1A}$ antagonists (e.g. robalzotan); and
13) PDE inhibitors such as PDE2 (e.g. erythro-9-(2-hydroxyl-3-nonyl)-adenine) and Example 100 of EP 0771799-incorporated herein by reference) and in particular a PDE5 inhibitor such as the pyrazolo[4,3-d] pyrimidin-7-ones disclosed in EP-A-0463756; the pyrazolo[4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido[3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO 99/54333; the pyrazolo[4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124; the pyrazolo[4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclosed in EP-A-1092719.

Preferred PDE5 inhibitors for use with the invention:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);

5-(2-ethoxy-5-morpholinoacetylphenyl)-1-methyl-3-n-propyl-1,6-dihydro-7H-pyrazolo[4,3-d]pyrimidin-7-one (see EP-A-0526004);

3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);

3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);

(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8;

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, *J. Med. Chem.*, 2000, 43, 1257.

Still further PDE5 inhibitors for use with the invention include:

4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5 (5-morpholinoacetyl-2-n-propoxyphenyl)-3-n-propyl-1, 6-dihydro-7H-pyrazolo(4,3-d)pyrimidin-7-one; 1-[4-[(1, 3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

The contents of the published patent applications and journal articles and in particular the general formulae of the therapeutically active compounds of the claims and exemplified compounds therein are incorporated herein in their entirety by reference thereto.

More preferred PDE5 inhibitors for use with the invention are selected from the group:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl)-pyrazino[2', 1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one or 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof.

A particularly preferred PDE5 inhibitor is 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) (also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine) and pharmaceutically acceptable salts thereof. Sildenafil citrate is a preferred salt.

Preferred agents for coadministration with the compounds of the present invention are PDE5 inhibitors, selective serotonin reuptake inhibitors (SSRIs), vasopressin $V_{1A}$ antagonists, α-adrenergic receptor antagonists, NEP inhibitors, dopamine agonists and melanocortin receptor agonists as described above. Particularly preferred agents for coadministration are PDE5 inhibitors, SSRIs, and $V_{1A}$ antagonists as described herein.

Assay

A suitable assay for determining the oxytocin antagonist activity of a compound is detailed herein below.

Oxytocin Receptor Beta-Lactamase Assay

Materials:

Cell Culture/Reagents

A: Cell Culture

Nutrient Mixture

F12 Ham's

Foetal Bovine Serum (FBS)

Geneticin

Zeocin

Trypsin/EDTA

PBS (phosphate buffered saline)

HEPES

B: Reagents

Oxytocin

OT receptor-specific antagonist

Molecular grade Dimethyl Sulphoxide (DMSO)

Trypan Blue Solution 0.4% CCF4-AM (Solution A)

Pluronic F127s (Solution B)

24% PEG, 18% TR40 (Solution C)

Probenecid (Dissolved at 200 mM in 200 mM NaOH, Solution D)

Methods

Cell Culture

Cells used are CHO-OTR/NFAT-β-Lactamase. The NFAT-β-lactamase expression construct was transfected into the CHO-OTR cell line and clonal populations were isolated via fluorescence activated cell sorting (FACS). An appropriate clone was selected to develop the assay.

Growth Medium

90% F12 Nutrient Mix, 15 mM HEPES

10% FBS 400 g/ml Geneticin 200 g/ml Zeocin 2 mM L-Glutamine

Assay Media 99.5% F12 Nutrient Mix, 15 mM HEPES 0.5% FBS

Recovery of cells—A vial of frozen cells is thawed rapidly in 37° C. water bath and the cell suspension transferred into a T225 flask with 50 ml of fresh growth medium and then incubated at 37° C., 5% $CO_2$ in an incubator until the cells adhered to the flask Replace media with 50 ml of fresh growth media the following day.

Culturing cells—CHO-OTR-NFAT-βLactamase cells were grown in growth medium. Cells were harvested when they reached 80-90% confluence removing the medium and washing with pre-warmed PBS. PBS was then removed and Trypsin/EDTA added (3 mls for T225 $cm^2$ flask) before incubating for 5 min in 37° C./5% $CO_2$ incubator. When cells were detached, pre-warmed growth media was added (7 mls for T225 $cm^2$ flask) and the cells re-suspended and mixed gently by pipetting to achieve single cell suspension. The cells were split into T225 flask at 1:10 (for 3 days growth) and 1:30 (for 5 days growth) ratio in 35 ml growth medium.

β-Lactamase Assay Method

Day 1

Cell Plate Preparation

Cells grown at 80-90% confluence were harvested and counted. Suspensions of cells at 2×105 cells/ml in growth medium were prepared and 30 μl of cells suspension added in 384-well, black clear-bottom plates. A blank plate containing diluents from each reagent was used for background subtraction.

Plates were incubated at 37° C., 5% $CO_2$ overnight.

Day 2

Cells Stimulation

10 μl antagonist/compound (diluted in assay media containing 1.25% DMSO=antagonist diluent) was added to appropriate wells and incubated for 15 minutes at 37° C., 5% $CO_2$.

10 μl oxytocin, made up in assay media, was added to all wells and incubated for 4 hours at 37° C., 5% $CO_2$.

A separate 384-well cell plate was used to generate an oxytocin dose response curve. (10 μl antagonist diluent was added to every well. 10 μl of oxytocin was then added. The cells are then treated as per antagonist/compound cell plates).

Preparation of 1 ml of 6× Loading Buffer with Enhanced Loading Protocol (This Requires Scale-Up According to Number of Plates to be Screened)

- 12 μl of solution A (1 mM CCF4-AM in Dry DMSO) was added to 60 μl of solution B (100 mg/ml Pluronic-F127 in DMSO+0.1% Acetic Acid) and vortexed.
- The resulting solution was added to 925 μl of solution C (24% w/w PEG400, 18% TR40 v/v in water).
- 75 μl of solution D was added (200 mM probenecid in 200 mM NaOH).
- 10 μl of 6× Loading Buffer was added to all wells and incubated for 1.5 hrs-2 hrs at room temperature in the dark.
- The plates were read using an LJL Analyst, Excitation 405 nm, Emission 450 nm and 530 nm, gain optimal, lagtime 0.40 μs integration, 4 flashes, bottom reading.

Using the assay described above, the compounds of the present invention all exhibit oxytocin antagonist activity, expressed as a Ki value, of less than 500 nM. Preferred examples have Ki values of less than 200 nM and particularly preferred examples have Ki values of less than 50 nM.

The compound of example 8 has a Ki value of 3 nM.

The invention is illustrated by the following non-limiting examples in which the following abbreviations and definitions are used:

| | |
|---|---|
| Arbocel ® | Filtration agent, from J. Rettenmaier & Sohne, Germany |
| APCl+ | Atmospheric Pressure Chemical Ionisation (positive scan) |
| CDCl$_3$ | Chloroform-d1 |
| d | Doublet |
| dd | Doublet of doublets |
| DMSO | Dimethylsulfoxide |
| ES+ | Electrospray ionisation positive scan. |
| eq | Equivalent |
| $^1$H NMR | Proton Nuclear Magnetic Resonance Spectroscopy |
| MS | (Low Resolution) Mass Spectroscopy |
| m | Multiplet |
| m/z | Mass spectrum peak |
| q | Quartet |
| s | Singlet |
| t | Triplet |
| δ | Chemical shift |

Preparation 1 bis[2-[(Dimethylamino-κN)methyl]phenyl-κC]bis[μ-(trifluoroacetato-κO:κO')]-palladium

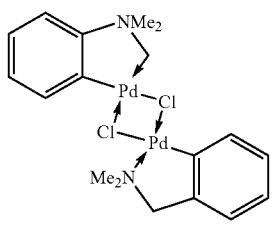

To a suspension of palladium chloride (3.43 g, 19.4 mmol) in methanol (200 mL) under nitrogen at room temperature was added N,N-dimethylbenzylamine (5.82 mL, 38.7 mmol) via syringe. The resulting red/brown suspension was stirred at room temperature for 24 hours. The now green/brown suspension was concentrated in vacuo to remove methanol, redissolved in dichloromethane (150 mL) and passed through a pad of silica gel washing through with dichloromethane. The resulting bright yellow filtrate was concentrated in vacuo and recrystallised from dichloromethane:ether to give the desired product, 4.66 g.

$^1$HNMR (CDCl$_3$, 300 MHz) δ: 2.86 (s, 6H), 2.89 (s, 6H), 3.95 (s, 4H), 6.84-7.24 (m, 8H)

Preparation 2 bis[2-[(Dimethylamino-κN)methyl]phenyl-κC]bis[μ-(trifluoroacetato-κO:κO')]-palladium

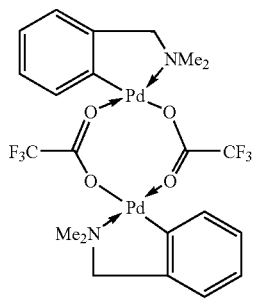

To a solution of silver trifluoroacetate (4.48 g, 20.3 mmol) in acetone (30 mL) under nitrogen at room temperature was added a solution of the complex of preparation 1 (5.60 g, 10.15 mmol) in dichloromethane (100 mL). A thick white precipitate appeared during addition. The suspension was stirred for 15 minutes, and was then filtered through a pad of silica gel, washing with dichloromethane. Concentration in vacuo gave a bright yellow powder that was recrystallised from dichloromethane:ether to give the desired product, 7.06 g.

$^1$HNMR (CDCl$_3$, 300 MHz) δ: 2.05 (s, 6H), 2.88 (s, 6H), 3.18 (d, 2H), 3.63 (d, 2H), 6.89-6.97 (m, 6H), 7.00-7.10 (m, 2H)

Preparation 3

[2-[(Dimethylamino-κN)methyl]phenyl-κC](tricyclohexylphosphine)(trifluoroacetato-κO-(SP-4-3)-palladium

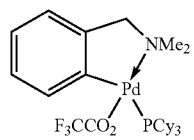

To a solution of the product of preparation 2 (6.43 g, 9.10 mmol) in dichloromethane (50 mL) under nitrogen at room temperature was added a solution of tricyclohexylphosphine (6.89 g, 24.5 mmol) in dichloromethane (20 mL). After stirring for 1 hour, the solution was passed through a plug of silica gel (7 cm×2 cm) washing with dichloromethane (400 mL), and the pale yellow filtrate concentrated in vacuo.

¹HNMR (DMSO-D₆, 400 MHz) δ: 2.20 (s, 3H), 3.81 (s, 3H), 7.07 (m, 2H), 7.28 (m, 2H), 7.34 (m, 2H), 7.56 (m, 2H). MS APCl+ m/z 344 [MH]⁺

Preparation 6

5-Bromo-pyridine-2-carboxylic acid hydrazide

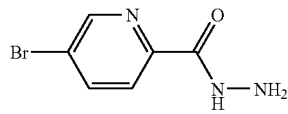

5-Bromo-pyridine-2-carboxylic acid methyl ester (J. Org. Chem., 2001, 66(2), 605-608, compound 4) (18.10 g, 83 mmol) and hydrazine monohydrate (12.5 mL, 250 mmol) were dissolved in methanol (400 mL) and the reaction mixture heated to reflux for 48 hours. The reaction mixture was then filtered and the precipitate collected dried in vacuo to yield the title product, 15.40 g.

¹HNMR (DMSO-D₆, 400 MHz) δ: 4.57 (d, 2H), 7.91 (m, 1H), 8.22 (m, 1H), 8.72 (m, 1H), 9.98 (m, 1H). MS ES+ m/z 217 [MH]⁺

Preparation 7

5-Chloro-pyrazine-2-carboxylic acid hydrazide

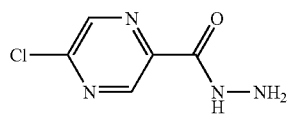

The title compound was prepared by the method of preparation 6 using 5-chloro-pyrazine-2-carboxylic acid methyl ester. 5.01 g, 50% yield of the desired product was produced.

¹HNMR (CDCl₃, 400 MHz) δ: 4.09 (d, 2H), 8.52 (s, 1H), 8.66 (bs, 1H), 9.14 (s, 1H). Microanalysis: C₅H₅ClN₄O requires: C, 34.80; H, 2.92; N, 32.47. found C, 34.89; H, 2.91; N, 32.32. MS APCl+ m/z 173 [MH]⁺

Preparation 8

5-Bromo-pyridine-2-carboxylic acid N'-(2-methoxy-acetyl)-hydrazide

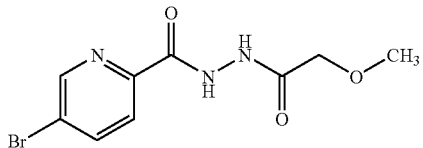

The product of preparation 6 (2.0 g, 9.3 mmol) and N-methylmorpholine (1.3 mL, 12.0 mmol) were dissolved in dichloromethane (60 mL) and the solution treated with methoxyacetyl chloride (868 μL, 9.50 mmol). The reaction mixture was stirred at room temperature for 5 hours and then washed with water and concentrated in vacuo to afford 2.41 g, 90% yield of the title product.

Recrystallisation from dichloromethane:ether gave the desired complex, 10.53 g.

¹HNMR (CDCl₃, 300 MHz) δ: 1.05-2.30 (m, 33H), 2.57 (s, 3H), 2.58 (s, 3H), 3.93 (s, 2H), 6.86-6.98 (m, 3H), 7.10-7.12 (m, 1H)

Preparation 4

2-(4-Bromo-phenyl)-5-methyl-[1,3,4]oxadiazole

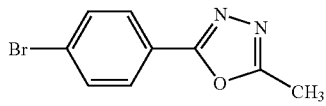

4-Bromo-benzoic acid hydrazide (12.90 g, 60 mmol) and N,N-dimethylacetamide dimethyl acetal (12 mL, 82.0 mmol) were dissolved in N,N-dimethylformamide (100 mL) and the solution heated to 60° C. for 2 hours. The solution was concentrated in vacuo and the residue taken up in toluene (80 mL) and treated with para-toluenesulfonic acid monohydrate (200 mg, 1.50 mmol). The mixture was heated to reflux for 2 hours, allowed to cool, and the product crystallised from the solution and was collected by filtration. The crude product was washed with ether and dried in vacuo to yield a white solid. The filtrate was concentrated in vacuo and the residue combined with the white solid, dissolved in toluene (50 mL) and treated with para-toluenesulfonic acid monohydrate (100 mg, 0.75 mmol). The mixture was heated to reflux for 3 hours, allowed to cool and concentrated in vacuo. The residue was purified by column chromatography on silica gel eluting with pentane:ethyl acetate 80:20 to 40:60 to yield the title product, 12.00 g.

¹HNMR (CDCl₃, 400 MHz) δ: 2.61 (s, 3H), 7.62 (d, 2H), 7.88 (d, 2H). MS ES+ m/z 239 [MH]⁺

Preparation 5

3-(4-Bromo-phenyl)-4-(4-methoxy-phenyl)-5-methyl-4H-[1,2,4]triazole

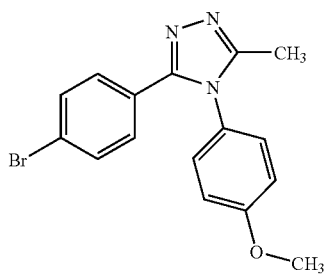

The product of preparation 4 (5.00 g, 20.9 mmol) was added to a solution of para-toluenesulfonic acid monohydrate (100 mg, 0.75 mmol) and 4-methoxyphenylamine (7.70 g, 62.5 mmol) in xylene (150 mL) and the reaction mixture heated to 150° C. for 22 hours. The reaction mixture was concentrated in vacuo and the residue taken up in dichloromethane and purified by column chromatography on silica gel eluting with dichloromethane:methanol:0.88 ammonia 100:0:0 to 97:3:0.3 to yield the title product, 7.05 g.

¹HNMR (CDCl₃, 400 MHz) δ: 3.46 (s, 3H), 4.07 (s, 2H), 7.98 (dd, 1H), 8.02 (dd, 1H), 8.61 (d, 1H), 8.89 (d, 1H), 9.95 (d, 1H). MS ES+ m/z 289 [MH]⁺

Preparation 9

6-Chloro-nicotinic acid N'-(2-methoxy-acetyl)-hydrazide

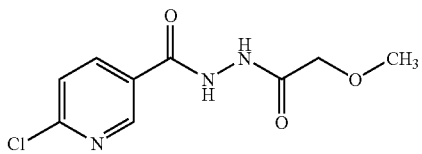

The title product was prepared by the method of preparation 8 using 6-chloronicotinic acid hydrazide. 19.0 g, 90% yield of the desired product was produced.

¹HNMR (CDCl₃, 400 MHz) δ: 3.36 (s, 3H), 3.97 (s, 2H), 7.68 (d, 1H), 8.26 (dd, 1H), 8.84 (s, 1H), 9.99 (s, 1H), 10.61 (s, 1H). MS ES+ m/z 246 [MH]⁺

Preparation 10

5-Chloro-pyrazine-2-carboxylic acid N'-(2-methoxy-acetyl)-hydrazide

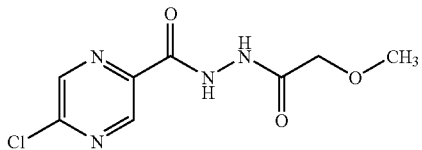

The title product was prepared by the method of preparation 8 using the hydrazide of preparation 7. 3.90 g 70% yield of the desired product was produced.

MS APCl+ m/z 245 [MH]⁺

Preparation 11

5-Chloro-pyrazine-2-carboxylic acid N'-acetyl-hydrazide

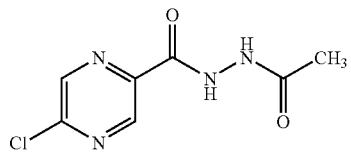

The title product was prepared by the method of preparation 8 using the hydrazide of preparation 7 and acetyl chloride. 4.0 g, 64% of the desired product was produced.

MS APCl+ m/z 215 [MH]⁺

Preparation 12

5-Bromo-pyridine-2-carboxylic acid N'-(2-chloro-acetyl)-hydrazide

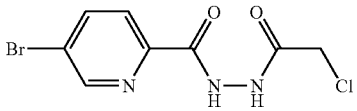

The title product was prepared by the method of preparation 8 using the hydrazide of preparation 6 and chloroacetyl chloride. 4.30 g, 59% yield of the desired product was produced.

¹HNMR (CDCl₃, 400 MHz) δ: 4.20 (s, 2H), 8.00 (d, 1H), 8.30 (d, 1H), 8.80 (s, 1H), 10.40 (s, 1H), 10.70 (s, 1H). MS APCl+ m/z 293 [MH]⁺

Preparation 13

5-Bromo-2-(5-methoxymethyl-[1,3,4]oxadiazol-2-yl)-pyridine

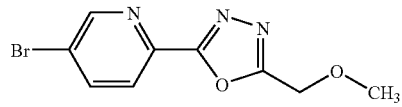

The product of preparation 8 (2.41 g, 8.4 mmol) and phosphorous oxychloride (7 mL) were combined and heated to 110° C. for 4 hours. The reaction mixture was concentrated in vacuo and the residue taken up in ethyl acetate and water. The mixture was neutralised by the addition of 10% sodium carbonate solution and the phases separated. The aqueous phase was extracted with ethyl acetate and the combined organics dried over magnesium sulfate and concentrated in vacuo. The residue was purified by column chromatography on silica gel eluting with ethyl acetate to yield the title product, 1.01 g, 45% yield.

¹HNMR (CDCl₃, 400 MHz) δ: 3.48 (s, 3H), 4.73 (s, 2H), 8.01 (dd, 1H), 8.12 (dd, 1H), 8.81 (dd, 1H). MS APCl+ m/z 272 [MH]⁺

Preparation 14

2-Chloro-5-(5-methoxymethyl-[1,3,4]oxadiazol-2-yl)-pyridine

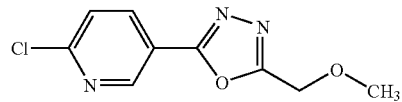

The title compound was prepared by the method of preparation 13 using the product of preparation 9 provide 7.93 g, 40% yield of title compound as a rust brown solid.

¹HNMR (CDCl₃, 400 MHz) δ: 3.52 (s, 3H), 4.74 (s, 2H), 7.50 (d, 1H), 8.32 (dd, 1H), 9.06 (d, 1H). Microanalysis: C₉H₈ClN₃O₂ requires: C, 47.91; H, 3.57; N, 18.62. found C, 47.75; H, 3.50; N, 18.46. MS APCl+ m/z 226 [MH]⁺.

Preparation 15

2-Chloro-5-(5-methoxymethyl-[1,3,4]oxadiazol-2-yl)-pyrazine

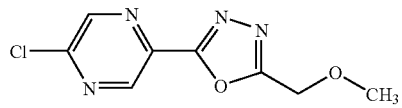

The title compound was prepared by the method of preparation 13 using the product of preparation 10. 1.38 g, 38% yield of the desired product was produced as a light brown solid.

$^1$HNMR (CDCl$_3$, 400 MHz) δ: 3.52 (s, 3H), 4.78 (s, 2H), 8.75 (s, 1H), 9.25 (s, 1H) MS APCl+ m/z 227 [MH]$^+$

Preparation 16

2-Chloro-5-(5-methyl-[1,3,4]oxadiazol-2-yl)-pyrazine

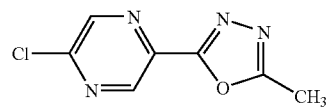

The title compound was prepared by the method of preparation 13 using the product of preparation 11. 30 g, 35% of the desired product was produced as a brown solid.

$^1$HNMR (CDCl$_3$, 400 MHz) δ: 2.68 (s, 3H), 8.71 (s, 1H), 9.22 (s, 1H) MS APCl+ m/z 197 [MH]$^+$

Preparation 17

5-Bromo-2-(5-chloromethyl-[1,3,4]oxadiazol-2-yl)-pyridine

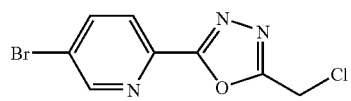

The title compound was prepared by the method of preparation 13 using the product of preparation 12. 2.3 g 57% yield of desired product, was obtained as an off white solid.

$^1$HNMR (DMSO-D$_6$, 400 MHz) δ: 4.80 (s, 2H), 8.05 (d, 1H), 8.15 (d, 1H), 8.85 (s, 1H). MS APCl+ m/z 276 [MH]$^+$

Preparation 18

5-Bromo-2-[5-(methoxymethyl)-4-(6-methoxypyridin-3-yl)-4H-1,2,4-triazol-3-yl]pyridine

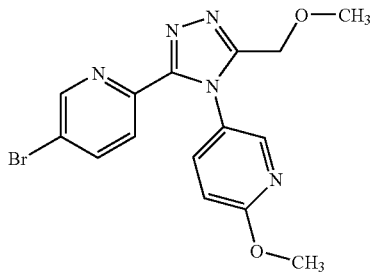

The product of preparation 13 (1.01 g, 3.74 mmol), 5-amino-2-methoxypyridine (1.40 g, 11.3 mmol) and para-toluenesulfonic acid monohydrate (50 mg, 0.37 mmol) were dissolved in xylene (25 mL) and the reaction mixture heated to 150° C. for 23 hours. The reaction mixture was concentrated in vacuo and the residue purified by column chromatography on silica gel eluting with dichloromethane:methanol 100:0 to 90:10 to yield the title product, 1.0 g, 72% yield as a purple gum.

$^1$HNMR (CDCl$_3$, 400 MHz) δ: 3.32 (s, 3H), 3.99 (s, 3H), 4.46 (s, 2H), 6.82 (d, 1H), 7.54 (dd, 1H), 7.90 (dd, 1H), 8.05 (d, 1H), 8.13 (d, 1H), 8.37 (d, 1H). MS ES+ m/z 398 [MH]$^+$

Preparation 19

2-(4-Fluoro-2-methyl-phenyl)-5-(5-methoxymethyl-[1,3,4]oxadiazol-2-yl)-pyridine

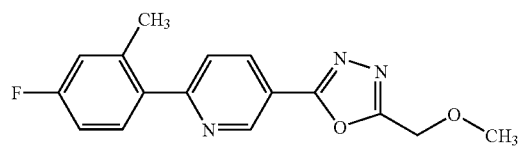

The chloro compound of preparation 14 (500 mg, 2.22 mmol), 4-fluoro-2-methylphenyl boronic acid (361 mg, 2.65 mmol), the palladium complex of preparation 3 (10 mg, cat.) and caesium carbonate (2.16 g, 6.66 mmol) were dissolved in 1,4-dioxan (10 mL) and the reaction mixture heated to reflux for 2 hours. Additional palladium complex (10 mg) was added and the reaction mixture refluxed for a further 1 hour. The reaction mixture was concentrated in vacuo and the residue taken up in ethyl acetate and water. The phases were separated and the ethyl acetate phase washed with brine, dried over magnesium sulfate and concentrated in vacuo to yield the title product, 690 mg in quantitative yield.

MS APCl+ m/z 300 [MH]$^+$

Preparation 20

2-(2,3-Dimethyl-phenyl)-5-(5-methoxymethyl-[1,3,4]oxadiazol-2-yl)-pyridine

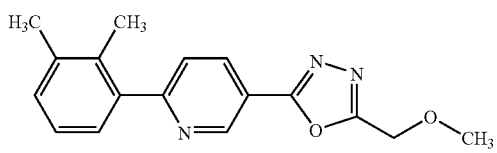

The title product was prepared by the method of preparation 19 using 2,3-dimethylphenyl boronic acid (399 mg, 1.2 eq) and the product of preparation 14 (500 mg, 2.22 mmol). 712 mg, quantitative yield, of the desired product was produced.

MS APCl+ m/z 296 [MH]+

Preparation 21

2-(2,3-Dimethyl-phenyl)-5-(5-methoxymethyl-[1,3,4]oxadiazol-2-yl)-pyrazine

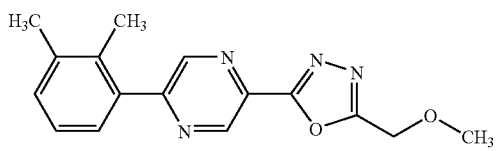

The title product was prepared by the method of preparation 19 using 2,3-dimethylphenyl boronic acid and the chloro compound of preparation 15. 466 mg, quantitative yield, of the desired product was produced.

$^1$HNMR (CDCl$_3$, 400 MHz) δ: 2.29 (s, 3H), 2.39 (s, 3H), 3.52 (s, 3H), 4.78 (s, 2H), 7.23-7.37 (m, 3H), 8.84 (s, 1H), 9.54 (s, 1H) MS APCl+ m/z 297[MH]+

Preparation 22

2-(4-Fluoro-2-methyl-phenyl)-5-(5-methoxymethyl-[1,3,4]oxadiazol-2-yl)-pyrazine

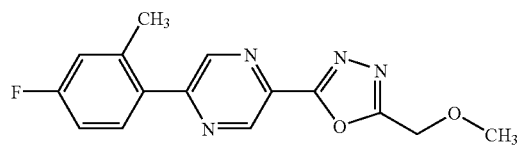

The title product was prepared by the method of preparation 19 using 4-fluoro-2-methyl-phenyl boronic acid and the chloro compound of preparation 15. 450 mg, 97% of the desired product was produced.

MS APCl+ m/z 301 [MH]+

Preparation 23

2-(2,3-Dimethyl-phenyl)-5-(5-methyl-[1,3,4]oxadiazol-2-yl)-pyrazine

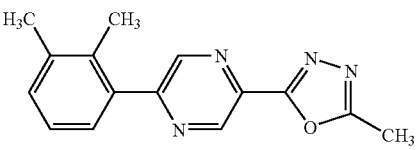

The title product was prepared by the method of preparation 19 using 2,3-dimethylphenyl boronic acid and the chloro compound of preparation 16. 404 mg, quantitative yield, of the desired product was produced.

MS APCl+ m/z 267 [MH]+

Preparation 24

2-(4-Fluoro-2-methyl-phenyl)-5-(5-methyl-[1,3,4]oxadiazol-2-yl)-pyrazine

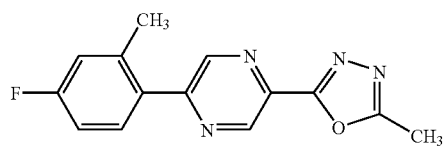

The title product was prepared by the method of preparation 19 using 4-fluoro-2-methyl-phenyl boronic acid and the chloro compound of preparation 16. 377 mg, quantitative yield, of the desired product was produced.

MS APCl+ m/z 271 [MH]+

Preparation 25

1-[5-(5-Bromo-pyridin-2-yl)-[1,3,4]oxadiazol-2-ylmethyl]-pyrrolidine-(2S)-2-carboxylic acid amide

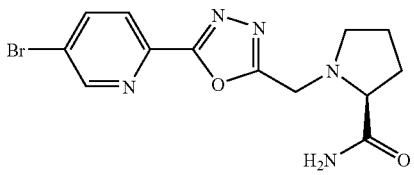

The chloro compound of preparation 17 (500 mg, 1.82 mmol) and (S)-prolinamide (312 mg, 2.73 mmol) were dissolved in acetonitrile (10 mL) and the mixture treated with potassium carbonate (503 mg, 3.64 mmol). The reaction mixture was stirred at room temperature for 18 hours and then at 50° C. for 2 hours. The reaction mixture was concentrated in vacuo and the residue partitioned between ethyl acetate and water. The precipitate formed was filtered off and the organic layer of the filtrate washed with water, 1M sodium hydroxide solution and brine. The organic layer was then concentrated in vacuo to yield the title product, 540 mg, 84% yield.

¹HNMR (DMSO-D₆, 400 MHz) δ: 1.70 (m, 3H), 2.00 (m, 1H), 2.60 (m, 1H), 3.10 (m, 1H), 3.20 (m, 1H), 4.00 (d, 1H), 4.20 (d, 1H), 7.00-7.20 (d, 2H), 8.10 (d, 1H), 8.30 (d, 1H), 8.90 (s, 1H).

Preparation 26

5-Bromo-2-(5-pyrrolidin-1-ylmethyl-[1,3,4]oxadiazol-2-yl)-pyridine

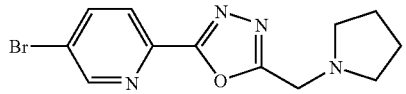

Pyrrolidine (324 mg, 0.38 mL, 4.56 mmol) was added to a stirred solution of the chloro compound of preparation 17 (500 mg, 1.82 mmol) in acetonitrile (15 mL) at room temperature. After stirring for 18 hours the reaction mixture was concentrated in vacuo and the residue taken up in ethyl acetate (50 mL) and washed with 2M aqueous sodium hydroxide, followed by water followed by brine. The organic phase was dried over sodium sulfate, filtered and concentrated in vacuo to afford 407 mg, 72% yield of the title compound.

¹HNMR (CDCl₃, 400 MHz) δ: 1.90 (m, 4H), 2.70 (m, 4H), 4.00 (s, 2H), 8.00 (d, 1H), 8.20 (d, 1H), 8.80 (s, 1H).

Preparation 27

1-[5-(5-Bromo-pyridin-2-yl)-4-(6-methoxy-pyridin-3-yl)-4H-[1,2,4]triazol-3-ylmethyl]-pyrrolidine-(2S)-2-carboxylic acid amide

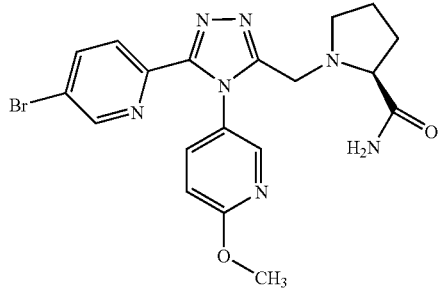

The product of preparation 25 (500 mg, 1.20 mmol) and 5-amino-2-methoxypyridine (224 mg, 1.81 mmol) were dissolved in xylene (15 mL) and the solution treated with catalytic para-toluenesulfonic acid monohydrate and heated to reflux for 18 hours. The reaction mixture was concentrated in vacuo and the residue taken up in ethyl acetate and washed with water, 2M citric acid solution, 2M sodium hydroxide solution, dried over magnesium sulfate and concentrated in vacuo. The residue was purified by column chromatography on silica gel eluting with dichloromethane:methanol 100:0 to 95:5 to yield the title product, 252 mg, 46% yield.

¹HNMR (CDCl₃, 400 MHz) δ: 1.80 (m, 2H), 2.20 (m, 1H), 2.60 (m, 1H), 3.10 (m, 1H), 3.20 (m, 1H), 3.90 (m, 2H), 4.00 (s, 3H), 5.00 (s, 1H), 6.70 (s, 1H), 6.90 (d, 1H), 7.90 (d, 1H), 8.05 (d, 1H), 8.20 (d, 1H), 8.40 (s, 1H). MS ES+ m/z 458 [MH]⁺

Preparation 28

5-Bromo-2-(((5-pyrrolidin-1-ylmethyl)-4-(6-methoxypyridin-3-yl))-4H-[1,2,4]triazol-3-yl)-pyridine

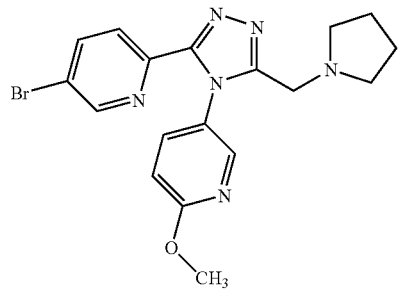

412 mg, 77% yield of the title compound was prepared by the method of preparation 27 using the product of preparation 26.

MS ES+ m/z 417 [MH]⁺

Preparation 29

3-Methyl-4-(4,4,5,5-tetramethyl-[1,3,2]dioxaborolan-2-yl)-benzonitrile

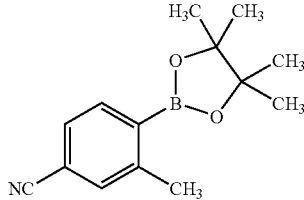

Palladium (II) acetate (224 mg, 5 mol %), potassium acetate (3.68 g, 61.2 mmol) and bis(pinacolato)diboron (5.4 g, 21.4 mmol) were added to a solution of 1-bromo-4-cyano-2-methylbenzene (4.0 g, 20.4 mmol) in N,N-dimethylformamide (40 mL) and heated at 80° C. for 18 hours. After such time the mixture was cooled and filtered through a pad of Celite®, washing with ethyl acetate and water. The organic phase was separated, dried over sodium sulfate and concentrated in vacuo to afford a brown solid. The solid was purified by trituration in pentane, filtration and drying to afford the title compound as a beige solid (2.68 g, 54% yield).

¹HNMR (CDCl₃, 400 MHz) δ: 1.35 (s, 12H), 2.55 (s, 3H), 7.41-7.45 (m, 2H), 7.82 (d, 1H). MS APCI+ m/z 261 [MNH₄]⁺

Preparation 30

2-Chloro-5-[4-(6-methoxy-pyridin-3-yl)-5-methyl-4H-[1,2,4]triazol-3-yl]-pyrazine

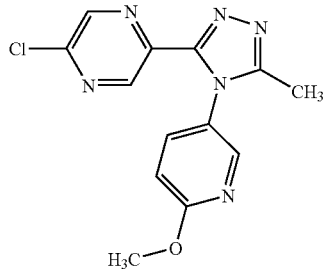

The title product was prepared by the method of preparation 18 using the oxadiazole compound of preparation 16 and 5-amino-2-methoxypyridine. 4.3 g, 44% yield of the desired product was produced as a beige solid.

$^1$HNMR (CDCl$_3$, 400 MHz) δ: 2.36 (s, 3H), 3.99 (s, 3H), 6.86 (d, 1H), 7.45 (dd, 1H), 8.02 (d, 1H), 8.27 (d, 1H), 9.23 (d, 1H).

Preparation 31

2-Chloro-5-[5-methoxymethyl-4-(6-methoxy-pyridin-3-yl)-4H-[1,2,4]triazol-3-yl]-pyrazine

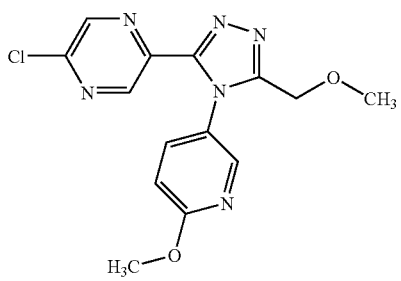

The title product was prepared by the method of preparation 18 using the oxadiazole compound of preparation 15 and 5-amino-2-methoxypyridine. 10.5 g, 59% yield of the desired product was produced as a beige solid.

$^1$HNMR (CDCl$_3$, 400 MHz) δ: 3.33 (s, 3H), 3.99 (s, 3H), 4.47 (s, 2H), 6.83 (d, 1H), 7.53 (dd, 1H), 8.06 (d, 1H), 8.30 (d, 1H), 9.25 (d, 1H). MS APCl+ m/z 333 [MH]$^+$

Preparation 32

2-(5-Fluoro-2-methoxy-phenyl)-5-(5-methoxymethyl-[1,3,4]oxadiazol-2-yl)-pyridine

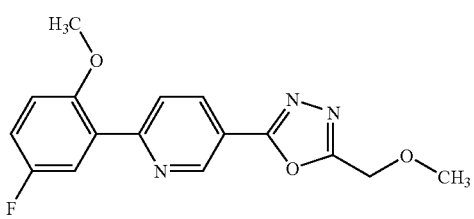

The title product was prepared by the method of preparation 19 using 5-fluoro-2-methoxy-phenyl boronic acid (565 mg, 3.33 mol) and the chloro compound from preparation 14 (500 mg, 2.22 mmol). 669 mg, 96% yield of the desired product was produced.

$^1$HNMR (CDCl$_3$, 400 MHz) δ: 3.51 (s, 3H), 3.88 (s, 3H), 4.75 (s, 2H), 6.97 (d, 1H), 7.11 (m, 1H), 7.70 (dd, 1H), 8.11 (d, 1H), 8.37 (dd, 1H), 9.34 (d, 1H). MS APCl+ m/z 316 [MH]$^+$

Preparation 33

6-Chloro-nicotinic acid N'-(2-chloro-acetyl)-hydrazide

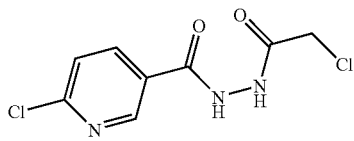

Chloroacetyl chloride (2.8 mL, 34.9 mmol) was added dropwise to an ice-cooled solution of 6-chloronicotinic acid hydrazide (5 g, 29.1 mmol) and 4-methylmorpholine (4.8 mL, 43.7 mmol) in dichloromethane (100 mL) and the reaction was stirred at room temperature for 3 hours. The resulting precipitate was then filtered off, slurried with dichloromethane, re-filtered, washed with dichloromethane (×3) and dried to afford the title compound as a beige solid in 57% yield, 4.1 g $^1$HNMR (DMSO-D$_6$, 400 MHz) δ: 4.20 (s, 2H), 7.68 (d, 1H), 8.23 (d, 1H), 8.84 (m, 1H), 10.50 (s, 1H), 10.83 (s, 1H). MS APCl+ m/z 248/250 [MH]$^+$

Preparation 34

5-Chloro-pyrazine-2-carboxylic acid N'-(2-chloro-acetyl)-hydrazide

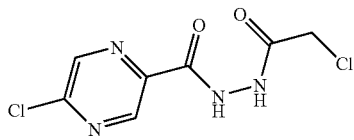

The title product was prepared from the product of preparation 7 and chloroacetylchloride, using the method of preparation 33, as a solid in 37% yield.

MS APCl+ m/z 249/251 [MH]$^+$

Preparation 35

6-Chloro-nicotinic acid N'-acetyl-hydrazide

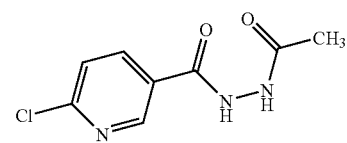

The title compound was prepared from 6-chloronicotinic acid hydrazide and acetyl chloride, using the method of preparation 33, as a white solid in 64% yield.

$^1$HNMR (DMSO-D$_6$, 400 MHz) δ: 1.91 (s, 3H), 7.68 (d, 1H), 8.24 (dd, 1H), 8.82 (d, 1H), 10.00 (s, 1H), 10.58 (s, 1H). MS APCl+ m/z 214 [MH]$^+$

Preparation 36

6-Chloro-nicotinic acid N'-[2-(2-methoxy-ethoxy)-acetyl]-hydrazide

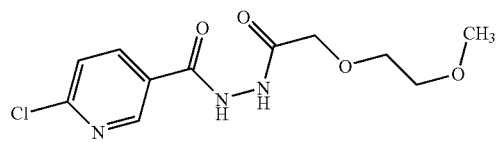

(2-Methoxy-ethoxy)-acetyl chloride (2.13 g, 13.99 mmol) was added to an ice-cold solution of 6-chloronicotinic acid hydrazide (2 g, 11.66 mmol) and N-methylmorpholine (1.92 mL, 17.49 mmol) in dichloromethane (60 mL) and the mixture was stirred at room temperature for 18 hours. The mixture was then treated with sodium hydrogen carbonate solution and concentrated in vacuo. The aqueous residue was extracted with dichloromethane (×2) and the combined organic solutions were washed with brine and dried over sodium sulfate and concentrated in vacuo to give a pale yellow residue. The residue was then stirred in diethyl ether for 2 hours, filtered and dried to afford the title compound as a pale yellow solid in 51% yield, 1.7 g.

$^1$HNMR (CDCl$_3$, 400 MHz) δ: 3.46 (s, 3H), 3.62 (m, 2H), 3.78 (m, 2H), 4.21 (s, 2H), 7.42 (d, 1H), 8.07 (dd, 1H), 8.82 (d, 1H) 9.28 (brs, 1H), 9.83 (brs, 1H). MS APCl+ m/z 288 [MH]$^+$ Preparation 37

6-Chloro-nicotinic acid N'-(2-ethoxy-acetyl)-hydrazide

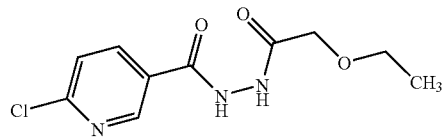

(2-Ethoxy)-acetyl chloride [(1.72 g, 13.99 mmol), Tett. Lett., 35, (39), 7269; 1994)] was added to an ice-cold solution of 6-chloronicotinic acid hydrazide (2 g, 11.66 mmol) and N-methylmorpholine (1.92 mL, 17.49 mmol) in dichloromethane (60 mL) and the mixture was stirred at room temperature for 18 hours. The mixture was then washed with citric acid, sodium hydrogen carbonate solution and brine and the solvent was evaporated under reduced pressure to yield some title product as a white solid, 880 mg. The combined aqueous washings were extracted with ethyl acetate (×2) and the combined organic solutions were dried over sodium sulfate and concentrated in vacuo to afford a further crop of title compound as a pale yellow solid, 1.6 g (total yield of 83%).

$^1$HNMR (CDCl$_3$, 400 MHz) δ: 1.21 (t, 3H), 3.55 (q, 2H), 4.06 (s, 2H), 7.38 (d, 1H), 8.00 (dd, 1H), 8.77 (d, 1H) 8.99 (brs, 1H), 9.15 (brs, 1H). MS APCl+ m/z 258/260 [MH]$^+$ Preparations 38 to 42

The following compounds, of the general formula shown below, were prepared by the method of preparation 13 using the appropriate hydrazide (preparations 33-37) and phosphorus oxychloride.

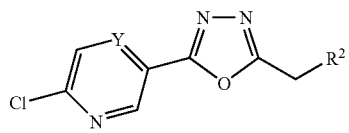

| No. | R$^2$ | Y | Data | Yield |
|---|---|---|---|---|
| 38 | Cl | CH | $^1$HNMR(CDCl$_3$, 400 MHz) δ: 4.80(s, 2H), 7.52(d, 1H), 8.35(dd, 1H), 9.08(d, 1H). MS APCl+ m/z 230/232 [MH]$^+$ | 55% |

-continued

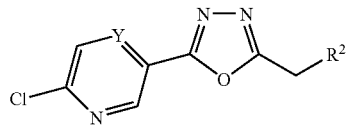

| No. | R² | Y | Data | Yield |
|---|---|---|---|---|
| 39 | Cl | N | ¹HNMR(CDCl₃, 400 MHz) δ: 4.83(s, 2H), 8.76(s, 1H), 9.36(s, 1H). MS APCl+ m/z 231/233 [MH]⁺ | 38% |
| 40 | H | CH | ¹HNMR(CDCl₃, 400 MHz) δ: 2.66(s, 3H), 7.51(d, 1H), 8.31(d, 1H), 9.02(s, 1H). Microanalysis: C₈H₆ClN₃O 0.25 H₂O requires: C 48.02; H 3.27; N 21.00; found C 47.89; H 3.23, N 20.95. | 77% |
| 41 | H₃C−O−CH₂CH₂−O− | CH | ¹HNMR(CDCl₃, 400 MHz) δ: 3.39(s, 3H), 3.59-3.61(m, 2H), 3.78-3.80(m, 2H), 4.86(5, 2H), 7.52(d, 1H), 8.33(dd, 1H), 9.07(d, 1H). MS APCl+ m/z 270/272 [MH]⁺ | 68% |
| 42 | H₃C−CH₂−O− | CH | ¹HNMR(CDCl₃, 400 MHz) δ: 1.28(t, 3H), 3.69(q, 2H), 4.77(s, 2H), 7.49(d, 1H), 8.34(dd, 1H), 9.07(d, 1H). MS ES+ m/z 262 [MNa]⁺ | 75% |

Preparation 42 was purified by column chromatography on silica gel, eluting with pentane:ethyl acetate, 100:0 to 90:10.

Preparation 43

2-Chloro-5-(5-[1,2,3]triazol-2-ylmethyl-[1,3,4]oxa-diazol-2-yl)-pyridine

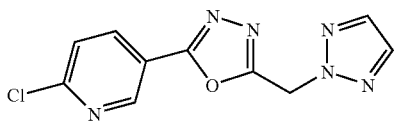

1H-1,2,3-Triazole (264 mg, 3.85 mmol) was added to a suspension of the chloro compound of preparation 38 (800 mg, 3.5 mmol), and potassium carbonate (1.4 g, 7 mmol) in N,N-dimethylformamide (15 mL) and the mixture stirred at room temperature for 18 hours. The reaction mixture was then partitioned between ethyl acetate and water and the organic layer was separated, washed with brine, dried over sodium sulfate and concentrated in vacuo to afford the title compound as a yellow solid in 71% yield, 650 mg.

¹HNMR (CDCl₃, 400 MHz) δ: 6.08 (s, 2H), 7.66 (d, 1H), 7.80 (s, 2H), 8.38 (dd, 1H), 8.99 (d, 1H). MS APCl+ m/z 263 [MH]⁺

Preparations 44 to 45

The following compounds, of the general formula shown below, were prepared from the product of preparations 38 and 39 using the method of preparation 43.

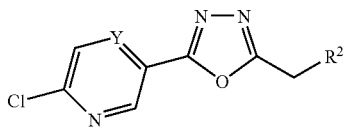

| No. | R² | Y | Data | Yield |
|---|---|---|---|---|
| 44 | pyrazolyl | N | MS APCl+ m/z 264 [MH]⁺ | 40% |
| 45 | (H₃C)₂N− | CH | ¹HNMR(CDCl₃, 400 MHz) δ: 2.34(s, 6H), 3.78(s, 2H), 7.43(d, 1H), 8.28(dd, 1H), 9.01(d, 1H). MS APCl+ m/z 239/241 [MH]⁺ | 82% |

Preparations 46 to 52

The following compounds, of the general formula shown below, were prepared by the method of preparation 18 using the appropriate oxadiazole (preparations 14 and 40-45) and 5-amino-2-methoxypyridine.

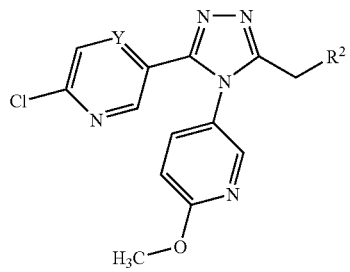

| No. | R² | Y | Data | Yield |
|---|---|---|---|---|
| 46 | (2H-1,2,3-triazol-2-yl)methyl | CH | ¹HNMR(CDCl₃, 400 MHz) δ: 3.97(s, 3H), 5.75(s, 2H), 6.78(d, 1H), 7.24(d, 1H), 7.34(d, 1H), 7.56(s, 2H), 7.90(dd, 1H), 7.94(m, 1H), 8.30(d, 1H)<br>MS APCI+ m/z 369 [MH]⁺ | 25% |
| 47 | (2H-1,2,3-triazol-2-yl)methyl | N | MS APCI+ m/z 370 [MH]⁺ | 29% |
| 48 | (CH₃)₂N– | CH | ¹HNMR(CDCl₃, 400 MHz) δ: 2.25(s, 6H), 3.46(s, 2H), 3.99(s, 3H), 6.85(d, 1H), 7.34(d, 1H), 7.60(dd, 1H), 7.88(dd, 1H), 8.10(d, 1H), 8.34(d, 1H)<br>MS APCI+ m/z 345/347 [MH]⁺ | 36% |
| 49 | OCH₃ | CH | ¹HNMR(CDCl₃, 400 MHz) δ: 3.35(s, 3H), 3.99(s, 3H), 4.48(s, 2H), 6.88(d, 1H), 7.34(d, 1H), 7.50(m, 1H), 7.88(m, 1H), 8.10(d, 1H), 8.35(m, 1H)<br>MS APCI+ m/z 332 [MH]⁺ | 50% |
| 50 | H | CH | ¹HNMR(CDCl₃, 400 MHz) δ: 2.38(s, 3H), 4.00(s, 3H), 6.90(d, 1H), 7.35(d, 1H), 7.40(dd, 1H), 7.88(dd, 1H), 8.06(d, 1H), 8.31(d, 1H)<br>MS APCI+ m/z 302/304 [MH]⁺ | 33% |
| 51 | CH₃OCH₂CH₂O– | CH | ¹HNMR(CDCl₃, 400 MHz) δ: 3.33(s, 3H), 3.48(m, 2H), 3.64(m, 2H), 3.99(s, 3H), 4.60(s, 2H), 6.86(d, 1H), 7.35(d, 1H), 7.60(dd, 1H), 7.88(dd, 1H), 8.09(d, 1H), 8.35(d, 1H). MS APCI+ m/z 376/378 [MH]⁺ | 62% |
| 52 | CH₃CH₂O– | CH | ¹HNMR(CDCl₃, 400 MHz) δ: 1.14(t, 3H), 3.50(q, 2H), 4.00(s, 3H), 4.52(s, 2H), 6.86(d, 1H), 7.34(d, 1H), 7.51(dd, 1H), 7.90(dd, 1H), 8.11(d, 1H), 8.36(d, 1H). MS APCI+ m/z 346 [MH]⁺ | |

Preparation 46 was purified by column chromatography on silica gel, eluting with ethyl acetate:pentane, 25:75 to 50:50 to 75:25.

Preparation 48 was purified by column chromatography on silica gel, eluting with dichloromethane:methanol:0.88 ammonia, 99:1:0.1 to 97:3:0.1, followed by trituration with diethyl ether.

Preparation 49 was purified by column chromatography on silica gel, eluting with ethyl acetate:pentane, 10:90 to 100:0, followed by trituration with diethyl ether.

Preparation 50 was purified by re-crystallisation from ethyl acetate.

Preparation 51 was purified by column chromatography on silica gel, eluting with dichloromethane:methanol:0.88 ammonia, 100:0:0 to 99:1:0.1.

Preparation 53

4-Bromo-2,3-dimethyl-pyridine 1-oxide

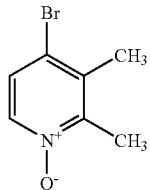

A mixture of 2,3-dimethyl-4-nitropyridine N-oxide (5 g, 29.7 mmol) and hydrogen bromide (30% wt in acetic acid, 100 mL) was heated for 48 hours at 100° C. The mixture was then filtered, washing through with 2M sodium hydroxide and the filtrate was extracted with dichloromethane (×3). The combined organic solutions were washed with brine, dried over sodium sulfate and concentrated in vacuo. The residue was purified by column chromatography on silica gel, eluting with ethyl acetate:pentane, 50:50, to afford the title product as a pale yellow solid.

$^1$HNMR (CDCl$_3$, 400 MHz) δ: 2.44 (s, 3H), 2.58 (s, 3H), 7.30 (d, 1H), 8.01 (d, 1H) MS APCl+ m/z 202/204 [MH]$^+$

Preparation 54

4-(2,3-Dimethyl-1-oxy-pyridin-4-yl)-benzoic acid methyl ester

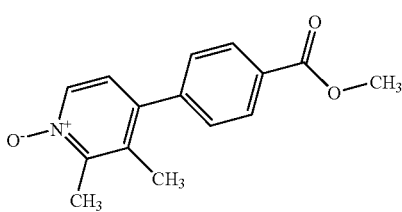

A mixture of the product of preparation 53 (765 mg, 3.78 mmol), 4-methoxycarbonylphenylboronic acid (750 mg, 4.16 mmol), caesium carbonate (3.7 g, 11.34 mmol) and the product of preparation 3 (50 mg, cat.) in 1,4-dioxan (20 mL) was heated at 110° C. for 3 hours. The mixture was then partitioned between ethyl acetate and water and the aqueous layer was separated and extracted by dichloromethane (×3). The combined organic solutions were washed with brine, dried over sodium sulfate and concentrated in vacuo to give a dark yellow solid. This solid was triturated with diethyl ether to afford the title compound as a pale brown solid in 87% yield.

$^1$HNMR (CDCl$_3$, 400 MHz) δ: 2.24 (s, 3H), 2.60 (s, 3H), 3.95 (s, 3H), 7.02 (d, 1H), 7.35 (m, 2H), 8.12 (m, 2H), 8.22 (d, 1H). MS APCl+ m/z 258 [MH]

Preparation 55

4-(2,3-Dimethyl-1-oxy-pyridin-4-yl)-benzoic acid hydrazide

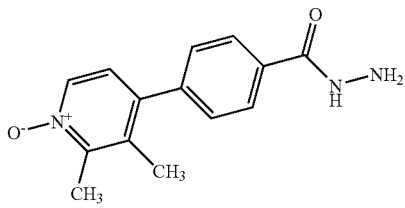

A mixture of the product of preparation 54 (850 mg, 3.3 mmol) and hydrazine monohydrate (482 μL, 9.9 mmol) in methanol (15 mL) was heated under reflux for 3 hours. A further amount of hydrazine monohydrate (482 μL, 9.9 mmol) was then added to the reaction mixture and heating continued for 18 hours. The mixture was then filtered through Celite®, washing through with methanol and the filtrate was concentrated in vacuo to give a white solid. The solid was slurried in ethyl acetate, filtered off, washed with diethyl ether (×2) and vacuum dried to afford the title compound as a white solid in 94% yield, 800 mg.

$^1$HNMR (CDCl$_3$, 400 MHz) δ: 2.18 (s, 3H), 2.41 (s, 3H), 4.58 (m, 2H), 7.14 (d, 1H), 7.42 (d, 2H), 7.96 (d, 2H), 8.18 (d, 1H), 9.85 (s, 1H). MS APCl+ m/z 258 [MH]$^+$

Preparation 56

1,1,1,2-Tetramethoxy-ethane

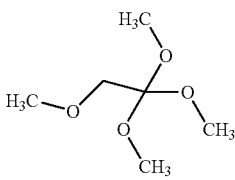

Methoxyacetonitrile (50.0 g, 704 mmol) was dissolved in a mixture of methanol (34 mL) and diethyl ether (210 mL) and the mixture cooled to 00° C. Hydrogen chloride gas was bubbled through the solution for 20 minutes and the reaction mixture was stirred at room temperature for 2 hours. Hydrogen chloride gas was then bubbled through the mixture for a second time and it was allowed to stand at room temperature for 18 hours. The mixture was filtered and the resulting white solid was washed with diethyl ether, dissolved in methanol (340 mL) and stirred for 90 minutes. The solution was then diluted with ether (370 mL), heated under reflux for 6 hours and left to stand at room temperature for 18 hours. Additional ether (200 mL) was added and the mixture was filtered off.

The filtrate was washed with 10% sodium carbonate solution, dried over magnesium sulfate and concentrated in vacuo to yield the title product, 34.5 g.

$^1$HNMR (CDCl$_3$, 400 MHz) δ: 3.29 (s, 9H), 3.39 (s, 3H), 3.50 (s, 2H)

Preparation 57

4-[4-(5-Methoxymethyl-[1,3,4]oxadiazol-2-yl)-phenyl]-2,3-dimethyl-pyridine 1-oxide

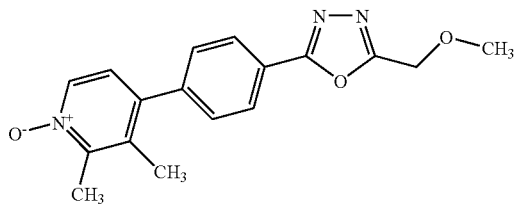

para-Toluenesulfonic acid (20 mg, cat.) was added to a mixture of the products of preparations 55 (400 mg, 1.56 mmol) and 56 (470 mg, 3.12 mmol) in methanol (8 mL) and the mixture was heated under reflux for 10 hours. The mixture was then treated with sodium hydrogen carbonate solution and the aqueous mixture was extracted with ethyl acetate (×3). The combined organic solutions were washed with brine, dried over sodium sulfate and concentrated in vacuo to afford the title product as a yellow oil in 25% yield, 122 mg.

$^1$HNMR (CDCl$_3$, 400 MHz) δ: 2.25 (s, 3H), 2.62 (s, 3H), 3.52 (s, 3H), 4.70 (s, 2H), 7.04 (d, 1H), 7.41 (d, 2H), 8.16 (d, 2H), 8.25 (d, 1H). MS APCl+ m/z 312 [MH]$^+$

Preparation 58

6-Chloro-pyridazine-3-carboxylic acid methyl ester

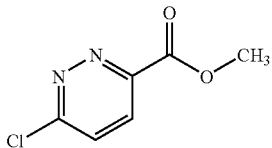

Oxalyl chloride (1.14 mL, 13.09 mmol), was added dropwise to an ice-cold suspension of 6-chloro-pyridazine-3-carboxylic acid [(1.9 g, 11.9 mmol), *J. Het. Chem.* 29(6), 1583-92; 1992] in a mixture of dichloromethane (50 mL) and N,N-dimethylformamide (1 drop) and the mixture was stirred for 1 hour at room temperature. The reaction mixture was then evaporated under reduced pressure and the residue was diluted with dichloromethane (30 mL) and cooled to 0° C. Methanol (485 μL, 11.9 mmol) was added and the mixture was stirred at 0° C. for 1 hour. Sodium hydrogen carbonate solution was then added to the reaction mixture and the aqueous layer was separated and extracted with dichloromethane (×2). The combined organic solutions were washed with brine, dried over sodium sulfate and concentrated in vacuo to afford the title compound as a white solid in 65% yield, 1.33 g.

$^1$HNMR (CDCl$_3$, 400 MHz) δ: 4.09 (s, 3H), 7.67 (d, 1H), 8.16 (d, 1H). MS APCl+ m/z 173 [MH]$^+$

Preparation 59

6-(4-Fluoro-2-methyl-phenyl)-pyridazine-3-carboxylic acid methyl ester

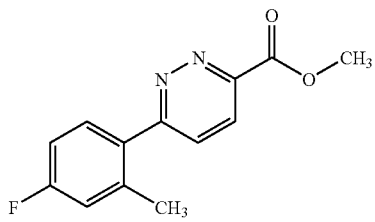

The title compound was prepared from the product of preparation 58 and 4-fluoro-2-methylphenyl boronic acid, using the method of preparation 54. Purification of the crude product by column chromatography on silica gel, eluting with pentane:ethyl acetate:methanol, 75:25:1 to 50:50:1 afforded the desired product as a beige solid in 16% yield.

$^1$HNMR (CDCl$_3$, 400 MHz) δ: 2.44 (s, 3H), 4.11 (s, 3H), 7.06 (m, 2H), 7.47 (dd, 1H), 7.71 (d, 1H), 8.26 (d, 1H). MS APCl+ m/z 247 [MH]$^+$

Preparation 60

6-(4-Fluoro-2-methyl-phenyl)-pyridazine-3-carboxylic acid hydrazide

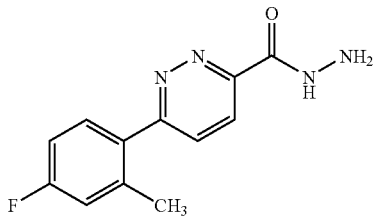

Hydrazine monohydrate (69 μL, 1.42 mmol) was added to a suspension of the product of preparation 59 (290 mg, 1.18 mmol) in methanol (5 mL) and the mixture was stirred for 18 hours at room temperature. The resulting precipitate was filtered off and dried to afford the title compound as a peach solid in 83% yield, 240 mg.

$^1$HNMR (CDCl$_3$, 400 MHz) δ: 2.42 (s, 3H), 4.18 (brs, 2H), 7.06 (m, 2H), 7.46 (dd, 1H), 7.75 (d, 1H), 8.33 (d, 1H), 9.18 (brs, 1H). MS APCl+ m/z 247 [MH]

Preparation 61

6-(4-Fluoro-2-methyl-phenyl)-pyridazine-3-carboxylic acid N'-(2-methoxy-acetyl)-hydrazide

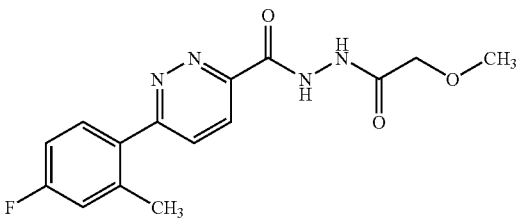

The title compound was prepared from the product of preparation 60 and methoxyacetyl chloride, using the method of preparation 8, as a beige foam in 95% yield.

$^1$HNMR (CDCl$_3$, 400 MHz) δ: 2.43 (s, 3H), 3.52 (s, 3H), 4.14 (s, 2H), 7.06 (m, 2H), 7.46 (m, 1H), 7.76 (d, 1H), 8.33 (d, 1H), 8.80 (brs, 1H), 10.06 (brs, 1H). MS APCl+ m/z 319 [MH]$^+$ Preparation 62

3-(4-Fluoro-2-methyl-phenyl)-6-(5-methoxymethyl-[1,3,4]oxadiazol-2-yl)-pyridazine

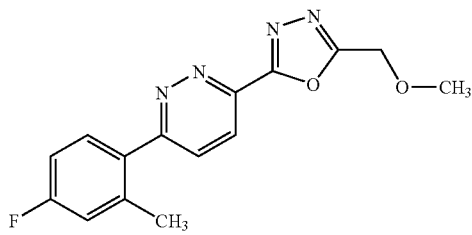

The title compound was prepared from the product of preparation 61 and phosphorous oxychloride, using the method of preparation 13. The crude product was purified by column chromatography on silica gel, eluting with dichloromethane:methanol, 99:1 to 98:2, to afford the desired compound as a beige solid in 15% yield.

$^1$HNMR (CDCl$_3$, 400 MHz) δ: 2.43 (s, 3H), 3.53 (s, 3H), 4.80 (s, 2H), 7.06 (m, 2H), 7.46 (m, 1H), 7.74 (d, 1H) 8.43 (d, 1H). MS APCl+ m/z 301 [MH]$^+$

Preparation 63

5-Bromo-pyrimidine-2-carbonitrile

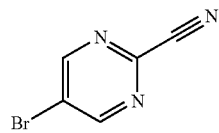

A solution of 5-bromo-2-chloropyrimidine (10 g, 51.8 mmol) in dimethylsulfoxide (26 mL) was added to a mixture of sodium cyanide (2.59 g, 51.8 mmol) and triethylenediamine (1.2 g, 10.4 mmol) in dimethylsulfoxide (14 mL) and water (28 mL). The resulting mixture was stirred for 18 hours at room temperature. The mixture was then diluted with water (130 mL) and extracted with diethyl ether (3×150 mL). The combined organic solutions were dried over sodium sulfate and concentrated in vacuo to give a pale yellow solid. Recrystallisation of the solid from hot dichloromethane afforded the title product in 99% yield, 9.4 g.

$^1$HNMR (CDCl$_3$, 400 MHz) δ: 8.84 (s, 2H).

Preparation 64

5-Bromo-pyrimidine-2-carboxylic acid

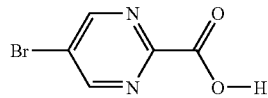

A mixture of sodium hydroxide (4.88 g, 120 mmol) and the product of preparation 63 (7.5 g, 40.8 mmol) in water (122 mL) was heated at 60° C. for 1 hour. The mixture was then acidified with 1M hydrochloric acid, extracted with ethyl acetate and dichloromethane and concentrated in vacuo to afford some title compound as a white solid, 300 mg. The aqueous solution was also evaporated under reduced pressure and the residue was extracted into dichloromethane:methanol, 90:10. The precipitate was filtered off and the filtrate was concentrated in vacuo to afford further title compound as a white solid, 5.5 g.

$^1$HNMR (DMSO-D$_6$, 400 MHz) δ: 9.10 (s, 2H), 13.8 (brs, 1H). MS APCl+ m/z 203 [MH]$^+$ Preparation 65

5-Bromo-pyrimidine-2-carboxylic acid methyl ester

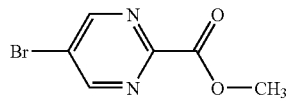

Fuming hydrochloric acid was passed through an ice-cooled solution of the product of preparation 64 (5.5 g, 27 mmol) in methanol (50 mL) until saturated. The reaction mixture was warmed to room temperature and was stirred for 18 hours. The solvent was then evaporated under reduced pressure and the residue was dissolved in dichloromethane, washed with water and sodium hydrogen carbonate solution, dried over magnesium sulfate and concentrated in vacuo to afford the title compound as yellow solid in 57% yield, 3.5 g.

$^1$HNMR (CDCl$_3$, 400 MHz) δ: 4.05 (s, 3H), 9.00 (s, 2H). MS APCl+ m/z 218 [MH]$^+$

Preparation 66

5-Bromo-pyrimidine-2-carboxylic acid hydrazide

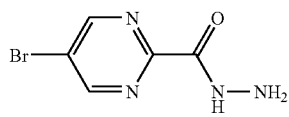

The title compound was prepared from the product of preparation 65 and hydrazine monohydrate, using the method of preparation 6, as a yellow solid in quantitative yield.

$^1$HNMR (CDCl$_3$, 400 MHz) δ: 4.20 (s, 2H), 8.90 (m, 3H). MS APCl+ m/z 217 [MH]$^+$

Preparation 67

5-Bromo-pyrimidine-2-carboxylic acid N'-(2-methoxy-acetyl)-hydrazide

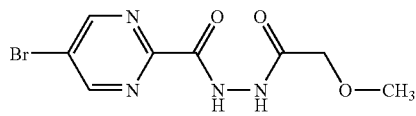

The title compound was prepared from the product of preparation 66 and methoxyacetyl chloride, using the method of preparation 8, as a white solid in 45% yield.

$^{1}$HNMR (DMSO-D$_{6}$, 400 MHz) δ: 3.32 (s, 3H), 3.98 (s, 2H), 9.20 (s, 2H), 10.02 (s, 1H), 10.66 (s, 1H). MS APCl+ m/z 290 [MH]$^{+}$

Preparation 68

5-Bromo-2-(5-methoxymethyl-[1,3,4]oxadiazol-2-yl)-pyrimidine

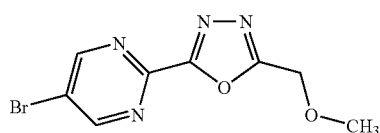

The title compound was prepared from the product of preparation 67, using the method of preparation 13. The crude product was purified by column chromatography on silica gel, eluting with dichloromethane:methanol, 99.5:0.5 to 99:1, to afford the desired compound as a white solid in 45% yield.

$^{1}$HNMR (CDCl$_{3}$, 400 MHz) δ: 3.52 (s, 3H), 4.78 (s, 2H), 9.02 (s, 2H). MS APCl+ m/z 271 [MH]$^{+}$

Preparation 69

5-(4-Fluoro-2-methyl-phenyl)-2-(5-methoxymethyl-[1,3,4]oxadiazol-2-yl)-pyrimidine

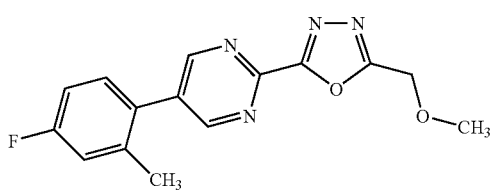

A solution of sodium carbonate (295 mg, 2.78 mmol) in water (3 mL) was added to a solution of the product of preparation 68 (376 mg, 1.39 mmol), 4-fluoro-2-methylphenyl boronic acid (320 mg, 2.08 mmol) and palladium triphenylphosphine (48 mg, cat) in 1,2-dimethoxyethane (3 mL) and the mixture was heated under reflux for 2 hours. The reaction mixture was then evaporated under reduced pressure and the residue was partitioned between water and ethyl acetate. The resulting precipitate was filtered off, washing through with water, ethyl acetate and diethyl ether, and dried to afford the title compound as a beige solid in 59% yield, 332 mg.

$^{1}$HNMR (CDCl$_{3}$, 400 MHz) δ: 2.33 (s, 3H), 3.53 (s, 3H), 4.81 (s, 2H), 7.09 (m, 2H) 7.25 (m, 1H), 8.90 (s, 2H). MS APCl+ m/z 301 [MH]$^{+}$

Preparation 70

5-Bromo-2-(5-methyl-[1,3,4]oxadiazol-2-yl)-pyridine

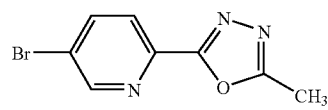

The title compound was prepared from the product of preparation 6 and N,N-dimethylacetamide dimethyl acetal, using the method of preparation 4, as a white solid in 47% yield.

$^{1}$HNMR (CDCl$_{3}$, 400 MHz) δ: 2.65 (s, 3H), 8.01 (m, 1H), 8.12 (m, 1H), 8.80 (m, 1H). MS APCl+ m/z 240/242 [MH]$^{+}$

Preparation 71

3-[3-(5-Bromo-pyridin-2-yl)-5-methyl-[1,2,4]triazol-4-yl]-2,6-dimethoxy-pyridine

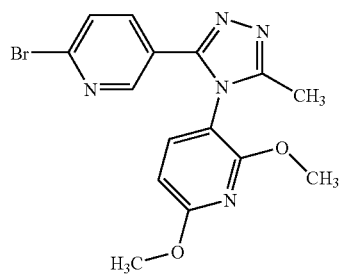

3-Amino-2,6-dimethoxypyridine monohydrochloride (2 g, 13 mmol) was partitioned between sodium carbonate solution and ethyl acetate. The organic layer was separated, washed with brine, dried over sodium sulfate and concentrated in vacuo to afford the free base. The base was then dissolved in xylene (30 mL) and the product of preparation 70 (1.8 g, 7.5 mmol) and para-toluenesulfonic acid (50 mg, cat) were added. The resulting mixture was heated under reflux for 18 hours. The reaction mixture was concentrated in vacuo and the residue purified by column chromatography on silica gel eluting with dichloromethane:methanol 100:0 to 98:2, to afford the title product as a purple solid in 23% yield, 628 mg.

$^{1}$HNMR (CDCl$_{3}$, 400 MHz) δ: 2.49 (s, 3H), 3.80 (s, 3H), 3.98 (s, 3H), 6.41 (d, 1H), 7.45 (d, 1H), 7.92 (dd, 1H), 8.11 (d, 1H), 8.37 (d, 1H). MS APCl+ m/z 377 [MH]$^{+}$

Preparation 72

5-(4-Fluoro-2-methyl-phenyl)-2-(5-methyl-[1,3,4]oxadiazol-2-yl)-pyridine

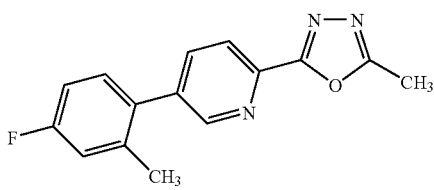

A mixture of the product of preparation 40 (545 mg, 2.79 mmol), 4-fluoro-2-methylphenyl boronic acid (643 mg, 4.18 mmol), caesium carbonate (2.7 g, 8.29 mmol) and the product of preparation 3 (10 mg, cat.) in 1,4-dioxan (25 mL) was heated under reflux for 4 hours. The reaction mixture was then cooled to room temperature, filtered through Celite® and concentrated in vacuo to afford the title compound as a pale yellow solid in quantitative yield.

$^1$HNMR (CDCl$_3$, 400 MHz) δ: 2.40 (s, 3H), 2.66 (s, 3H), 7.00 (m, 2H), 7.43 (dd, 1H), 7.53 (d, 1H), 8.37 (d, 1H) 9.29 (d, 1H). MS APCl+ m/z 270 [MH]$^+$

Preparations 73 to 81

The following compounds of the general formula shown below were prepared in quantitative yield, by the method of preparation 72, using the appropriate oxadiazole (preparations 14-16) and boronic acid.

The progress of the reactions was monitored by tlc analysis and the mixtures were heated under reflux until all of the starting materials had been consumed.

| No. | R$^1$ | R$^2$ | Y | Data |
|---|---|---|---|---|
| 73 | 2,3-dimethylphenyl | H | N | $^1$HNMR(CDCl$_3$, 400 MHz) δ: 2.29(s, 3H), 2.37(s, 3H), 2.70(s, 3H), 7.21-7.34(m, 3H), 8.81(d, 1H), 9.51(d, 1H). MS ES+ m/z 289 [MNa]$^+$ |
| 74 | 4-fluoro-2-methylphenyl | H | N | $^1$HNMR(CDCl$_3$, 400 MHz) δ: 2.46(s, 3H), 2.70(s, 3H), 7.06(m, 2H), 7.50(m, 1H), 8.82(d, 1H), 9.49(d, 1H). MS ES+ m/z 293 [MNa]$^+$ |
| 75 | 4-fluoro-2-methylphenyl | OCH$_3$ | CH | $^1$HNMR(CDCl$_3$, 400 MHz) δ: 2.41(s, 3H), 3.52(s, 3H), 4.75(s, 2H), 6.94-7.04(m, 2H), 7.44(dd, 1H), 7.55(dd, 1H), 8.42(d, 1H), 9.35(dd, 1H). MS APCl+ m/z 300 [MH]$^+$ |
| 76 | 4-fluoro-2-methylphenyl | OCH$_3$ | N | $^1$HNMR(CDCl$_3$, 400 MHz) δ: 2.46(s, 3H), 3.53(s, 3H), 4.79(s, 2H), 7.06(m, 2H), 7.51(m, 1H), 8.84(d, 1H), 9.51(d, 1H). MS APCl+ m/z 301 [MH]$^+$ |
| 77 | 3-fluoro-4-methylphenyl | OCH$_3$ | N | $^1$HNMR(CDCl$_3$, 400 MHz) δ: 2.40(d, 3H), 3.52(s, 3H), 4.51(s, 2H), 7.23-7.30(m, 3H), 9.06(s, 1H), 9.40(s, 1H) MS ES+ m/z 433 [MCs]$^+$ |
| 78 | 3-methoxy-2-fluorophenyl | OCH$_3$ | N | $^1$HNMR(CDCl$_3$, 400 MHz) δ: 3.78(s, 3H), 4.09(s, 3H), 4.80(s, 2H), 7.01-7.18(m, 2H), 7.54-7.72(m, 1H), 9.26(s, 1H), 9.57(s, 1H) MS ES+ m/z 449 [MCs]$^+$ |

-continued

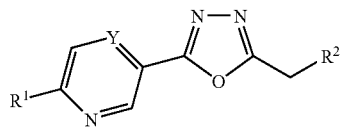

| No. | R¹ | R² | Y | Data |
|---|---|---|---|---|
| 79 | 2-OCH₃, 4-CH₃ phenyl | OCH₃ | N | ¹HNMR(CDCl₃, 400 MHz) δ: 2.37(s, 3H), 3.52(s, 3H), 3.89(s, 3H), 4.78(s, 2H), 6.95(d, 1H), 7.25(m, 1H), 7.77(m, 1H), 9.35(d, 1H), 9.49(d, 1H). MS ES+ m/z 445 [MCs]⁺ |
| 80 | 2-OCH₃, 4-F phenyl | OCH₃ | N | ¹HNMR(CDCl₃, 400 MHz) δ: 3.52(s, 3H), 3.91(s, 3H), 4.78(s, 2H), 6.99(m, 1H), 7.17(m, 1H), 7.77(m, 1H), 9.41(d, 1H), 9.50(d, 1H). MS ES+ m/z 461 [MCs]⁺ |
| 81 | 2,6-dimethylphenyl | OCH₃ | N | ¹HNMR(CDCl₃, 400 MHz) δ: 2.39(s, 3H), 2.40(s, 3H), 3.53(s, 3H), 4.79(s, 2H), 7.03-7.41(m, 2H), 8.86(s, 1H), 9.52(d, 1H). MS ES+ m/z 429 [MCs]⁺ |

Preparation 82

Methyl-(5-nitro-pyridin-2-yl)-amine

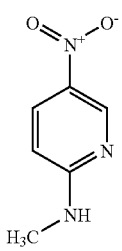

Methylamine gas was bubbled through a stirred solution of 2-chloro-5-nitropyridine (4 g, 25.2 mmol) in dichloromethane (60 mL), at room temperature, until saturation had occurred. The resulting yellow precipitate was then filtered off, washed with dichloromethane and dried under vacuum to afford the title compound as a yellow solid in 80% yield, 3.07 g.

¹HNMR (CDCl₃, 400 MHz) δ: 3.05 (d, 3H), 5.41 (bs, 1H), 6.37 (d, 1H), 8.21 (d, 1H), 9.03 (d, 1H). MS APCl+ m/z 154 [MH]⁺

Preparation 83

N*2*-Methyl-pyridine-2,5-diamine

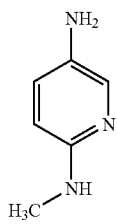

The product of preparation 82 (3.0 g, 19.5 mmol) and 10% Pd/C (300 mg, cat.) were stirred in ethanol (150 mL) under 60 psi of hydrogen gas for 18 hours. The reaction mixture was then filtered through Celite® and the filtrate was concentrated in vacuo to afford the title product in 17% yield, 400 mg.

$^1$HNMR (CDCl$_3$, 400 MHz) δ: 2.85 (s, 3H), 3.19 (s, 2H), 4.11 (s, 1H), 6.31 (d, 1H), 6.97 (dd, 1H), 7.69 (d, 1H). MS APCl+ m/z 269 [MNa]$^+$

Preparation 84

4,6-Dichloro-nicotinic acid methyl ester

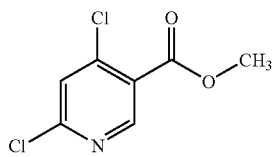

3-Pyridinecarboxylic acid [(27 g, 160 mmol), *J. Het. Chem.*, 20, 1363; 1983] was added portionwise to phosphorus oxychloride (180 mL) and the mixture was heated under reflux for 7 hours and stirred at room temperature for 18 hours. The mixture was then concentrated in vacuo to a low volume and the residue was quenched with water. The aqueous mixture was neutralised with sodium hydrogen carbonate solution and extracted with chloroform (3×150 mL). The combined organic solutions were washed with brine, dried over sodium sulfate and concentrated in vacuo to afford the title compound as a red oil in 83% yield, 27.2 g.

$^1$HNMR (CDCl$_3$, 400 MHz) δ: 3.96 (s, 3H), 7.47 (s, 1H), 8.85 (s, 1H). MS APCl+ m/z 206 [MH]$^+$

Preparations 85 and 86

Sodium methoxide (0.5M in methanol, 48.6 mL, 24.3 mmol) was added dropwise to an ice-cold solution of the product of preparation 84 (5.0 g, 24.3 mmol) in methanol (20 mL). The mixture was allowed to warm to room temperature and was stirred for 2 hours. The solvent was then evaporated under reduced pressure and the residue was partitioned between water (50 mL) and chloroform (50 mL). The layers were separated and the aqueous layer was extracted with chloroform (2×75 mL). The combined organic solutions were then dried over sodium sulphate and concentrated in vacuo to give an orange oil. The oil was purified by column chromatography on silica gel, eluting with dichloromethane (100%) to afford the product of preparation 85 as a white solid in 7.6% yield, 370 mg. Further elution with dichloromethane then isolated the product of preparation 86 as a white solid in 27% yield, 1.32 g.

Preparation 85

4-Chloro-6-methoxy-nicotinic acid methyl ester

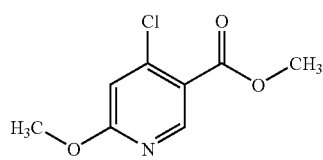

$^1$HNMR (CDCl$_3$, 400 MHz) δ: 3.90 (s, 3H), 3.96 (s, 3H), 6.81 (s, 1H), 8.71 (s, 1H). MS APCl+ m/z 202 [MH]$^+$

Preparation 86

6-Chloro-4-methoxy-nicotinic acid methyl ester

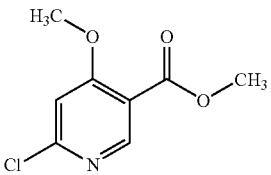

$^1$HNMR (CDCl$_3$, 400 MHz) δ: 3.87 (s, 3H), 3.94 (s, 3H), 6.90 (s, 1H), 8.68 (s, 1H). MS APCl+ m/z 202 [MH]$^+$

Preparation 87

6-Chloro-4-methoxy-nicotinic acid hydrazide

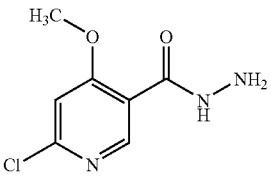

Hydrazine monohydrate (690 μL, 14.2 mmol) was added to a suspension of the product of preparation 86 (2.7 g, 13.4 mmol) in methanol (35 mL), cooled to −5° C., and the mixture was stirred for 3 hours. The mixture was then warmed to room temperature and was stirred for 18 hours. The resulting precipitate was filtered off and dried to afford some title compound as a white solid, 990 mg. Tlc analysis of the filtrate showed that not all of the starting material had been consumed and so further hydrazine monohydrate (267 μL, 5.51 mmol) was added and the reaction mixture was stirred for 24 hours. The resulting precipitate was collected by filtration and dried to afford a further crop of title compound as a yellow solid, 832 mg.

$^1$HNMR (CDCl$_3$, 400 MHz) δ: 3.92 (s, 3H), 4.55 (bd, 2H), 7.29 (s, 1H), 8.37 (s, 1H), 9.38 (m, 1H). MS APCl+ m/z 247 [MH]$^+$

Preparation 88

6-Chloro-4-methoxy-nicotinic acid N'-(2-methoxy-acetyl)-hydrazide

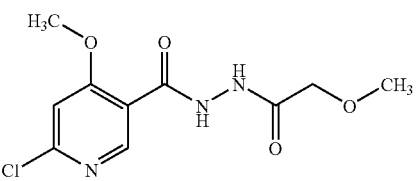

Methoxyacetyl chloride (733 L, 8.02 mmol) was added to an ice-cold suspension of the product of preparation 87 (1.16 g, 5.73 mmol) in dichloromethane (20 mL) and triethylamine (1.2 mL, 8.61 mmol) and the mixture was stirred for 18 hours at room temperature. The reaction mixture was then washed with water and brine, dried over sodium sulphate and concentrated in vacuo to give a pale yellow gum. The gum was purified by column chromatography on silica gel, eluting with dichloromethane:methanol, 100:0:0 to 95:5, to afford the title compound as a clear glass in 31% yield, 480 mg.

$^1$HNMR (CDCl$_3$, 400 MHz) δ: 3.48 (s, 3H), 4.08 (s, 3H), 4.10 (s, 2H), 6.96 (s, 1H), 9.03 (s, 1H), 9.25 (d, 1H), 9.99 (d, 1H). MS APCl+ m/z 274/276 [MH]$^+$

Preparation 89

2-Chloro-4-methoxy-5-(5-methoxymethyl-[1,3,4]oxadiazol-2-yl)-pyridine

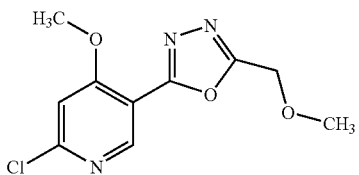

The title compound was prepared form the product of preparation 88 and phosphorus oxychloride, using the method of preparation 13, as a yellow oil in quantitative yield.

$^1$HNMR (CDCl$_3$, 400 MHz) δ: 3.49 (s, 3H), 4.04 (s, 3H), 4.73 (s, 2H), 7.01 (s, 1H), 8.83 (s, 1H). MS APCl+ m/z 256 [MH]$^+$

Preparation 90

2-Chloro-4-methoxy-5-[5-methoxymethyl-4-(6-methoxy-pyridin-3-yl)-4H-[1,2,4]triazol-3-yl]-pyridine

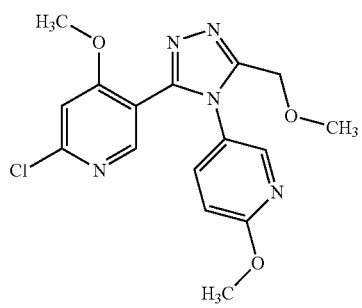

The title compound was prepared from the product of preparation 89 and 5-amino-2-methoxypyridine, using the method of preparation 18, as a pale yellow foam in 29% yield.

$^1$HNMR (CDCl$_3$, 400 MHz) δ: 3.37 (s, 3H), 3.61 (s, 3H), 3.93 (s, 3H), 4.49 (s, 2H), 6.76 (m, 2H), 7.43 (dd, 1H), 7.98 (d, 1H), 8.42 (s, 1H). MS APCl+ m/z 362 [MH]$^+$

Preparation 91

5-(4-Fluoro-2-methyl-phenyl)-pyrazine-2-carboxylic acid methyl ester

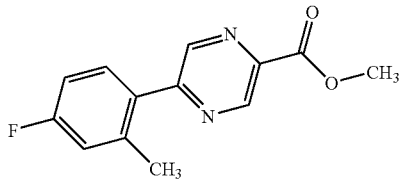

4-Fluoro-2-methylphenyl boronic acid (17.36 g, 112.7 mmol), caesium carbonate (70.8 g, 216.8 mmol) and the product of preparation 3 (1.5 mg, 8.67 mmol.) were added to a solution of 5-chloropyrazine-2-methylcarboxylate (15 g, 86.7 mmol) in 1,4-dioxan (2 L) and the mixture was heated under reflux for 2 hours. The reaction mixture was then filtered and concentrated in vacuo to afford the title compound in 99% yield, 21.33 g.

$^1$HNMR (CDCl$_3$, 400 MHz) δ: 2.40 (s, 3H), 4.05 (s, 3H), 7.05 (m, 2H), 7.45 (m, 1H), 8.80 (1, 1H), 9.35 (s, 1H). MS APCl+ m/z 247 [MH]$^+$

Preparation 92

5-(4-Fluoro-2-methyl-phenyl)-pyrazine-2-carboxylic acid hydrazide

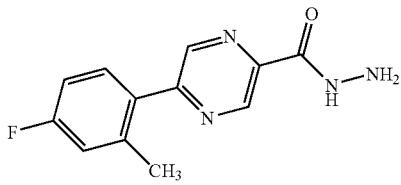

A mixture of the product of preparation 91 (42.5 g, 172.8 mmol) and hydrazine monohydrate (9.46 mL, 207.3 mmol) in methanol (600 mL) was heated under reflux for 30 hours. The reaction mixture was then cooled to room temperature and the precipitate was filtered off and dried in vacuo to afford the title compound in 75% yield, 7.10 g.

$^1$HNMR (DMSO, 400 MHz) δ: 2.35 (s, 3H), 4.60 (s, 2H), 7.20 (m, 2H), 7.60 (m, 1H), 8.80 (s, 1H), 9.15 (s, 1H), 10.2 (s, 1H).

Examples 1-4

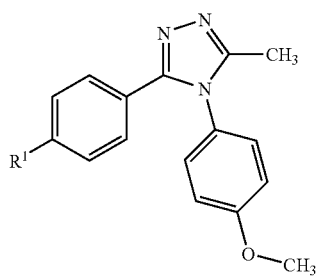

The bromo compound of preparation 5 (100 mg, 0.29 mmol), the palladium complex of preparation 3 (10 mg, cat.), caesium carbonate (440 mg, 1.35 mmol) and the appropriate boronic acid (0.73 mmol) were suspended in 1,4-dioxan (5 mL) and the reaction mixture heated to 120° C. for 90 minutes. Additional 1,4-dioxan (4 mL) was added and the reaction mixture heated to 100° C. for a further 4 hours. The reaction mixture was filtered under vacuum, washing through with dichloromethane. The filtrate was concentrated in vacuo and the residue purified by column chromatography on silica gel eluting with dichloromethane:methanol:0.88 ammonia 95:5:0.5 to yield the desired product.

| No. | $R^1$ | Data | Yield |
|---|---|---|---|
| 1 | (2-fluoro-6-methoxyphenyl) | MS ES+ m/z 390 [MH]$^+$ | 9% |
| 2 | (2-methyl-3-methylphenyl) | $^1$HNMR(CDCl$_3$, 400 MHz) δ: 2.01(s, 3H), 2.22(s, 3H), 2.26(s, 3H), 3.75(s, 3H), 6.87(d, 1H), 7.02(m, 4H), 7.20(m, 2H), 7.24(m, 2H), 7.39(m, 2H) MS APCl+ m/z 370 [MH]$^+$ | 10% |
| 3 | (2,6-dimethylphenyl) | MS APCl+ m/z 370 [MH]$^+$ | 36% |
| 4 | (2-fluoro-3-methoxyphenyl) | $^1$HNMR(CDCl$_3$, 400 MHz) δ: 2.31(s, 3H), 3.79(s, 3H), 3.83(s, 3H), 7.02(m, 3H), 7.27(m, 2H), 7.34(d, 2H), 7.41(d, 2H), 7.57(d, 2H). MS APCl+ m/z 390 [MH]$^+$ | 52% |

Example 5

2-(4-Fluoro-2-methylphenyl)-5-(5-methoxymethyl-4-(6-methoxypyridin-3-yl)-4H-[1,2,4]triazol-3-yl)-pyridine

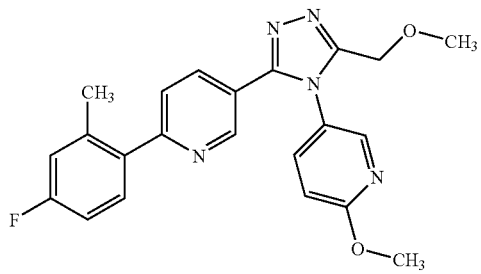

The title product was prepared by the method of preparation 18 using the product of preparation 19 and 5-amino-2-methoxypyridine. 140 mg, 15% yield of the desired product was produced.

$^1$HNMR (CDCl$_3$, 400 MHz) δ: 2.36 (s, 3H), 3.38 (s, 3H), 4.01 (s, 3H), 4.51 (s, 2H), 6.88 (d, 1H), 6.93-7.00 (m, 2H), 7.36 (dd, 1H), 7.40 (d, 1H), 7.56 (dd, 1H), 8.00 (dd, 1H), 8.15 (d, 1H), 8.64 (d, 1H). Microanalysis: C$_{22}$H$_{20}$FN$_5$O$_2$ requires; C, 65.18; H, 4.97; N, 17.27. found C, 65.01; H, 4.96; N, 17.27. MS APCl+ m/z 406 [MH]$^+$

Example 6

2-(2,3-Dimethylphenyl)-5-(5-methoxymethyl-4-(6-methoxypyridin-3-yl)-4H-[1,2,4]triazol-3-yl)-pyridine

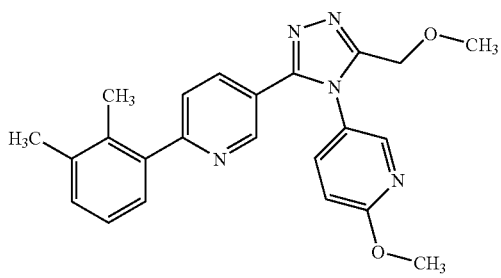

The title product was prepared by the method of preparation 18 using the product of preparation 20 and 5-amino-2-methoxypyridine. 325 mg, 36% of the desired product was produced.

$^1$HNMR (CDCl$_3$, 400 MHz) δ: 2.21 (s, 3H), 2.34 (s, 3H), 3.38 (s, 3H), 4.00 (s, 3H), 4.52 (s, 2H), 6.88 (d, 1H), 7.13-7.22 (m, 3H), 7.40 (d, 1H), 7.55 (d, 1H), 7.99 (dd, 1H), 8.16 (d, 1H), 8.64 (d, 1H). Microanalysis: C$_{23}$H$_{23}$N$_5$O$_2$. 0.1H$_2$O requires; C, 68.50; H, 5.80; N, 17.37. found C, 68.24; H, 5.90; N, 17.05. MS APCl+ m/z 402 [MH]$^+$

Example 7

5-(4-Fluoro-2-methylphenyl)-2-(((5-methoxymethyl-4-(6-methoxypyridin-3-yl))-4H-[1,2,4]triazol-3-yl)-pyridine

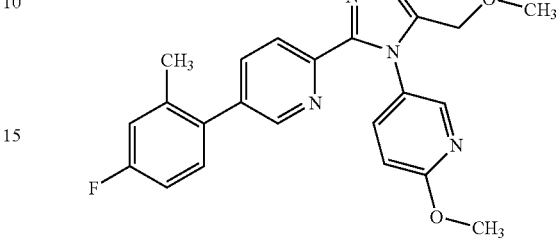

The bromo compound of preparation 18 (250 mg, 0.66 mmol), 2-methyl-4-fluoro-phenylboronic acid (235 mg, 1.53 mmol), the palladium complex of preparation 3 (10 mg, cat.) and caesium carbonate (1.00 g, 3.07 mmol) were added to 1,4-dioxan (15 mL) and the reaction mixture heated to 110° C. for 4 hours. The reaction mixture was filtered through Arbocel®, washed through with dichloromethane and the filtrate concentrated in vacuo. The residue was purified by column chromatography on silica gel eluting with dichloromethane:methanol 100:0 to 95:5 to yield the title product, 128 mg, 48% yield as a pale pink solid.

$^1$HNMR (DMSO-D$_6$, 400 MHz) δ: 2.21 (s, 3H), 3.18 (s, 3H), 3.89 (s, 3H), 4.44 (s, 2H), 6.94 (m, 1H), 7.09 (m, 1H), 7.19 (m, 1H), 7.28 (m, 1H), 7.81 (m, 1H), 7.94 (m, 1H), 8.15 (m, 1H), 8.23 (m, 1H), 8.32 (m, 1H). MS APCl+ m/z 406 [MH]$^+$

Example 8

5-(2,3-Dimethylphenyl)-2-[5-(methoxymethyl)-4-(6-methoxypyridin-3-yl)-4H-1,2,4-triazol-3-yl]pyridine

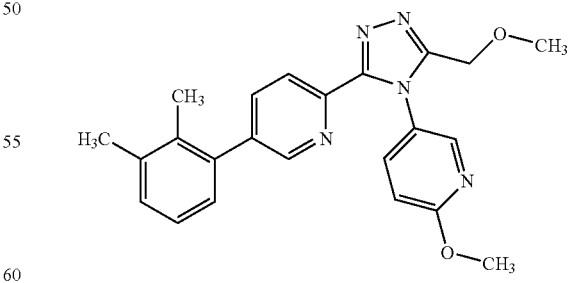

The title product was prepared by the method of example 7 using 2,3-dimethylphenylboronic acid. 132 mg, 49% yield of the desired product was prepared as a pale pink solid.

$^1$HNMR (DMSO-D$_6$, 400 MHz) δ: 2.07 (s, 3H), 2.38 (s, 3H), 3.17 (s, 3H), 3.89 (s, 3H), 4.44 (s, 2H), 6.94 (m, 1H), 7.04

(m, 1H), 7.15 (m, 1H), 7.22 (m, 1H), 7.82 (m, 1H), 7.90 (m, 1H), 8.15 (m, 1H), 8.24 (m, 1H), 8.28 (m, 1H). MS APCl+ m/z 402 [MH]+

Example 9

1-[5-[5-(2,3-Dimethylphenyl)-pyridin-2-yl]-4-(6-methoxypyridin-3-yl)-4H-[1,2,4]triazol-3-ylmethyl]-pyrrolidine-(2S)-2-carboxylic acid amide

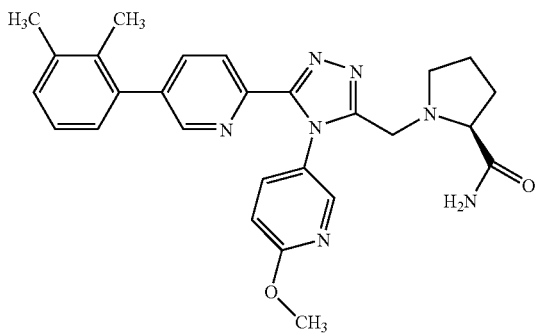

The bromo compound of preparation 27 (125 mg, 0.27 mmol), 2,3-dimethylphenyl boronic acid (61 mg, 0.41 mmol) and the palladium complex of preparation 3 (10 mg) were dissolved in 1,2-dimethoxyethane (4 mL) and the solution was treated with sodium carbonate (58 mg, 0.55 mmol). The reaction mixture was heated to reflux for 1 hour and then concentrated in vacuo. The residue was taken up in ethyl acetate (25 mL) and washed with water (25 mL), 2M sodium hydroxide solution (25 mL) and brine (25 mL). The solution was dried over magnesium sulfate and concentrated in vacuo. The residue was purified by column chromatography on silica gel eluting with dichloromethane:methanol:0.88 ammonia 100:0:0 to 97:3:0.3 to yield the title product, 95 mg, 72% yield.
¹HNMR (CDCl₃, 400 MHz) δ: 1.80 (m, 2H), 2.00 (m, 1H), 2.10 (s, 3H), 2.20 (m, 1H), 2.40 (s, 3H), 2.60 (m, 1H), 3.20 (m, 2H), 3.80 (m, 2H), 4.00 (s, 3H), 5.00 (s, 1H), 6.80 (s, 1H), 6.90 (d, 1H), 7.00 (d, 1H), 7.10 (d, 1H), 7.20 (d, 1H), 7.60 (d, 1H), 7.70 (d, 1H), 8.80 (s, 1H), 8.20 (m, 2H). MS ES+ m/z 484 [MH]+

Example 10

5-(2,3-Dimethylphenyl)-2-(5-pyrrolidin-1-ylmethyl-4-(6-methoxypyridin-3-yl)-4H-[1,2,4]triazol-3-yl)-pyridine

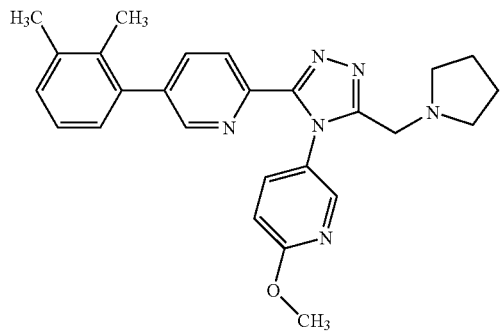

80 mg, 38% yield of the title product was prepared by the method of example 9 using the bromo compound of preparation 28.
¹HNMR (CDCl₃, 400 MHz) δ: 1.80 (s, 4H), 2.10 (s, 3H), 2.40 (s, 3H), 2.50 (s, 4H), 3.70 (s, 2H), 4.00 (s, 3H), 6.80 (d, 1H), 7.00 (d, 1H), 7.20 (m, 2H), 7.70 (t, 2H), 8.10 (d, 1H), 8.20 (d, 1H), 8.30 (s, 1H). MS ES+ m/z 441 [MH]+

Example 11

2-(4-Fluoro-2-methylphenyl)-5-[5-methoxymethyl-4-(6-methoxypyridin-3-yl)-4H-[1,2,4]triazol-3-yl]-pyrazine

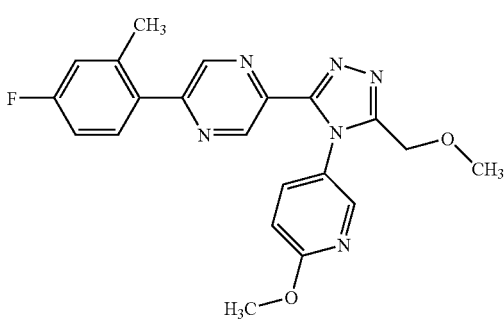

The product of preparation 22 (450 mg, 1.50 mmol), para-toluenesulfonic acid monohydrate (30 mg) and 5-amino-2-methoxypyridine (205 mg, 1.65 mmol) were added to xylene (8 mL) and the reaction mixture heated to 145° C. for 18 hours. The reaction mixture was concentrated in vacuo and the residue purified by column chromatography on silica gel eluting with dichloromethane:methanol:0.88 ammonia 100:0:0 to 99.5:0.5:0.05 to 99:1:0.1 to yield the title product, 300 mg, 49% yield as a green solid.
¹HNMR (CDCl₃, 400 MHz) δ: 2.38 (s, 3H), 3.34 (s, 3H), 3.99 (s, 3H), 4.50 (s, 2H), 6.85 (d, 1H), 6.95-7.03 (m, 2H), 7.36-7.42 (m, 1H), 7.60 (dd, 1H), 8.12 (d, 1H), 8.40 (s, 1H), 9.48 (s, 1H). MS APCl+ m/z 407 [MH]+

Example 12

2-(2,3-Dimethylphenyl)-5-[5-methoxymethyl-4-(6-methoxypyridin-3-yl)-4H-[1,2,4]triazol-3-yl]-pyrazine

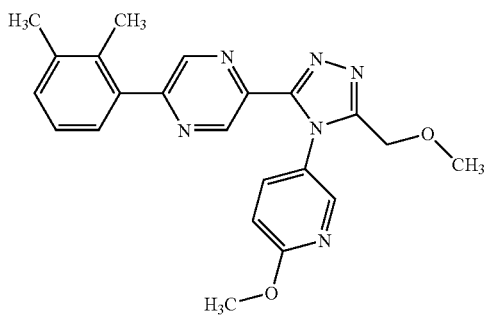

42 mg, 7% yield of the title product was prepared by the method of example 11, using the product of preparation 21.
¹HNMR (CDCl₃, 400 MHz) δ: 2.23 (s, 3H), 2.34 (s, 3H), 3.36 (s, 3H), 4.00 (s, 3H), 4.50 (m, 2H), 6.86 (d, 1H), 7.19 (d, 1H), 7.20 (s, 1H), 7.24 (m, 1H), 7.62 (dd, 1H), 8.14 (d, 1H), 8.41 (d, 1H), 9.49 (d, 1H). MS APCl+ m/z 403 [MH]+

Example 13

2-(2,3-Dimethylphenyl)-5-[4-(6-methoxypyridin-3-yl)-5-methyl-4H-[1,2,4]triazol-3-yl]-pyrazine

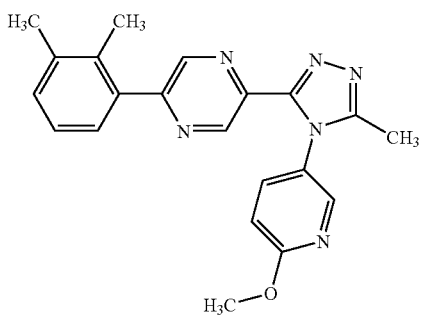

The title product was prepared by the method of example 11 using the product of preparation 23. 14 mg, 3% of the desired product was produced as a white solid.

¹HNMR (CDCl$_3$, 400 MHz) δ: 2.22 (s, 3H), 2.34 (s, 3H), 2.39 (s, 3H), 4.01 (s, 3H), 6.88 (d, 1H), 7.18-7.25 (m, 3H), 7.52 (dd, 1H), 8.09 (d, 1H), 8.37 (s, 1H), 9.49 (s, 1H). MS APCl+ m/z 373 [MH]$^+$

Example 14

2-(4-Fluoro-2-methylphenyl)-5-[4-(6-methoxypyridin-3-yl)-5-methyl-4H-[1,2,4]triazol-3-yl]-pyrazine

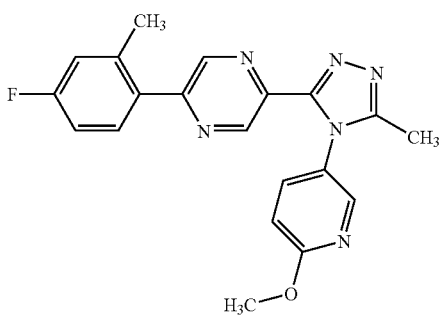

The chloro compound of preparation 30 (800 mg, 2.60 mmol), 4-fluoro-2-methylphenyl boronic acid (470 mg, 3.12 mmol), the palladium complex of preparation 3 (5 mg) and caesium carbonate (2.50 g, 7.90 mmol) were added to 1,4-dioxan (80 mL) and the reaction mixture heated to reflux for 2 hours. The mixture was filtered through a filter tube and then filtered through a pad of silica eluting with dichloromethane: methanol 96:4. The filtrate was concentrated in vacuo and purified by column chromatography on silica gel, eluting with dichloromethane:methanol 100:0 to 95:5 to afford the title product as a white solid in 66% yield, 646 mg.

¹HNMR (CDCl$_3$, 400 MHz) δ: 2.39 (s, 3H), 2.41 (s, 3H), 4.01 (s, 3H), 6.89 (d, 1H), 6.95-7.03 (m, 2H), 7.38 (dd, 1H), 7.54 (dd, 1H), 8.09 (d, 1H), 8.38 (d, 1H), 9.49 (d, 1H). MS APCl+ m/z 377 [MH]$^+$

Alternative Method

Dimethylacetamide dimethylacetal (28 mL, 192.1 mmol) was added to a suspension of the product of preparation 92 (31.5 g, 127.9 mmol) in glacial acetic acid (315 mL) and the mixture was heated at 60° C. for 5 hours. 5-Amino-2-methoxy pyridine (23.9 g, 192 mmol) was added and the mixture was heated at 100° C. for a further 6 hours. The mixture was then cooled to room temperature and evaporated under reduced pressure. The residue was taken up in dichloromethane (750 mL) and washed with saturated sodium hydrogen carbonate solution (1 L). The organic solution was dried over magnesium sulfate and concentrated in vacuo. Re-crystallisation of the residue from hot acetone then afforded the title compound as a white solid in 31% yield, 14.81 g.

Example 15

2-(4-Cyano-2-methylphenyl)-5-[4-(6-methoxypyridin-3-yl)-5-methyl-4H-[1,2,4]triazol-3-yl]-pyrazine

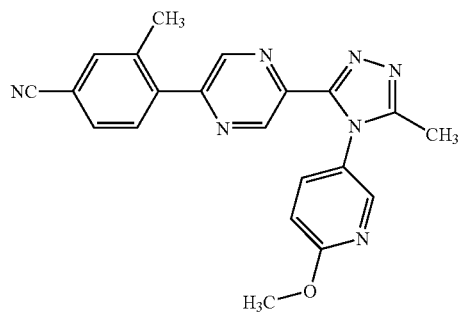

The title product was prepared by the method of example 14 using the chloro compound of preparation 30 (200 mg, 0.66 mmol) and the product of preparation 29 (240 mg, 0.99 mmol). 68 mg, 27% yield of the title product was prepared as a white solid.

¹HNMR (CDCl$_3$, 400 MHz) δ: 2.40 (s, 3H), 2.43 (s, 3H), 4.01 (s, 3H), 6.90 (d, 1H), 7.50-7.55 (m, 2H), 7.57 (s, 1H), 7.60 (s, 1H), 8.08 (d, 1H), 8.41 (d, 1H), 9.55 (d, 1H). Microanalysis: C$_{21}$H$_{17}$N$_7$O 0.1; H$_2$O requires; C, 65.79; H, 4.47; N, 25.57. found C, 65.23; H, 4.48; N, 25.09. MS APCl+ m/z 384 [MH]$^+$

Example 16

2-(5-Fluoro-2-methoxyphenyl)-5-[4-(6-methoxypyridin-3-yl)-5-methyl-4H-[1,2,4]triazol-3-yl]-pyrazine

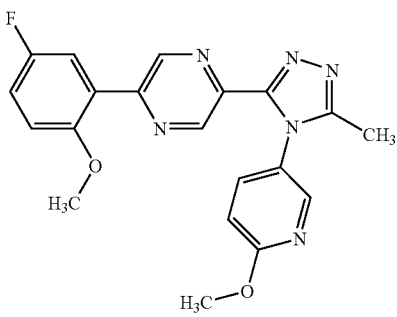

The title product was prepared by the method of example 14 using the chloro compound of preparation 30 (200 mg, 0.66 mmol) and 5-fluoro-2-methoxyphenyl boronic acid (168 mg, 0.99 mmol). 150 mg, 58% yield of the title product was prepared as a cream solid.

$^1$HNMR (CDCl$_3$, 400 MHz) δ: 2.37 (s, 3H), 3.85 (s, 3H), 4.00 (s, 3H), 6.88 (d, 1H), 6.92 (dd, 1H), 7.09 (m, 1H), 7.50 (dd, 1H), 7.68 (dd, 1H), 8.07 (d, 1H), 8.93 (d, 1H), 9.46 (d, 1H).

Example 17

2-(4-Cyano-2-methylphenyl)-5-[5-methoxymethyl-4-(6-methoxypyridin-3-yl)-4H-[1,2,4]triazol-3-yl]-pyrazine

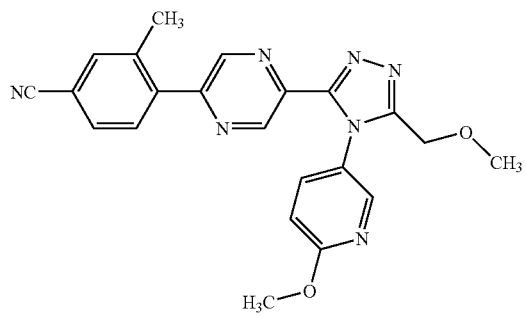

The title product was prepared by the method of example 14 using the chloro compound of preparation 31 (1.0 g, 3.0 mmol) and preparation 29 (1.02 g, 4.2 mmol). 814 mg, 66% yield of the desired product was prepared as a pale yellow solid.

$^1$HNMR (CDCl$_3$, 400 MHz) δ: 2.35 (s, 3H), 3.15 (s, 3H), 3.80 (s, 3H), 4.45 (s, 2H), 6.95 (d, 1H), 7.65-7.90 (m, 4H). MS APCl+ m/z 414 [MH]$^+$

Example 18

5-(4-Cyano-2-methylphenyl)-2-[5-methoxymethyl-4-(6-methoxypyridin-3-yl)-4H-[1,2,4]triazol-3-yl]-pyridine

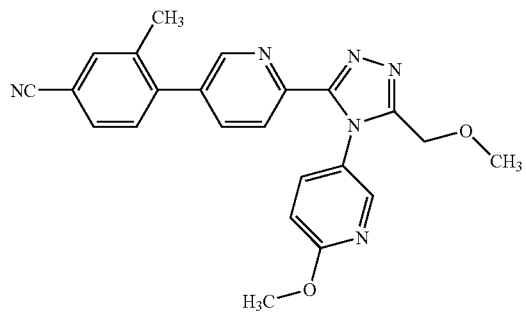

The title product was prepared by the method of example 7 using the product of preparation 29 (100 mg, 0.41 mmol) and the bromo compound of preparation 18 (155 mg, 0.41 mmol).

67 mg 39% yield of the desired product was prepared as a white solid.

$^1$HNMR (CDCl$_3$, 400 MHz) δ: 2.28 (s, 3H), 3.35 (s, 3H), 3.99 (s, 3H), 4.50 (s, 2H), 6.85 (d, 1H), 7.28 (d, 1H), 7.52-7.58 (m, 2H), 7.62 (dd, 1H), 7.74 (dd, 1H), 8.11 (d, 1H), 8.28 (dd, 1H), 8.33 (1H, d). Microanalysis: C$_{23}$H$_{20}$N$_6$O$_2$□0.5H$_2$O requires; C, 66.55; H, 5.02; N, 19.94. found C, 66.02; H, 4.90; N, 19.83. MS APCl+ m/z 413 [MH]$^+$ Example 19

2-(5-Fluoro-2-methoxyphenyl)-5-[5-methoxymethyl-4-(6-methoxypyridin-3-yl)-4H-[1,2,4]triazol-3-yl]-pyridine

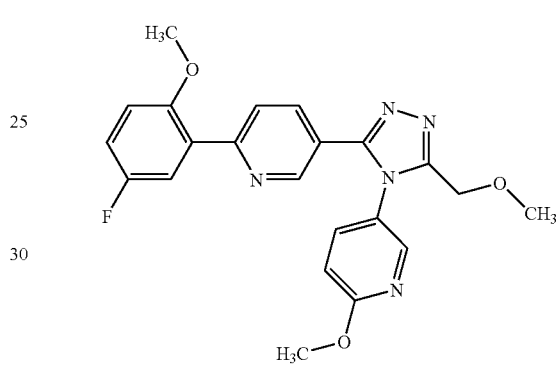

The title compound was prepared using the method of example 11, using the oxadiazole compound of preparation 32 and 5-amino-2-methoxy pyridine, as a pale green solid (325 mg, 30%).

$^1$HNMR (CDCl$_3$, 400 MHz) δ: 3.36 (s, 3H), 3.84 (s, 3H), 3.98 (s, 3H), 4.49 (s, 2H), 6.87 (d, 1H), 6.92 (dd, 1H), 7.06 (m, 1H), 7.54 (dd, 1H), 7.58 (dd, 1H), 7.96-8.00 (m, 2H), 8.14 (d, 1H), 8.60 (d, 1H). MS APCl+ m/z 422 [MH]$^+$

Examples 20-22

The following compounds, of the general formula shown below, were prepared by the method of examples 1-4 using the products of preparations 46 or 47 and the appropriate boronic acid.

The crude compounds were purified firstly by column chromatography on silica gel, eluting with ethyl acetate:methanol:0.88 ammonia, 100:0:0 to 99:1:0.1 to 95:5:0.5, followed by purification by HPLC using a Phenomenex Luna C18 system, eluting with water/acetonitrile/trifluoroacetic acid (5:95:0.1):acetonitrile, 95:5 to 5:95.

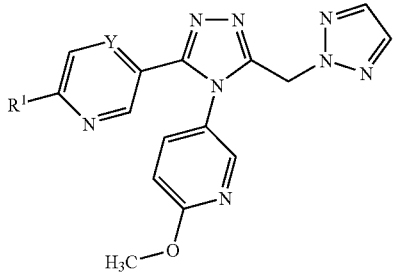

| No. | R¹ | Y | Data | Yield |
|---|---|---|---|---|
| 20 | NC-C₆H₃(CH₃)- | CH | ¹HNMR(CDCl₃, 400 MHz) δ: 2.37 (s, 3H), 3.97(s, 3H), 5.77(s, 2H), 6.80(d, 1H), 7.31(dd, 1H), 7.45(m, 2H), 7.56(m, 4H), 7.99(d, 1H), 8.04(dd, 1H), 8.66(dd, 1H). MS APCl+ m/z 450 [MH]⁺ | 21% |
| 21 | NC-C₆H₃(CH₃)- | N | ¹HNMR(CDCl₃, 400 MHz) δ: 2.40 (s, 3H), 3.97(s, 3H), 5.77(s, 2H), 6.75(d, 1H), 7.35(dd, 1H), 7.50(d, 1H), 7.54-7.67(m, 4H), 7.95(d, 1H), 8.41(s, 1H), 9.58(s, 1H). MS APCl+ m/z 450 [MH]⁺ | 15% |
| 22 | F-C₆H₃(CH₃)- | CH | ¹HNMR(CDCl₃, 400 MHz) δ: 2.34 (s, 3H), 3.97(s, 3H), 5.77(s, 2H), 6.78(d, 1H), 6.95(m, 2H), 7.30(dd, 1H), 7.35(dd, 1H), 7.42(dd, 1H), 7.57(s, 2H), 8.00(m, 2H), 8.60(d, 1H) MS APCl+ m/z 443 [MH]⁺ | 43% |

Example 23

4-{5-[5-(Methoxymethyl)-4-(6-methoxypyridin-3-yl)-4H-1,2,4-triazol-3-yl]pyridin-2-yl}-3-methylbenzonitrile

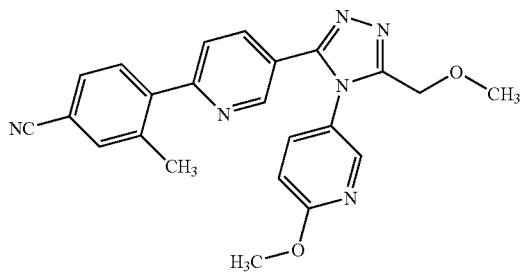

The chloro compound of preparation 49 (170 mg, 0.87 mmol), the palladium complex of preparation 3 (5 mg, cat.), caesium carbonate (847 mg, 2.61 mmol) and the product of preparation 29 (317 mg, 1.31 mmol) were suspended in 1,4-dioxan (5 mL) and the reaction mixture heated to 110° C. for 2 hours. The reaction mixture was diluted with ethyl acetate and water, and filtered through Celite®. The layers of the filtrate were separated and the aqueous solution was re-extracted with ethyl acetate (×2). The combined organic solutions were then washed with brine, dried over sodium sulfate and concentrated in vacuo. The residue was purified by column chromatography on silica gel eluting with dichloromethane:methanol:0.88 ammonia 100:0:0 to 97.5:2.5:0.25 to afford the title compound as a white foam in 45% yield, 160 mg.

¹HNMR (CDCl₃, 400 MHz) δ: 2.38 (s, 3H), 3.38 (s, 3H), 4.00 (s, 3H), 4.51 (s, 2H), 6.90 (d, 1H), 7.45 (d, 1H), 7.48 (d, 1H), 7.55-7.60 (m, 3H), 8.03 (dd, 1H), 8.15 (d, 1H), 8.70 (dd, 1H). MS APCl+ m/z 413 [MH]⁺

Examples 24 to 28

The following compounds, of the general formula shown below, were prepared by the method of example 23, using the appropriate triazole compounds (preparations 31 and 50-51) and boronic acids.

| No. | R¹ | Y | R² | Yield |
|---|---|---|---|---|
| 24 | NC-phenyl-CH₃ | CH | H | 37% |
| Data | ¹HNMR(CDCl₃, 400 MHz) δ: 2.38(s, 3H), 2.41(s, 3H), 4.00(s, 3H), 6.92(d, 1H), 7.45(m, 3H), 7.55(s, 1H), 7.58(s, 1H), 8.02(dd, 1H), 8.12(d, 1H), 8.66(d, 1H). Microanalysis: $C_{22}H_{18}N_6O$ requires; C 69.10, H 4.74, N 21.98 found C 68.74, H 4.75, N 21.83. MS APCl+ m/z 383 [MH]⁺ | | | |
| 25 | F-phenyl-OCH₃ | CH | H | 83% |
| Data | ¹HNMR(CDCl₃, 400 MHz) δ: 2.39(s, 3H), 3.83(s, 3H), 3.99(s, 3H), 6.88-6.94(m, 2H), 7.05(m, 1H), 7.45(dd, 1H), 7.58(s, 1H), 7.97(m, 2H), 8.11(d, 1H), 8.57(d, 1H). MS APCl+ m/z 392 [MH]⁺ | | | |
| 26 | F-phenyl-OCH₃ | N | OCH₃ | 35% |
| Data | ¹HNMR(CDCl₃, 400 MHz) δ: 3.35(s, 3H), 3.86(s, 3H), 4.00(s, 3H), 4.49(s, 2H), 6.71 (dd, 1H), 6.80(m, 1H), 6.85(d, 1H), 7.59(dd, 1H), 7.91(dd, 1H), 8.12(d, 1H), 8.88(d, 1H), 9.44(d, 1H). MS APCl+ m/z 423 [MH]⁺ | | | |
| 27 | NC-phenyl-CH₃ | CH | H₃C-O-CH₂CH₂-O- | 31% |
| Data | ¹HNMR(CDCl₃, 400 MHz) δ: 2.38(s, 3H), 3.34(s, 3H), 3.50(m, 2H), 3.66(m, 2H), 3.99(s, 3H), 4.62(s, 2H), 6.88(d, 1H), 7.44(d, 1H), 7.48(d, 1H), 7.56(d, 2H), 7.66(dd, 1H), 8.02(dd, 1H), 8.15(d, 1H), 8.70(d, 1H). Microanalysis: $C_{25}H_{24}N_6O_3$ 0.5H₂O requires; C 64.50, H 5.41, N 18.05; found C 64.71, H 5.33, N 17.94. MS APCl+ m/z 457 [MH]⁺ | | | |
| 28 | F-phenyl-CH₃ | CH | H₃C-O-CH₂CH₂-O- | 90% |
| Data | ¹HNMR(CDCl₃, 400 MHz) δ: 2.35(s, 3H), 3.34(s, 3H), 3.50(m, 2H), 3.66(m, 2H), 3.98(s, 3H), 4.62(s, 2H), 6.87(d, 1H), 6.93-7.00(m, 2H), 7.36(dd, 1H), 7.41(d, 1H), 7.65(dd, 1H), 7.97(dd, 1H), 8.15(d, 1H), 8.64(d, 1H). MS APCl+ m/z 450 [MH]⁺ | | | |

Example 29

[5-[6-(4-Fluoro-2-methyl-phenyl)-pyridin-3-yl]-4-(6-methoxy-pyridin-3-yl)-4H-[1,2,4]triazol-3-ylm-ethyl]-dimethyl-amine

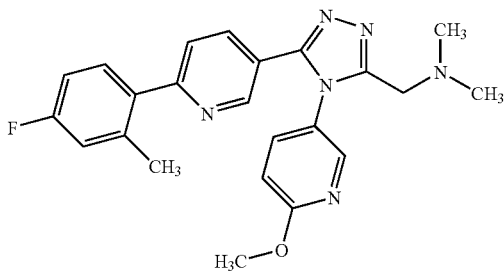

The title compound was prepared from the product of preparation 48 and 4-fluoro-2-methylphenylboronic acid, using the method of examples 1-4, as a white foam in 70% yield.

¹HNMR (CDCl₃, 400 MHz) δ: 2.25 (s, 6H), 2.34 (s, 3H), 3.47 (s, 2H), 3.99 (s, 3H), 6.86 (d, 1H), 6.93-7.00 (m, 2H), 7.38 (m, 2H), 7.64 (dd, 1H), 8.00 (dd, 1H), 8.16 (d, 1H), 8.63 (d, 1H). Microanalysis: $C_{23}H_{23}FN_6O$ 0.25H₂O requires; C, 65.31; H, 5.60; N, 19.87. found C, 65.19; H, 5.63; N, 19.58. MS APCl+ m/z 419 [MH]⁺

Example 30

5-{3-(Ethoxymethyl)-5-[6-(4-fluoro-2-methylphe-nyl)pyridin-3-yl]-4H-1,2,4-triazol-4-yl}-2-methoxy-pyridine

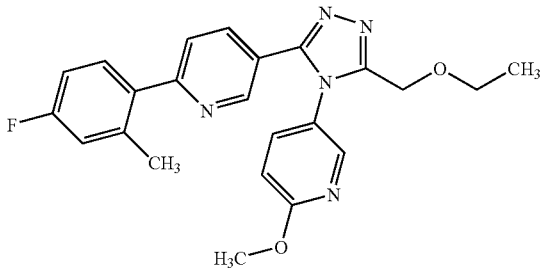

The chloro compound of preparation 52 (230 mg, 0.67 mmol), the palladium complex of preparation 3 (10 mg, cat.), caesium carbonate (648 mg, 2.01 mmol) and 4-fluoro-2-methylphenylboronic acid (143 mg, 0.94 mmol) were suspended in 1,4-dioxan (4 mL) and the reaction mixture heated to 110° C. for 2 hours. A further amount of the product of preparation 3 (5 mg) was added and heating continued for 3.5 hours. The mixture was then partitioned between ethyl acetate and water, and the organic layer was separated, dried over sodium sulfate and concentrated in vacuo. The residue was purified HPLC using a Phenomenex Luna C18 system, eluting with water/acetonitrile/trifluoroacetic acid (5:95:0.1):acetonitrile, 95:5 to 5:95 to afford the title compound as a white powder in 16% yield, 44 mg.

¹HNMR (CDCl₃, 400 MHz) δ: 1.16 (t, 3H), 2.35 (s, 3H), 3.54 (q, 2H), 3.99 (s, 3H), 4.55 (s, 2H), 6.88 (d, 1H), 6.93-7.00

(m, 2H), 7.34-7.42 (m, 2H), 7.56 (dd, 1H), 8.00 (dd, 1H), 8.16 (d, 1H), 8.65 (d, 1H). Microanalysis: $C_{23}H_{22}FN_5O_2$ 0.5$H_2O$ requires; C, 64.48; H, 5.41; N, 16.35. found C, 64.46; H, 5.27; N, 16.40. MS APCl+ m/z 420 [MH]$^+$ Example 31

4-{5-[5-(Ethoxymethyl)-4-(6-methoxypyridin-3-yl)-4H-1,2,4-triazol-3-yl]pyridin-2-yl}-3-methylbenzonitrile

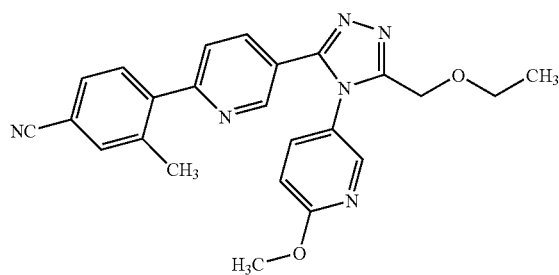

The title compound was prepared from the product of preparation 52 and the product of preparation 29, using the method of example 30, as a beige solid in 15% yield.

$^1$HNMR (CDCl$_3$, 400 MHz) δ: 1.16 (t, 3H), 2.38 (s, 3H), 3.52 (q, 2H), 4.00 (s, 3H), 4.55 (s, 2H), 6.89 (d, 1H), 7.43 (d, 1H), 7.49 (d, 1H), 7.58 (m, 3H), 8.02 (dd, 1H), 8.17 (d, 1H), 8.70 (d, 1H). Microanalysis: $C_{24}H_{22}N_6O_2$ 0.5$H_2O$ requires; C, 66.19; H, 5.32; N, 19.30. found C, 66.57; H, 5.17; N, 19.53. MS ES+ m/z 427 [MH]$^+$ Example 32

2-(3,4-Dimethyl-phenyl)-5-[5-methoxymethyl-4-(6-methoxy-pyridin-3-yl)-4H-[1,2,4]triazol-3-yl]-pyrazine

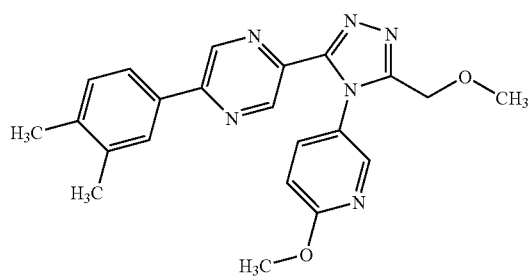

The title compound was prepared from the product of preparation 31 and 3,4-dimethylbenzene boronic acid, using the method of example 30. The crude compound was purified by column chromatography on silica gel, eluting with dichloromethane:methanol:0.88 ammonia, 96:4:0.4 followed by 100% ethyl acetate to afford the desired compound as a beige solid in 68% yield.

$^1$HNMR (CDCl$_3$, 400 MHz) δ: 2.31 (s, 3H), 2.33 (s, 3H), 3.35 (s, 3H), 4.00 (s, 3H), 4.50 (s, 2H), 6.85 (d, 1H), 7.23 (s, 1H), 7.58 (dd, 1H), 7.71 (dd, 1H), 7.80 (s, 1H), 8.11 (d, 1H), 8.71 (d, 1H), 9.42 (d, 1H). MS APCl+ m/z 403 [MH]$^+$

Example 33

4-{4-[5-Methoxymethyl-4-(6-methoxy-pyridin-3-yl)-4H-[1,2,4]triazol-3-yl]-phenyl}-2,3-dimethyl-pyridine 1-oxide

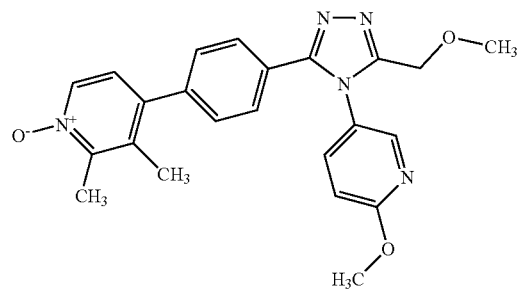

A mixture of the product of preparation 57 (230 mg, 0.74 mmol), 5-amino-2-methoxy pyridine (100 mg, 0.81 mmol) and para-toluenesulfonic acid (30 mg, cat.) in xylene (4 mL) was heated under reflux for 18 hours. The mixture was then acidified with 1M hydrochloric acid and washed with ethyl acetate and the organic layer was discarded. The aqueous solution was basified with 1M sodium hydroxide solution and extracted with ethyl acetate (×2). The combined organic extracts were washed with brine, dried over sodium sulfate and concentrated in vacuo to give a brown oil. Purification of the oil by column chromatography on silica gel, eluting with dichloromethane:methanol:0.88 ammonia, 100:0:0 to 98:2: 0.1, afforded the title compound as a beige foam in 24% yield, 74 mg.

$^1$HNMR (CDCl$_3$, 400 MHz) δ: 2.16 (s, 3H), 2.53 (s, 3H), 3.31 (s, 3H), 3.94 (s, 3H), 4.43 (s, 2H), 6.81 (d, 1H), 6.94 (d, 1H), 7.19 (m, 2H), 7.49 (m, 3H), 8.08 (d, 1H), 8.16 (d, 1H). MS APCl+ m/z 418 [MH]$^+$

Example 34

2-(4-Fluoro-2-methylphenyl)-5-[4-(6-methoxypyridin-3-yl)-5-methyl-4H-1,2,4-triazol-3-yl]pyridine

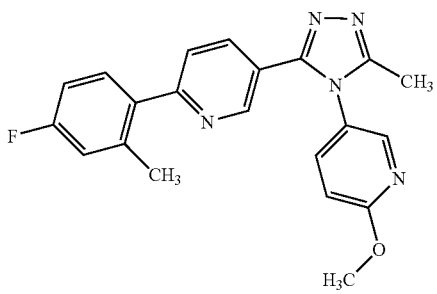

The title compound was prepared from the product of preparation 72 and 5-amino-2-methoxy pyridine, using the method of example 33, as a brown solid in 54% yield.

¹HNMR (CDCl₃, 400 MHz) δ: 2.34 (s, 3H), 2.39 (s, 3H), 3.99 (s, 3H), 6.87-7.01 (m, 3H), 7.35 (dd, 1H), 7.39 (dd, 1H), 7.45 (dd, 1H), 7.97 (dd, 1H), 8.11 (d, 1H), 8.59 (d, 1H). MS APCl+ m/z 376 [MH]⁺

Examples 35 to 45

The following compounds, of the general formula shown below, were prepared by the method of example 34 using the appropriate oxadiazole (preparations 73-81) and aminopyridine.

The progress of the reactions was monitored by tlc analysis and the mixtures were heated under reflux until all of the starting materials had been consumed.

| No. | R¹ | R² | Y | Data | Yield |
|---|---|---|---|---|---|
| 35 | 4-F-2-CH₃-phenyl | OCH₃ | CH | ¹HNMR(CDCl₃, 400 MHz) δ: 2.07(s, 3H), 2.34(s, 3H), 3.32(s, 3H), 3.97(s, 3H), 4.38(d, 1H), 4.49(d, 1H), 6.74(d, 1H), 6.95(m, 2H), 7.35(dd, 1H), 7.39(d, 1H), 7.50(d, 1H), 8.02(d, 1H), 8.65(d, 1H). MS APCl+ m/z 420 [MH]⁺ | 25% |
| 36 | 4-F-2-CH₃-phenyl | OCH₃ | N | ¹HNMR(CDCl₃, 400 MHz) δ: 2.12(s, 3H), 2.38(s, 3H), 3.32(s, 3H), 3.99(s, 3H), 4.39(d, 1H), 4.49(d, 1H), 6.66(d, 1H), 6.99(m, 2H), 7.37(d, 1H), 7.39(d, 1H), 8.39(d, 1H), 9.52(d, 1H). MS APCl+ m/z 421 [MH]⁺ | 33% |

-continued
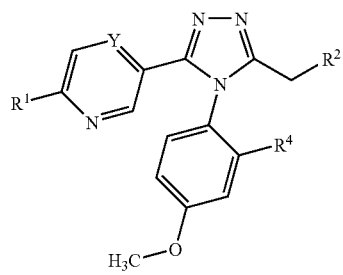
| No. | R¹ | R² | Y | Data | Yield |
|---|---|---|---|---|---|
| 37 | 4-F, 2-CH₃ phenyl | H | N | $^1$HNMR(CDCl$_3$, 400 MHz) δ: 2.17(s, 3H), 2.23(s, 3H), 2.44(s, 3H), 4.00(s, 3H), 6.64(d, 1H), 7.01(m, 2H), 7.37(m, 2H), 8.37(s, 1H), 9.43(s, 1H). MS APCl+ m/z 390 [MH]⁺ | 50% |
| 38 | 2,3-diCH₃ phenyl | H | N | $^1$HNMR(CDCl$_3$, 400 MHz) δ: 2.15(s, 3H), 2.21(s, 3H), 2.31(s, 3H), 2.33(s, 3H), 3.99(s, 3H), 6.68(d, 1H), 7.18(m, 2H), 7.24(m, 1H), 7.33(d, 1H), 8.35(d, 1H), 9.50(d, 1H). MS APCl+ m/z 387 [MH]⁺ | 36% |
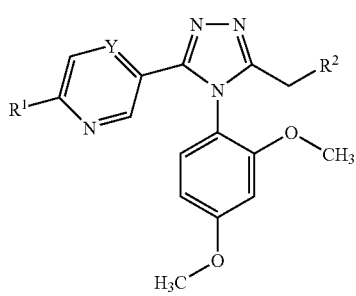
| No. | R¹ | R² | Y | Data | Yield |
|---|---|---|---|---|---|
| 39 | 4-F, 2-CH₃ phenyl | H | N | $^1$HNMR(CDCl$_3$, 400 MHz) δ: 2.33(s, 3H), 2.38(s, 3H), 3.82(s, 3H), 3.98(s, 3H), 6.41(d, 1H), 6.99(m, 2H), 7.38(dd, 1H), 7.43(d, 1H), 8.38(d, 1H), 9.45(d, 1H). MS APCl+ m/z 407 [MH]⁺ | 69% |
| 40 | 2,3-diCH₃ phenyl | H | N | $^1$HNMR(CDCl$_3$, 400 MHz) δ: 2.21(s, 3H), 2.33(m, 6H), 3.82(s, 3H), 3.98(s, 3H), 6.41(s, 1H), 7.21(m, 3H), 7.44(d, 1H), 8.37(d, 1H), 9.44(d, 1H). MS APCl+ m/z 403 [MH]⁺ | 49% |

-continued

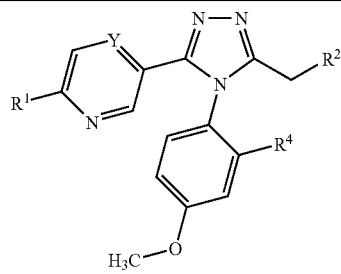

| No. | R¹ | R² | Y | Data | Yield |
|---|---|---|---|---|---|
| 41 | (4-F, 3-CH₃-phenyl) | OCH₃ | N | ¹HNMR(CDCl₃, 400 MHz) δ: 2.34(d, 3H), 3.35(s, 3H), 4.00(s, 3H), 4.50(s, 2H), 6.85(d, 1H), 7.10(dd, 1H), 7.58(dd, 1H), 7.79(m, 1H), 7.87(dd, 1H), 8.11(d, 1H), 8.69(d, 1H), 9.44(d, 1H) MS APCl+ m/z 407 [MH]⁺ | 33% |
| 42 | (3-OCH₃, 2-F-phenyl) | OCH₃ | N | ¹HNMR(CDCl₃, 400 MHz) δ: 3.36(s, 3H), 3.93(s, 3H), 4.01(s, 3H), 4.51(s, 2H), 6.86(d, 1H), 7.06(dd, 1H), 7.21(dd, 1H), 7.57(m, 2H), 8.11(d, 1H), 8.79(d, 1H), 9.51(d, 1H) MS APCl+ m/z 423 [MH]⁺ | 40% |
| 43 | (2-OCH₃, 4-CH₃-phenyl) | OCH₃ | N | ¹HNMR(CDCl₃, 400 MHz) δ: 2.34(s, 3H), 3.35(s, 3H), 3.83(s, 3H), 4.00(s, 3H), 4.50(s, 2H), 6.85(d, 1H), 6.89(d, 1H), 7.19-7.26(m, 1H), 7.59(dd, 1H), 7.68(s, 1H), 8.12(d, 1H), 8.91(s, 1H), 9.44(d, 1H). MS APCl+ m/z 419 [MH]⁺ | 31% |
| 44 | (2-OCH₃, 4-F-phenyl) | OCH₃ | N | ¹HNMR(CDCl₃, 400 MHz) δ: 3.35(s, 3H), 3.85(s, 3H), 4.00(s, 3H), 4.50(s, 2H), 6.85(d, 1H), 6.93(d, 1H), 7.10(m, 1H), 7.59(dd, 1H), 7.69(s, 1H), 8.12(d, 1H), 8.96(s, 1H), 9.47(d, 1H). MS APCl+ m/z 423 [MH]⁺ | 39% |
| 45 | (2,6-dimethyl-phenyl) | OCH₃ | N | ¹HNMR(CDCl₃, 400 MHz) δ: 2.33(s, 3H), 2.34(s, 3H), 3.35(s, 3H), 4.00(s, 3H), 4.50(s, 2H), 6.85(d, 1H), 7.17(dd, 2H), 7.24(m, 1H), 7.60(dd, 1H), 8.13(d, 1H), 8.43(d, 1H), 9.48(d, 1H). MS APCl+ m/z 403 [MH]⁺ | 41% |

Example 42 crude product was re-purified by column chromatography on silica gel, eluting with ethyl acetate:methanol, 98:2.

Examples 35, 37, 38, 41, 43, 44 and 45 crude products were purified by trituration with diethyl ether.

Example 46

5-{3-[5-(4-Fluoro-2-methyl-phenyl)-pyrazin-2-yl]-5-methyl-[1,2,4]triazol-4-yl}-pyridin-2-yl)-methyl-amine

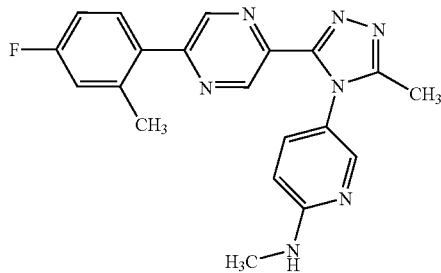

A mixture of the product of preparations 74 (437 mg, 1.62 mmol) and 83 (434 mg, 3.52 mmol) and para-toluenesulfonic acid in xylene (10 mL) was heated under reflux for 100 hours. The mixture was then filtered through Celite®, washing through with dichloromethane and the filtrate was concentrated in vacuo. Purification by column chromatography on silica gel, eluting with dichloromethane:methanol:0.88 ammonia, 98:2:0.2, followed by ethyl acetate:methanol, 98:2, afforded the title compound as a beige solid in 9% yield, 57 mg.

$^1$HNMR (CDCl$_3$, 400 MHz) δ: 2.38 (m, 6H), 2.98 (d, 3H), 4.89 (m, 1H), 6.47 (d, 1H), 6.94-7.02 (m, 2H), 7.36 (m, 2H), 7.97 (d, 1H) 8.43 (s, 1H), 9.41 (d, 1H). MS APCl+ m/z 376 [MH]$^+$

Example 47

3-(4-Fluoro-2-methyl-phenyl)-6-[5-methoxymethyl-4-(6-methoxy-pyridin-3-yl)-4H-[1,2,4]triazol-3-yl]-pyridazine

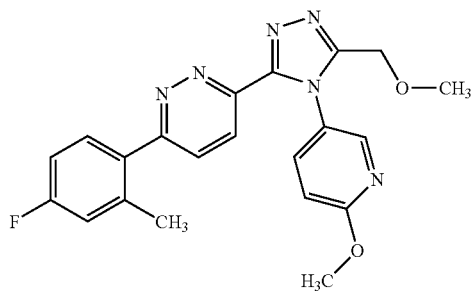

The product of preparation 62 (40 mg, 0.13 mmol), 5-amino-2-methoxypyridine (16 mg, 0.13 mmol) and para-toluenesulfonic acid monohydrate (5 mg, cat) were dissolved in xylene (2 mL) and the reaction mixture was heated under reflux for 3 hours. The reaction mixture was then partitioned between dichloromethane and sodium hydrogen carbonate solution and the organic solution was washed with brine, dried over sodium sulfate and concentrated in vacuo. The residue was purified by HPLC using a Phenomenex Luna C18 system, eluting with water/acetonitrile/trifluoroacetic acid (5:95:0.1):acetonitrile, 95:5 to 5:95 to afford the title compound as a yellow oil in 8% yield, 4 mg.

$^1$HNMR (CDCl$_3$, 400 MHz) δ: 2.33 (s, 3H), 3.36 (s, 3H), 3.94 (s, 3H), 4.52 (s, 2H), 6.83 (d, 1H), 7.02 (m, 2H), 7.39 (d, 1H), 7.70 (m, 2H) 8.11 (s, 1H), 8.46 (d, 1H).

Example 48

5-(4-Fluoro-2-methyl-phenyl)-2-[5-methoxymethyl-4-(6-methoxy-pyridin-3-yl)-4H-[1,2,4]triazol-3-yl]-pyrimidine

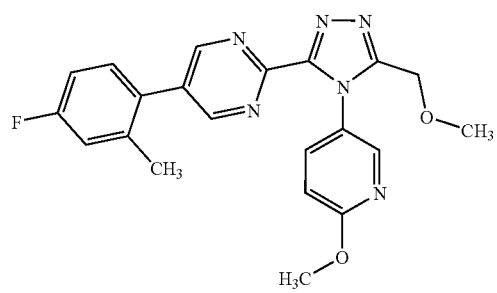

The product of preparation 69 (80 mg, 0.27 mmol), 5-amino-2-methoxypyridine (50 mg, 0.39 mmol) and para-toluenesulfonic acid monohydrate (10 mg, cat) were dissolved in xylene (3 mL) and the reaction mixture was heated under reflux for 18 hours. Additional para-toluenesulfonic acid monohydrate (10 mg, cat) was added and heating continued for a further 18 hours. The reaction mixture was then evaporated under reduced pressure and the residue was dissolved in ethyl acetate, washed with 1M hydrochloric acid, sodium hydrogen carbonate solution and brine, dried over magnesium sulfate and concentrated in vacuo. Purification of the residue by column chromatography on silica gel, eluting with dichloromethane:methanol, 97:3, afforded the title compound in 46% yield, 49.3 mg.

$^1$HNMR (CDCl$_3$, 400 MHz) δ: 2.23 (s, 3H), 3.32 (s, 3H), 3.99 (s, 3H), 4.51 (s, 2H), 6.82 (d, 1H), 6.98 (m, 2H), 7.17 (d, 1H), 7.60 (d, 1H), 8.11 (s, 1H), 8.67 (s, 2H). MS APCl+ m/z 407 [MH]$^+$

Examples 49 to 52

The following compounds, of the general formula shown below, were prepared by the method of example 48, using the product of preparation 71 and the appropriate boronic acid.

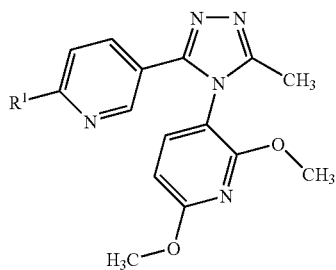

| No. | R¹ | Data | Yield |
|---|---|---|---|
| 49 | (4-fluoro-2-methylphenyl) | ¹HNMR(CDCl₃, 400 MHz) δ: 2.20 (s, 3H), 2.30(s, 3H), 3.79(s, 3H), 3.95(s, 3H), 6.38(d, 1H), 6.88-6.98 (m, 2H), 7.10(dd, 1H), 7.42(d, 1H), 7.65(dd, 1H), 8.19(d, 1H), 8.21(d, 1H). MS APCl+ m/z 406 [MH]⁺ | 50% |
| 50 | (2,3-dimethylphenyl) | ¹HNMR(CDCl₃, 400 MHz) δ: 2.09 (s, 3H), 2.30(s, 3H), 2.39(s, 3H), 3.80(s, 3H), 3.96(s, 3H), 6.39(d, 1H), 6.98(d, 1H), 7.09-7.02(m, 2H), 7.46(d, 1H), 7.68(d, 1H), 8.19(d, 1H), 8.24(d, 1H). MS APCl+ m/z 402 [MH]⁺ | 50% |
| 51 | (4-fluoro-2-methoxyphenyl) | MS APCl+ m/z 422 [MH]⁺ | 69% |
| 52 | (4-fluoro-3-methylphenyl) | MS APCl+ m/z 406 [MH]⁺ | 46% |

Example 53

3-{5-[4-(6-Methoxy-pyridin-3-yl)-5-methyl-4H-[1,2,4]triazol-3-yl]-pyrazin-2-yl}-4-methyl-benzonitrile

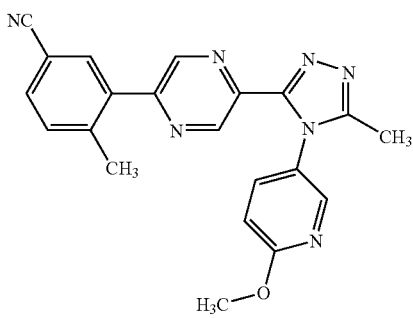

A mixture of 3-chloro-4-methylbenzonitrile (1 g, 6.6 mmol), bis(pinacolato)diboron (1.8 g, 7.0 mmol), caesium carbonate (6.4 g, 19.8 mmol) and the product of preparation 3 (5 mg, cat) in 1,4-dioxan (50 mL) was heated under reflux for 4 hours. The reaction mixture was then cooled to room temperature, filtered through Celite® and concentrated in vacuo.

A portion of the residue (145 mg, 0.6 mmol), the product of preparation 30 (90 mg, 0.3 mmol), caesium carbonate (293 mg, 0.9 mmol) and the product of preparation 3 (2 mg, cat) were then dissolved in 1,4-dioxan and the mixture was heated under reflux for 18 hours. The mixture was then cooled to room temperature, filtered through Celite® and concentrated in vacuo. Purification of the residue by column chromatography on silica gel, eluting with dichloromethane:methanol, 100:0 to 97:3, afforded the title compound as a white solid in 3% yield, 3 mg.

¹HNMR (CDCl₃, 400 MHz) δ: 2.41 (s, 3H), 2.46 (s, 3H), 4.02 (s, 3H), 6.90 (d, 1H), 7.43 (d, 1H), 7.53 (dd, 1H), 7.63 (dd, 1H), 7.70 (d, 1H), 8.09 (d, 1H), 8.41 (d, 1H), 9.55 (d, 1H). MS APCl+ m/z 383 [MH]⁺

Example 54

2-(4-Fluoro-2-methyl-phenyl)-4-methoxy-5-[5-methoxymethyl-4-(6-methoxy-pyridin-3-yl)-4H-[1,2,4]triazol-3-yl]-pyridine

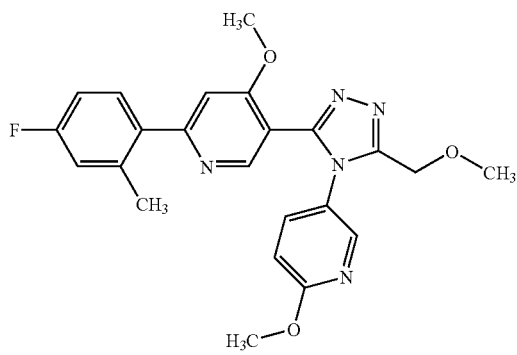

A mixture of the product of preparations 90 (60 mg, 0.17 mmol) and 3 (10 mg, cat), 4-fluoro-2-methylbenzene boronic acid (33 mg, 0.21 mmol) and caesium carbonate (110 mg, 0.34 mmol) in dioxan (4 mL) was heated under reflux for 16 hours. Catalytic amounts of 4-fluoro-2-methylbenzene boronic acid and the product of preparation 3 were then added to the reaction mixture and heating continued for a further 3 hours. The mixture was diluted with dichloromethane and was purified directly by column chromatography on silica gel, eluting with dichloromethane:methanol, 100:0 to 96:4, to obtain the title compound as a white foam in 54% yield, 39 mg.

¹HNMR (CDCl₃, 400 MHz) δ: 2.34 (s, 3H), 3.39 (s, 3H), 3.62 (s, 3H), 3.94 (s, 3H), 4.51 (s, 2H), 6.77 (m, 2H), 6.96 (m, 2H), 7.33 (dd, 1H), 7.50 (dd, 1H), 8.05 (d, 1H), 8.70 (d, 1H). MS APCl+ m/z 436 [MH]⁺

Example 55

2-(5-Fluoro-2-methoxy-phenyl)-4-methoxy-5-[5-methoxymethyl-4-(6-methoxy-pyridin-3-yl)-4H-[1,2,4]triazol-3-yl]-pyridine

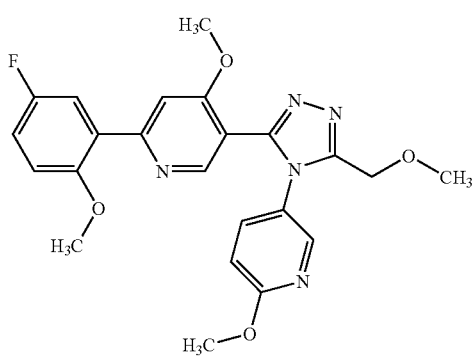

The title compound was prepared from the product of preparation 90 and 5-fluoro-2-methoxybenzene benzoic acid, using the method of example 54, as a yellow foam in 53% yield.

$^1$HNMR (CDCl$_3$, 400 MHz) δ: 3.39 (s, 3H), 3.63 (s, 3H), 3.83 (s, 3H), 3.93 (s, 3H), 4.51 (s, 2H), 6.76 (d, 1H), 6.93 (dd, 1H), 7.07 (m, 1H), 7.41 (s, 1H), 7.49 (dd, 1H), 7.63 (dd, 1H), 8.04 (d, 1H), 8.70 (s, 1H). MS APCl+ m/z 452 [MH]$^+$

Example 56

2-(3-Fluoro-2-methoxy-phenyl)-5-[4-(6-methoxy-pyridin-3-yl)-5-methyl-4-H-[1,2,4]triazol-3-yl]-pyrazine

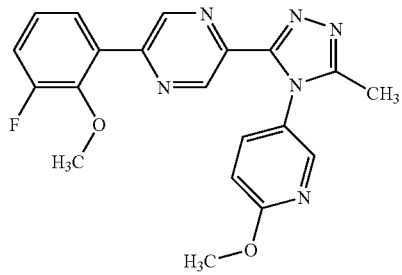

The title product was prepared by the method of example 14 using the chloro compound of preparation 30 (108 mg, 0.32 mmol) and 2-methoxy-3-fluoro-benzene boronic acid (72 mg, 0.48 mmol). 107 mg, 79% yield of the title product was prepared as a white solid.

$^1$HNMR (CDCl$_3$, 400 MHz) δ: 3.35 (s, 3H), 3.85 (s, 3H), 4.00 (s, 3H), 4.5 (s, 2H), 6.85 (d, 1H), 7.20 (m, 2H), 7.60 (m, 2H), 8.15 (s, 1H), 8.85 (s, 1H), 9.50 (s, 1H). Microanalysis: C$_{21}$H$_{19}$FN$_6$O$_3$ 0.2H$_2$O requires; C, 59.21; H, 4.59; N, 19.73. found C, 59.27; H, 4.69; N, 19.33. MS APCl+ m/z 423 [MH]$^+$

The invention claimed is:

1. A compound of formula (I)

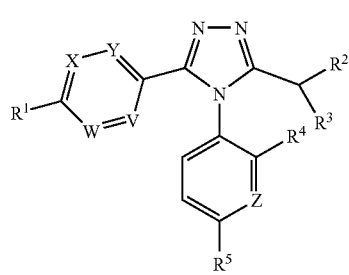

wherein
X and Y are each N;
V and W are each C—R$^6$;
Z is C—H or N;
R$^1$ is selected from:
(i) a phenyl ring substituted with two or more substituents, which may be the same or different, each independently selected from halo, (C$_1$-C$_6$)alkyl, (C$_1$-C$_6$)alkoxy, cyano, C(O)NR$^7$R$^8$, NR$^7$R$^8$, NR$^7$C(O)R$^{10}$ and N[C(O)R$^{10}$]$_2$; and
(ii) a five to seven membered aromatic heterocyclic ring containing 1-3 hetero atoms selected from N, O and S; said ring being optionally substituted with two or more substituents, which may be the same or different, selected from halo, (C$_1$-C$_6$)alkyl, (C$_1$-C$_6$)alkoxy, cyano, C(O)NR$^7$R$^8$, NR$^7$R$^8$, NR$^7$C(O)R$^{10}$ and N[C(O)R$^{10}$]$_2$;
R$^2$ is selected from:
(i) H, OH, OR$^9$, NR$^7$R$^8$, NR$^7$C(O)R$^{10}$ and N[C(O)R$^{10}$]$_2$;
(ii) a 5-7 membered N-linked heterocycle containing 1-3 heteroatoms selected from N, O and S; said ring being optionally substituted with one or more groups selected from (C$_1$-C$_6$)alkyl, (C$_1$-C$_6$)alkoxy and C(O)NR$^7$R$^8$; and
(iii) (C$_1$-C$_6$)alkyl optionally substituted with an N-linked 5-7 membered heterocycle containing 1-3 heteroatoms selected from N, O and S;
R$^3$ is selected from H and (C$_1$-C$_6$)alkyl;
R$^4$ is selected from H, (C$_1$-C$_6$)alkyl and OR$^9$;
R$^5$ is selected from halo, (C$_1$-C$_6$)alkyl, (C$_1$-C$_6$)alkoxy, NR$^7$R$^8$, NR$^7$C(O)R$^{10}$ and N[C(O)R$^{10}$]$_2$;
R$^6$ is selected from H, halo, (C$_1$-C$_6$)alkyl, (C$_1$-C$_6$)alkoxy, cyano, NR$^7$R$^8$, NR$^7$C(O)R$^{10}$, N[C(O)R$^{10}$]$_2$ and C(O)NR$^7$R$^8$;
R$^7$ and R$^8$, which may be the same or different, are selected from H and (C$_1$-C$_6$)alkyl;
R$^9$ is (C$_1$-C$_6$)alkyl, which is optionally substituted with one or more groups each independently selected from (C$_1$-C$_6$)alkoxy and an N-linked 5-7 membered heterocycle containing 1-3 heteroatoms selected from N, O and S; and
R$^{10}$ is selected from (C$_1$-C$_6$)alkyl and (C$_1$-C$_6$)alkoxy;
or a pharmaceutically acceptable salt thereof.

2. The compound according to claim 1 wherein V and W are each CH; or a pharmaceutically acceptable salt thereof.

3. The compound according to claim 1 wherein Z is N; or a pharmaceutically acceptable salt thereof.

4. The compound according to claim 1 wherein Z is CH; or a pharmaceutically acceptable salt thereof.

5. The compound according to claim 1 wherein $R^1$ is selected from:
  (i) a phenyl ring substituted with two substituents, which may be the same or different, each independently selected from halo, $(C_1-C_6)$alkyl, $(C_1-C_6)$alkoxy, cyano, $C(O)NR^7R^8$, $NR^7R^8$, $NR^7C(O)R^{10}$ and $N[C(O)R^{10}]_2$; and
  (ii) a pyridyl ring substituted with two substituents, which may be the same or different, each independently selected from halo, $(C_1-C_6)$alkyl, $(C_1-C_6)$alkoxy, cyano, $C(O)NR^7R^8$, $NR^7R^8$, $NR^7C(O)R^{10}$ and $N[C(O)R^{10}]_2$;
  or a pharmaceutically acceptable salt thereof.

6. The compound according to claim 5 wherein $R^1$ is a phenyl ring substituted with two substituents, which may be the same or different, each independently selected from fluoro, chloro, methyl, methoxy and cyano; or a pharmaceutically acceptable salt thereof.

7. The compound according to claim 5 wherein $R^2$ is selected from:
  (i) H, $(C_1-C_3)$alkoxy, $(C_1-C_3)$alkoxy-$(C_1-C_3)$alkoxy and $N((C_1-C_3)$alkyl$)_2$; and
  (ii) a 5 membered N-linked heterocycle containing 1-3 nitrogen atoms, said ring optionally substituted with $C(O)NR^7R^8$;
  or a pharmaceutically acceptable salt thereof.

8. The compound according to claim 7 wherein $R^1$ is a phenyl ring substituted with two substituents, which may be the same or different, each independently selected from fluoro, chloro, methyl, methoxy and cyano; or a pharmaceutically acceptable salt thereof.

9. The compound according to claim 8 wherein $R^2$ is selected from H, methoxy, ethoxy, 2-methoxyethoxy, dimethylamino, 1,2,3-triazol-2-yl and pyrrolidinyl, wherein said pyrrolidinyl is optionally substituted by $CONH_2$; or a pharmaceutically acceptable salt thereof.

10. The compound according to claim 9 wherein $R^2$ is selected from H and methoxy; or a pharmaceutically acceptable salt thereof.

11. The compound according to claim 10 wherein $R^3$ is H; or a pharmaceutically acceptable salt thereof.

12. The compound according to claim 11 wherein $R^1$ is a phenyl ring substituted with two substituents, which may be the same or different, each independently selected from fluoro, chloro, methyl, methoxy and cyano; or a pharmaceutically acceptable salt thereof.

13. The compound according to claim 12 wherein $R^4$ is H, methyl or methoxy; or a pharmaceutically acceptable salt thereof.

14. The compound according to claim 13 wherein $R^1$ is a phenyl ring substituted with two substituents, which may be the same or different, each independently selected from fluoro, chloro, methyl, methoxy and cyano and $R^2$ is selected from H, methoxy, ethoxy, 2-methoxyethoxy, dimethylamino, 1,2,3-triazol-2-yl and pyrollidinyl, the latter being optionally substituted by $CONH_2$; or a pharmaceutically acceptable salt thereof.

15. The compound according to claim 14 wherein $R^4$ is H.

16. A compound according to claim 1, which is
  3-(4-Fluoro-2-methyl-phenyl)-6-[5-methoxymethyl-4-(6-methoxy-pyridin-3-yl)-4H-[1,2,4]triazol-3-yl]-pyridazine; or a pharmaceutically acceptable salt thereof.

17. A pharmaceutical composition comprising a compound of formula (I) as claimed in claim 1 or a pharmaceutically acceptable salt thereof, and a pharmaceutically acceptable diluent or carrier.

18. A method of palliatively treating male sexual dysfunction, female sexual dysfunction, hypoactive sexual desire disorder, sexual arousal disorder, orgasmic disorder, sexual pain disorder, or premature ejaculation in a mammal, the method comprising administering a therapeutically effective amount of a compound of claim 1 or a pharmaceutically acceptable salt thereof to a mammal in need of treatment thereof.

19. The method according to claim 18 wherein sexual arousal disorder, orgasmic disorder, sexual pain disorder or premature ejaculation is treated.

* * * * *